United States Patent
Pongracz et al.

(10) Patent No.: US 9,708,360 B2
(45) Date of Patent: Jul. 18, 2017

(54) PHOSPHORODIAMIDATE BACKBONE LINKAGE FOR OLIGONUCLEOTIDES

(71) Applicant: Geron Corporation, Menlo Park, CA (US)

(72) Inventors: Krisztina Pongracz, Oakland, CA (US); Mahesh Ramaseshan, Sunnyvale, CA (US)

(73) Assignee: Geron Corporation, Menlo Park, CA (US)

( * ) Notice: Subject to any disclaimer, the term of this patent is extended or adjusted under 35 U.S.C. 154(b) by 157 days.

(21) Appl. No.: 14/498,872

(22) Filed: Sep. 26, 2014

(65) Prior Publication Data
US 2015/0111958 A1    Apr. 23, 2015

Related U.S. Application Data

(60) Provisional application No. 61/884,848, filed on Sep. 30, 2013.

(51) Int. Cl.

| | | |
|---|---|---|
| *A61K 48/00* | (2006.01) | |
| *C07H 21/02* | (2006.01) | |
| *C07H 21/04* | (2006.01) | |
| *C07H 19/10* | (2006.01) | |
| *C07H 19/20* | (2006.01) | |
| *C07H 19/048* | (2006.01) | |
| *C07H 19/04* | (2006.01) | |
| *C07H 21/00* | (2006.01) | |
| *C07H 1/00* | (2006.01) | |

(52) U.S. Cl.
CPC .............. *C07H 21/00* (2013.01); *C07H 1/00* (2013.01); *C07H 19/10* (2013.01); *C07H 19/20* (2013.01)

(58) Field of Classification Search
CPC .......... C07H 1/00; C07H 21/00; C07H 19/10; C07H 19/20
See application file for complete search history.

(56) References Cited

U.S. PATENT DOCUMENTS

| | | | |
|---|---|---|---|
| 5,166,315 A | 11/1992 | Summerton et al. | |
| 5,470,967 A | 11/1995 | Huie et al. | |
| 5,646,260 A | 7/1997 | Letsinger et al. | |
| 5,726,297 A | 3/1998 | Gryaznov et al. | |
| 5,789,562 A | 8/1998 | Seela et al. | |
| 5,859,233 A | 1/1999 | Hirschbein et al. | |
| 5,936,077 A | 8/1999 | Pfleiderer et al. | |
| 6,033,909 A | 3/2000 | Uhlmann et al. | |
| 6,066,720 A | 5/2000 | Seela et al. | |
| 7,321,029 B2 | 1/2008 | Gryaznov et al. | |
| 7,485,717 B2 | 2/2009 | Gryaznov et al. | |
| 2004/0023901 A1 | 2/2004 | Cook et al. | |
| 2016/0130580 A1* | 5/2016 | Gryaznov | C07H 21/00 514/44 A |

FOREIGN PATENT DOCUMENTS

| | | |
|---|---|---|
| WO | 97/31009 A1 | 8/1997 |
| WO | 01/18015 A1 | 3/2001 |
| WO | 02/077184 A2 | 10/2002 |
| WO | 02/077184 A3 | 10/2002 |
| WO | 2005047506 | 5/2005 |
| WO | 2007/127163 A2 | 11/2007 |
| WO | 2007/127163 A3 | 11/2007 |
| WO | 2009/064471 A1 | 5/2009 |

OTHER PUBLICATIONS

Written Opinion of the International Searching Authority mailed on Dec. 19, 2014, for PCT Application No. PCT/US2014/057876, filed on Sep. 26, 2014, 4 pages.
Visser, G.M., et al., (1984) "Synthesis of 3'-amino-3*-deoxyadenosine 5'-triphosphate", Journal of the Royal Netherlands Chemical Society, 103(5)165-168.

* cited by examiner

*Primary Examiner* — Lawrence E Crane
(74) *Attorney, Agent, or Firm* — Glenn J. Foulds; Carol L. Francis; Bozicevic, Field & Francis LLP

(57) ABSTRACT

This invention relates to antisense oligonucleotides comprising at least one N3'→P5' phosphorodiamidate linkage (NPN) in the backbone, and kits and pharmaceutical compositions thereof, useful for modulating gene expression involved in the pathogenesis of a disease. Also included are compounds useful as building blocks of said antisense oligonucleotides and methods of preparing said antisense oligonucleotides and building block compounds including NPN linkages.

24 Claims, No Drawings

PHOSPHORODIAMIDATE BACKBONE LINKAGE FOR OLIGONUCLEOTIDES

CROSS-REFERENCE TO RELATED APPLICATIONS

This application claims priority to U.S. Provisional Application No. 61/884,848 filed Sep. 30, 2013, the disclosure of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 707582000600SEQLIST.txt, date recorded: Oct. 27, 2014, size: 2 KB).

TECHNICAL FIELD

This invention relates to antisense oligonucleotides comprising at least one N3'→P5' phosphorodiamidate linkage (NPN) in the backbone as well as methods for using the same. The antisense oligonucleotides can effectively prevent or decrease protein expression.

BACKGROUND

There is much interest in the medical uses of nucleic acids. For example, antisense, ribozymes, aptamer and RNA interference (RNAi) technologies are all being developed for potential therapeutic applications. The design of nucleic acids, particularly oligonucleotides, for in vivo delivery requires consideration of various factors including binding strength, target specificity, serum stability, resistance to nucleases and cellular uptake. A number of approaches have been proposed in order to produce oligonucleotides that have characteristics suitable for in vivo use, such as modified backbone chemistry, formulation in delivery vehicles and conjugation to various other moieties. Therapeutic oligonucleotides with characteristics suitable for systemic delivery would be particularly beneficial.

Oligonucleotides with modified chemical backbones are reviewed in Micklefield, Backbone modification of nucleic acids: synthesis, structure and therapeutic applications, Curr. Med. Chem., 8 (10):1157-79, 2001 and Lyer et al., *Modified oligonucleotides-synthesis, properties and applications*, Curr. Opin. Mol. Ther., 1 (3): 344-358, 1999.

Examples of modified backbone chemistries include:
- peptide nucleic acids (PNAs) (see Nielsen, Methods Mol. Biol., 208:3-26, 2002),
- locked nucleic acids (LNAs) (see Peterson & Wengel, Trends Biotechnol., 21 (2):74-81, 2003),
- phosphorothioates (see Eckstein, Antisense Nucleic Acid Drug Dev., 10 (2):117-21, 2000),
- methylphosphonates (see Thiviyanathan et al., Biochemistry, 41 (3):827-38, 2002),
- phosphoramidates (see Gryaznov, Biochem. Biophys. Acta, 1489 (1):131-40, 1999; Pruzan et al., Nucleic Acids Res., 30 (2):559-68, 2002), and
- thiophosphoramidates (see Gryaznov et al., Nucleosides Nucleotides Nucleic Acids, 20 (4-7):401-10, 2001; Herbert et al., Oncogene, 21 (4):638-42, 2002).

Each of these types of oligonucleotides has reported advantages and disadvantages. For example, peptide nucleic acids (PNAs) display good nuclease resistance and binding strength, but have reduced cellular uptake in test cultures; phosphorothioates display good nuclease resistance and solubility, but are typically synthesized as P-chiral mixtures and display several sequence-nonspecific biological effects; methylphosphonates display good nuclease resistance and cellular uptake, but are also typically synthesized as P-chiral mixtures and have reduced duplex stability. The N3'→P5' phosphoramidate intersubunit linkages are reported to display favorable binding properties, nuclease resistance, and solubility (Gryaznov and Letsinger, Nucleic Acids Research, 20:3403-3409, 1992; Chen et al., Nucleic Acids Research, 23:2661-2668, 1995; Gryaznov et al., Proc. Natl. Acad. Sci., 92:5798-5802, 1995; Skorski et al., Proc. Natl. Acad. Sci., 94:3966-3971, 1997). However, they also show increased acid lability relative to the natural phosphodiester counterparts (Gryaznov et al., Nucleic Acids Research, 24:1508-1514, 1996). Acid stability of an oligonucleotide is an important quality given the desire to use oligonucleotide agents as oral therapeutics. The addition of a sulfur atom to the backbone in N3'→P5' thiophosphoramidate oligonucleotides provides enhanced acid stability.

As with many other therapeutic compounds, the polyanionic nature of oligonucleotides reduces the ability of the compound to cross lipid membranes, limiting the efficiency of cellular uptake. Various solutions have been proposed for increasing the cellular uptake of therapeutic agents, including formulation in liposomes (for reviews, see Pedroso de Lima et al., Curr Med Chem, 10 (14):1221-1231, 2003 and Miller, Curr Med Chem., 10 (14):1195-211, 2003) and conjugation with a lipophilic moiety. Examples of the latter approach include: U.S. Pat. No. 5,411,947 (Method of converting a drug to an orally available form by covalently bonding a lipid to the drug) and U.S. Pat. No. 6,448,392 (Lipid derivatives of antiviral nucleosides: liposomal incorporation and method of use).

Throughout this specification, various patents, patent applications and other types of publications (e.g., journal articles) are referenced. The disclosure of all patents, patent applications, and publications cited herein are hereby incorporated by reference in their entirety for all purposes.

BRIEF SUMMARY

The present disclosure provided herein discloses, inter alia, compositions and methods for the preparation and use of antisense oligonucleotides comprising at least one N3'→P5' phosphorodiamidate linkage (NPN) in the backbone.

In accordance with this invention, compounds are provided having formula (I):

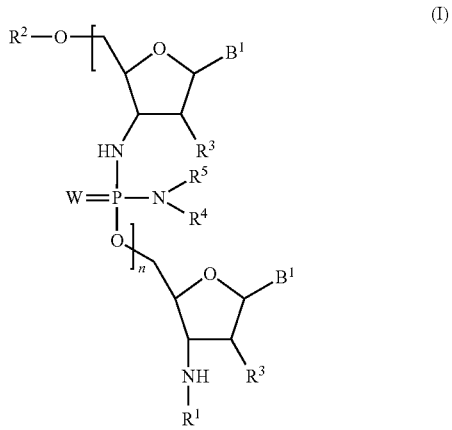

wherein
$R^1$ is hydrogen, an amino protecting group, or an oligonucleotide;
$R^2$ is hydrogen, a hydroxyl protecting group, solid support, or an oligonucleotide;
each $R^3$ is independently selected from hydrogen, hydroxyl, and —O—$R^{3a}$;
  wherein each $R^{3a}$ is $C_{1-6}$ alkyl optionally substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$;
  wherein each $R^{3b}$ is hydrogen or $C_{1-2}$ alkyl;
  each $R^{3c}$ is hydrogen or $C_{1-2}$ alkyl;
  each $R^{3d}$ is hydrogen or $C_{1-2}$ alkyl;
  each a is an integer selected from one to 4;
  each b is an integer selected from one to 4;
each $R^4$ is $C_{1-6}$ alkyl optionally substituted with —$NR^{4a}R^{4b}$;
  wherein $R^{4a}$ is hydrogen or $C_{1-2}$ alkyl and $R^{4b}$ is hydrogen or $C_{1-2}$ alkyl;
each $R^5$ is $C_{1-6}$ alkyl optionally substituted with —$NR^{5a}R^{5b}$;
  wherein $R^{5a}$ is hydrogen or $C_{1-2}$ alkyl and $R^{5b}$ is hydrogen or $C_{1-2}$ alkyl; or
$R^4$ and $R^5$ taken together with the nitrogen to which they are attached form an optionally substituted monocyclic heterocyclyl ring;
each W is independently selected from O, S, and Se;
each $B^1$ is independently selected from an optionally protected heterocyclic base moiety; and
n is an integer selected from one to 50;
or a salt thereof.

In one embodiment of formula (I), each W is O.

In one embodiment of formula (I), each $B^1$ is independently selected from purine and pyrimidine. In another embodiment, each $B^1$ is independently selected from Thy (thymine), BzCyt (4-benzoyl-cytosine), BzAde (6-benzoyl-adenine), AdeDMF (6-dimethylformamidino-adenine), iBuGua (2-isobutyryl-guanine), and GuaDMF (2-dimethylformamidino-guanine). In another embodiment, each $B^1$ is independently selected from adenine, guanine, cytosine, thymine, and uracil.

In one embodiment of formula (I), each $R^3$ is hydrogen.

In one embodiment of formula (I), each $R^4$ and each $R^5$ are methyl.

In one embodiment of formula (I), $R^1$ is hydrogen. In another embodiment, $R^1$ is an amino protecting group.

In one embodiment of formula (I), $R^2$ is hydrogen. In another embodiment, $R^2$ is a hydroxyl protecting group or a solid support.

In one embodiment of formula (I), $R^1$ and $R^2$ are hydrogen. In another embodiment, $R^1$ is an amino protecting group and $R^2$ is a solid support.

In one embodiment of formula (I), n is an integer from one to 30.

In accordance with this invention, compounds are provided having formula (II):

(II)

wherein
$R^1$ is hydrogen or an amino protecting group;
$R^3$ is independently selected from hydrogen, hydroxyl, and —O—$R^{3a}$;
  wherein $R^{3a}$ is $C_{1-6}$ alkyl optionally substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$;
  wherein $R^{3b}$ is hydrogen or $C_{1-2}$ alkyl;
  $R^{3c}$ is hydrogen or $C_{1-2}$ alkyl;
  $R^{3d}$ is hydrogen or $C_{1-2}$ alkyl;
  a is an integer selected from one to 4;
  b is an integer selected from one to 4;
$R^4$ is $C_{1-6}$ alkyl optionally substituted with —$NR^{4a}R^{4b}$;
  wherein $R^{4a}$ is hydrogen or $C_{1-2}$ alkyl and $R^{4b}$ is hydrogen or $C_{1-2}$ alkyl;
$R^5$ is $C_{1-6}$ alkyl optionally substituted with —$NR^{5a}R^{5b}$;
  wherein $R^{5a}$ is hydrogen or $C_{1-2}$ alkyl and $R^{5b}$ is hydrogen or $C_{1-2}$ alkyl; or
$R^4$ and $R^5$ taken together with the nitrogen to which they are attached form an optionally substituted monocyclic heterocyclyl ring;
$R^6$ is a leaving group;
W is independently selected from O, S, and Se; and
$B^1$ is an optionally protected heterocyclic base moiety;
or a salt thereof.

In one embodiment of formula (II), W is O.

In one embodiment of formula (II), $B^1$ is purine and pyrimidine. In another embodiment, $B^1$ is independently selected from Thy (thymine), BzCyt (4-benzoyl-cytosine), BzAde (6-benzoyl-adenine), AdeDMF (6-dimethylformamidino-adenine), iBuGua (2-isobutyryl-guanine), and GuaDMF (2-dimethylformamidino-guanine). In another embodiment, $B^1$ is selected from adenine, guanine, cytosine, thymine, and uracil.

In one embodiment of formula (II), $R^3$ is hydrogen.

In one embodiment of formula (II), $R^4$ and $R^5$ are methyl.

In one embodiment of formula (II), $R^1$ is hydrogen. In another embodiment, $R^1$ is an amino protecting group.

In one embodiment of formula (II), $R^6$ is halogen.

In one embodiment of formula (II), $R^1$ is an amino protecting group and $R^6$ is halogen.

In accordance with this invention, compounds are provided having formula (III):

(III)

wherein

R¹ is hydrogen or an amino protecting group;

R² is hydrogen, a hydroxyl protecting group, or solid support;

each R³ is independently selected from hydrogen, hydroxyl, and —O—R³ᵃ;

wherein each R³ᵃ is $C_{1-6}$ alkyl optionally substituted with —NR³ᵇR³ᶜ, imidazolyl, —(CH₂)ₐO(CH₂)ᵦNR³ᵇR³ᶜ, or —(CH₂)ₐONR³ᵈ(CH₂)ᵦNR³ᵇR³ᶜ;

wherein each R³ᵇ is hydrogen or $C_{1-2}$ alkyl;

each R³ᶜ is hydrogen or $C_{1-2}$ alkyl;

each R³ᵈ is hydrogen or $C_{1-2}$ alkyl;

each a is an integer selected from one to 4;

each b is an integer selected from one to 4;

each R⁴ is $C_{1-6}$ alkyl optionally substituted with —NR⁴ᵃR⁴ᵇ;

wherein R⁴ᵃ is hydrogen or $C_{1-2}$ alkyl and R⁴ᵇ is hydrogen or $C_{1-2}$ alkyl;

each R⁵ is $C_{1-6}$ alkyl optionally substituted with —NR⁵ᵃR⁵ᵇ;

wherein R⁵ᵃ is hydrogen or $C_{1-2}$ alkyl and R⁵ᵇ is hydrogen or $C_{1-2}$ alkyl; or R⁴ and R⁵ taken together with the nitrogen to which they are attached form an optionally substituted monocyclic heterocyclyl ring;

each W is independently selected from O, S, and Se; and each B¹ is independently selected from an optionally protected heterocyclic base moiety;

or a salt thereof.

In one embodiment of formula (III), W is O.

In one embodiment of formula (III), B¹ is independently selected from purine and pyrimidine. In another embodiment, each B¹ is independently selected from Thy (thymine), BzCyt (4-benzoyl-cytosine), BzAde (6-benzoyl-adenine), AdeDMF (6-dimethylformamidino-adenine), iBuGua (2-isobutyryl-guanine), and GuaDMF; (2-dimethylformamidino-guanine). In another embodiment, each B¹ is independently selected from adenine, guanine, cytosine, thymine, and uracil.

In one embodiment of formula (III), each R³ is hydrogen.

In one embodiment of formula (III), each R⁴ and each R⁵ are methyl.

In one embodiment of formula (III), R¹ is hydrogen. In another embodiment, R¹ is an amino protecting group.

In one embodiment of formula (III), R² is hydrogen. In another embodiment, R² is a hydroxyl protecting group or a solid support.

In one embodiment of formula (III), R¹ and R² are hydrogen. In another embodiment, R¹ is an amino protecting group and R² is a hydroxyl protecting group. In another embodiment, R¹ is an amino protecting group and R² is a solid support.

In accordance with this invention, compounds are provided as selected from the following:

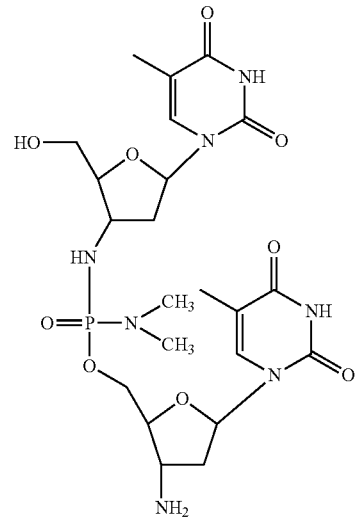

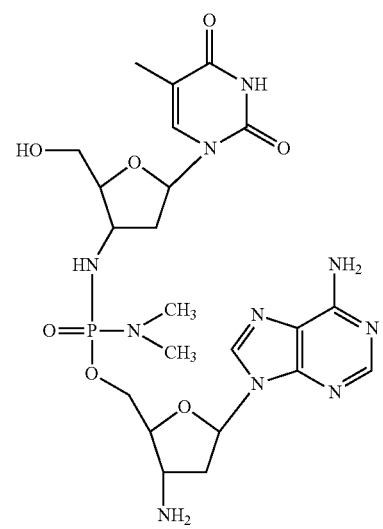

In accordance with this invention, compounds are provided as selected from the following:

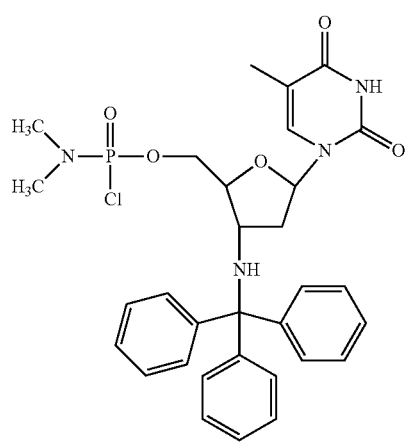

7
-continued
4
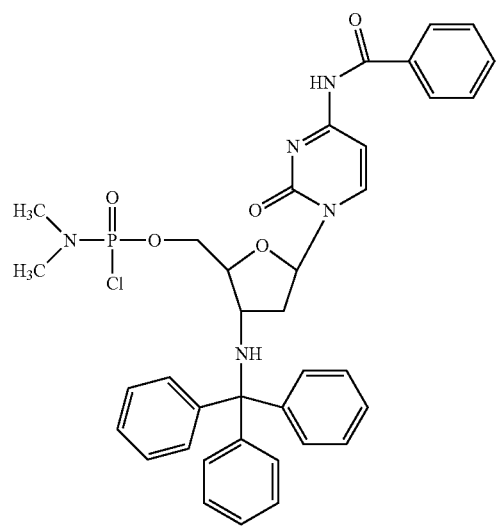
5
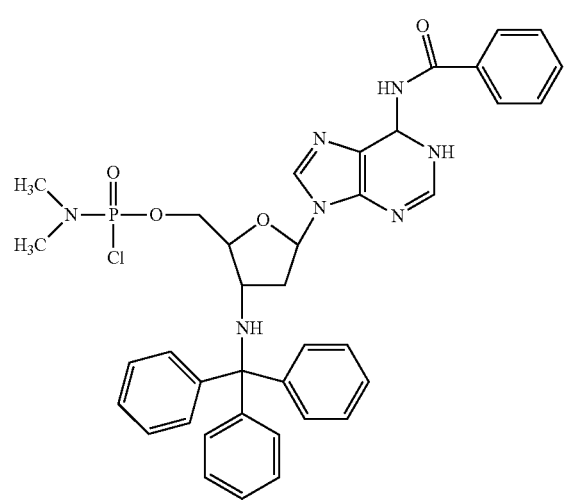
6
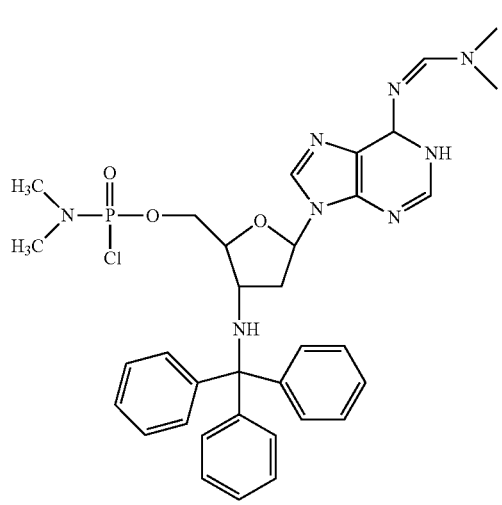
8
-continued
7
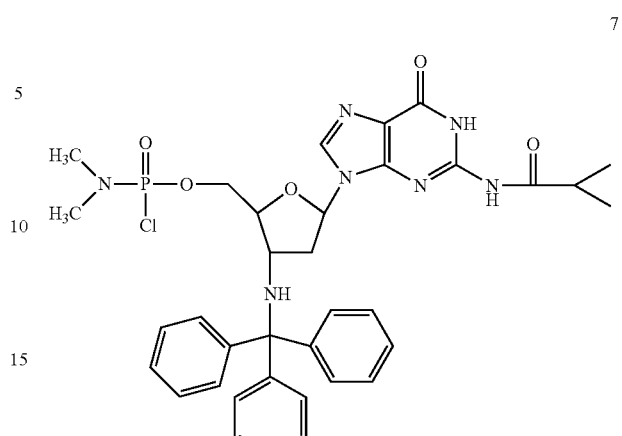
8
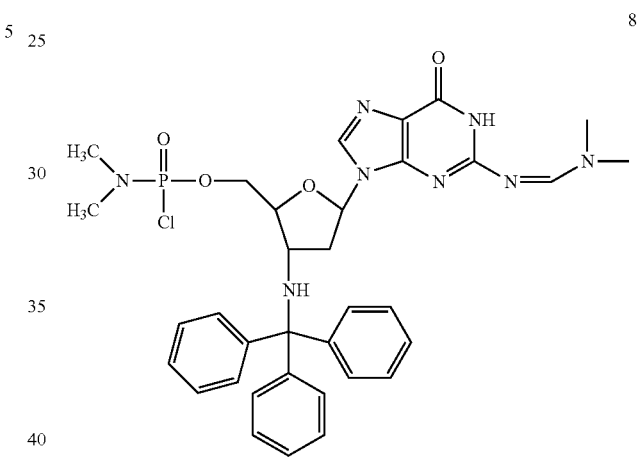
9
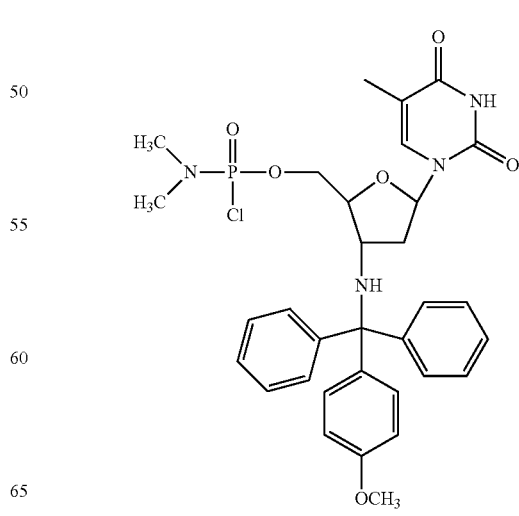

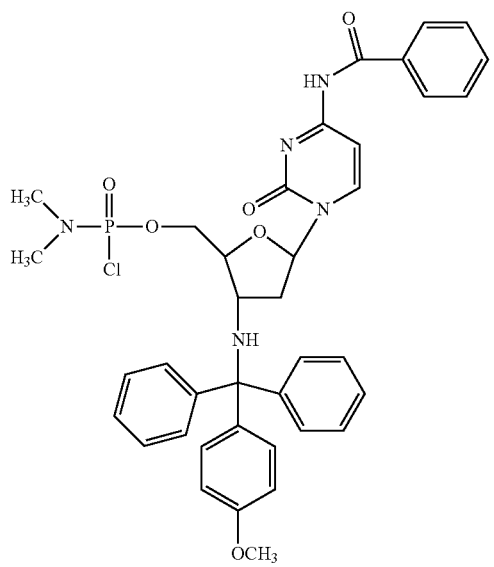
10
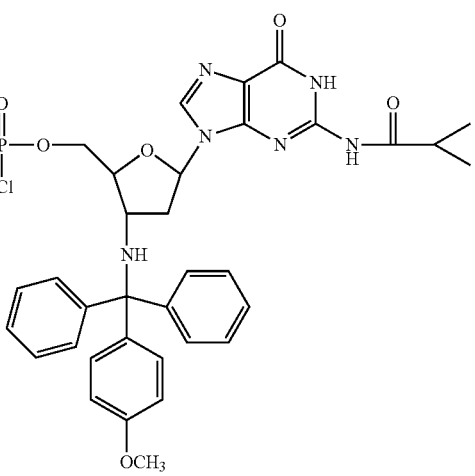
13
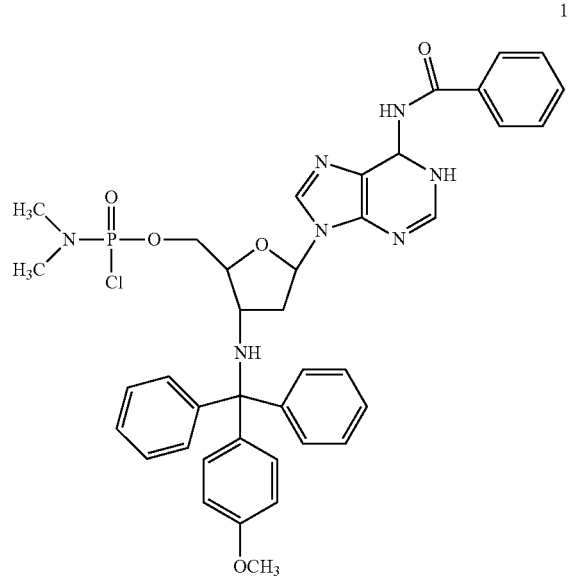
11
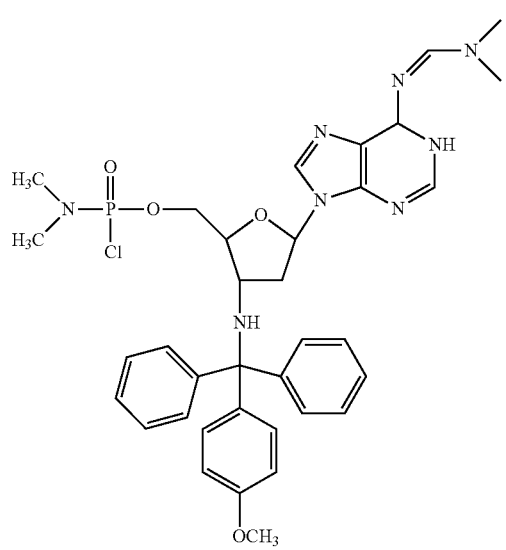
12
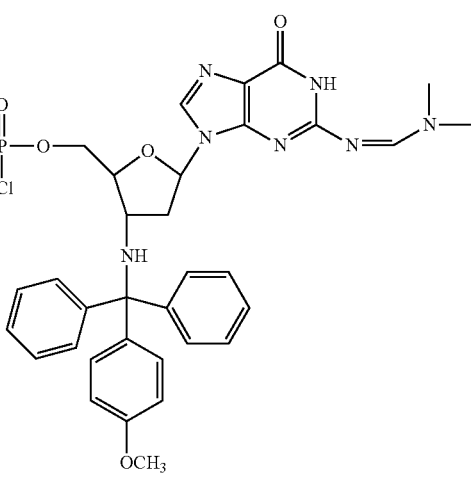
14
In accordance with this invention, there is provided an oligonucleotide, wherein the nucleoside subunits of the oligonucleotide are joined by intersubunit linkages, wherein at least one of the intersubunit linkages is a phosphorothioate or phosphate linkage, and wherein the oligonucleotide comprises a moiety of formula (IV)

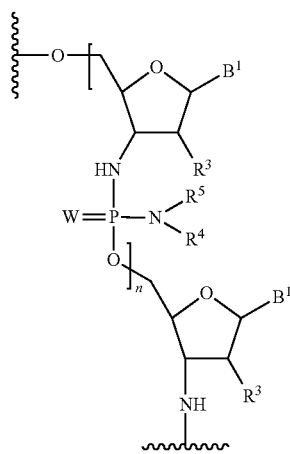

wherein
each $R^3$ is independently selected from hydrogen, hydroxyl, and —O—$R^{3a}$;
  wherein each $R^{3a}$ is $C_{1-6}$ alkyl optionally substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$;
  wherein each $R^{3b}$ is hydrogen or $C_{1-2}$ alkyl;
  each $R^{3c}$ is hydrogen or $C_{1-2}$ alkyl;
  each $R^{3d}$ is hydrogen or $C_{1-2}$ alkyl;
  each a is an integer selected from one to 4;
  each b is an integer selected from one to 4;
each $R^4$ is $C_{1-6}$ alkyl optionally substituted with —$NR^{4a}R^{4b}$;
  wherein $R^{4a}$ is hydrogen or $C_{1-2}$ alkyl and $R^{4b}$ is hydrogen or $C_{1-2}$ alkyl;
each $R^5$ is $C_{1-6}$ alkyl optionally substituted with —$NR^{5a}R^{5b}$;
  wherein $R^{5a}$ is hydrogen or $C_{1-2}$ alkyl and $R^{5b}$ is hydrogen or $C_{1-2}$ alkyl; or
$R^4$ and $R^5$ taken together with the nitrogen to which they are attached form an optionally substituted monocyclic heterocyclyl ring;
each W is independently selected from O, S, and Se;
each $B^1$ is independently selected from an optionally protected heterocyclic base moiety; and
n is an integer selected from one to 25;
or a salt thereof;
provided that if the oligonucleotide terminates at the 3' end or 5' end with the moiety of formula IV, the terminal group —O— or —NH— comprises a hydrogen to provide proper valence to the moiety of formula IV.

In one embodiment, intersubunit phosphorothioate or phosphate linkage is placed between two flanking regions of the moiety of formula (IV). In another embodiment, the intersubunit linkage between two flanking regions of the moiety of formula (IV) is phosphorothioate. In another embodiment, the intersubunit linkage between two flanking regions of the moiety of formula (IV) is phosphate.

In one embodiment,
a. the oligonucleotide comprises the moiety of formula (IV) located on the 5' end of the oligonucleotide;
b. the oligonucleotide comprises the moiety of formula (IV) located on the 3' end of the oligonucleotide; and
c. the oligonucleotide comprises 3 to 30 contiguous nucleotides linked by phosphorothioate or phosphate linkages located in between said moiety of formula (IV) located on the 5' end and said moiety of formula (IV) located on the 3' end of the oligonucleotide.

In one embodiment in the moiety of formula (IV), each W is O.

In one embodiment in the moiety of formula (IV), each $B^1$ is independently selected from purine and pyrimidine. In another embodiment, each $B^1$ is independently selected from Thy (thymine), BzCyt (4-benzoyl-cytosine), BzAde (6-benzoyl-adenine), AdeDMF (6-dimethylformamidino-adenine), iBuGua (2-isobutyryl-guanine), and GuaDMF (2-dimethylformamidino-guanine). In another embodiment, each $B^1$ is independently selected from adenine, guanine, cytosine, thymine, and uracil.

In one embodiment in the moiety of formula (IV), each $R^3$ is hydrogen.

In one embodiment in the moiety of formula (IV), each $R^4$ and each $R^5$ are methyl.

In one embodiment in the moiety of formula (IV), each n is an integer from one to 10.

In one embodiment, the oligonucleotide prevents translation of the mRNA by steric hindrance. In another embodiment, the oligonucleotide is a substrate for RNase-H-mediated degradation of the mRNA from a gene.

In one embodiment, the compound or oligonucleotide comprises a sequence which includes a region that is complementary to any portion of a sequence of a telomerase RNA (hTR) (SEQ ID NO: 1). In another embodiment, the compound or oligonucleotide comprises a sequence selected from the group consisting of: GTTAGGGTTAG (SEQ ID NO. 2); TAGGGTTAGACAA (SEQ ID NO. 3); and CAGTTAGGGTTAG (SEQ ID NO. 4). In another embodiments, the compound or oligonucleotide comprises a sequence of TAGGGTTAGACAA (SEQ ID NO. 3).

In accordance with this invention, there is provided a pharmaceutical composition comprising a compound or an oligonucleotide of the embodiments or a pharmaceutically acceptable salt thereof and a pharmaceutically acceptable carrier.

In accordance with this invention, there is provided a kit comprising a compound or an oligonucleotide of the embodiments, or a salt thereof.

In accordance with this invention, there is provided a method of preparing a compound of formula (II):

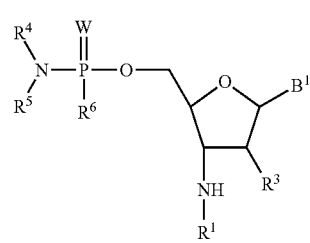

wherein
$R^1$ is hydrogen or an amino protecting group;
$R^3$ is independently selected from hydrogen, hydroxyl, and —O—$R^{3a}$;
  wherein $R^{3a}$ is $C_{1-6}$ alkyl optionally substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$;
  wherein $R^{3b}$ is hydrogen or $C_{1-2}$ alkyl;
  $R^{3c}$ is hydrogen or $C_{1-2}$ alkyl;
  $R^{3d}$ is hydrogen or $C_{1-2}$ alkyl;
  a is an integer selected from one to 4;
  b is an integer selected from one to 4;

R⁴ is C₁₋₆ alkyl optionally substituted with —NR⁴ᵃR⁴ᵇ;
  wherein R⁴ᵃ is hydrogen or C₁₋₂ alkyl and R⁴ᵇ is hydrogen or C₁₋₂ alkyl;
R⁵ is C₁₋₆ alkyl optionally substituted with —NR⁵ᵃR⁵ᵇ;
  wherein R⁵ᵃ is hydrogen or C₁₋₂ alkyl and R⁵ᵇ is hydrogen or C₁₋₂ alkyl; or
R⁴ and R⁵ taken together with the nitrogen to which they are attached form an optionally substituted monocyclic heterocyclyl ring;
R⁶ is a leaving group;
W is independently selected from O, S, and Se; and
B¹ is an optionally protected heterocyclic base moiety;
or a salt thereof;
wherein the method comprises:
  a) contacting a compound of formula (A)

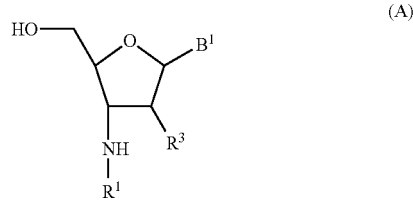

with a phosphorylating reagent.

In one embodiment, the phosphorylating reagent is dimethylamino-phosphoryl compound. In another embodiment, the phosphorylating reagent is dimethylamino-phosphorodichloridate. In another embodiment, R¹ is an amino protecting group.

In accordance with this invention, there is provided a method of preparing a compound of formula (I):

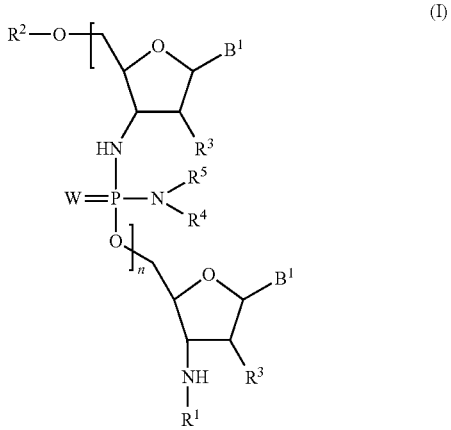

wherein
R¹ is hydrogen or an amino protecting group;
R² is hydrogen or a hydroxyl protecting group;
each R³ is independently selected from hydrogen, hydroxyl, and —O—R³ᵃ;
  wherein each R³ᵃ is C₁₋₆ alkyl optionally substituted with —NR³ᵇR³ᶜ, imidazolyl, —(CH₂)ₐO(CH₂)ᵦNR³ᵇR³ᶜ, or —(CH₂)ₐONR³ᵈ(CH₂)ᵦNR³ᵇR³ᶜ;
    wherein each R³ᵇ is hydrogen or C₁₋₂ alkyl;
    each R³ᶜ is hydrogen or C₁₋₂ alkyl;
    each R³ᵈ is hydrogen or C₁₋₂ alkyl;
    each a is an integer selected from one to 4;
    each b is an integer selected from one to 4;

each W is independently selected from O, S, and Se;
each B¹ is independently selected from an optionally protected heterocyclic base moiety;
each R⁴ is C₁₋₆ alkyl optionally substituted with —NR⁴ᵃR⁴ᵇ;
  wherein R⁴ᵃ is hydrogen or C₁₋₂ alkyl and R⁴ᵇ is hydrogen or C₁₋₂ alkyl;
each R⁵ is C₁₋₆ alkyl optionally substituted with —NR⁵ᵃR⁵ᵇ;
  wherein R⁵ᵃ is hydrogen or C₁₋₂ alkyl and R⁵ᵇ is hydrogen or C₁₋₂ alkyl; or
R⁴ and R⁵ taken together with the nitrogen to which they are attached form an optionally substituted monocyclic heterocyclyl ring; and
n is an integer selected from one to 50;
or a salt thereof;
wherein the method comprises:
  a) contacting a compound of formula (II)

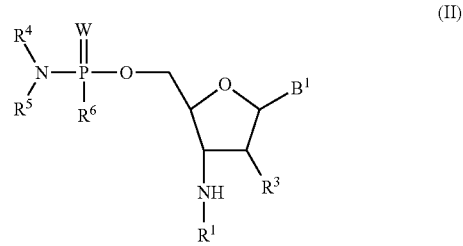

with a compound of formula (B):

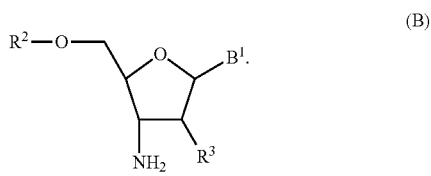

In one embodiment, the mixing is performed in presence of LiBr. In another embodiment, R¹ is an amino protecting group, and the method further comprises removing the amino protecting group. In another embodiment, R² is a hydroxyl protecting group, and the method further comprises removing the hydroxyl protecting group.

In accordance with this invention, there are provided methods for treatment and/or prevention of a cell proliferative disorder with use of the compounds and oligonucleotides disclosed herein.

In accordance with this invention, there are provided methods for inhibiting telomere elongation in a cell with use of the compounds and oligonucleotides disclosed herein.

In accordance with this invention, there are provided methods for shortening telomere length in a cell with use of the compounds and oligonucleotides disclosed herein.

In accordance with this invention, there are provided methods for effectively targeting and/or inhibiting non-coding RNA, with use of the compounds and oligonucleotides disclosed herein.

In accordance with this invention, there are provided methods for effectively acting as catalytic RNA, such as ribozyme, with use of the compounds and oligonucleotides disclosed herein.

DETAILED DESCRIPTION

The present disclosure provided herein discloses, inter alia, compositions and methods for the preparation and use of antisense oligonucleotides comprising at least one N3'→P5' phosphorodiamidate linkage (NPN) in the backbone.

The present disclosure provides, inter alia, antisense oligonucleotides that can effectively prevent or decrease protein expression as well as methods for using the same. The inventors have discovered, inter alia, antisense oligonucleotides comprising at least one phosphorodiamidate linkage in the backbone. With a phosphorodiamidate linkage, the antisense oligonucleotides disclosed herein may act as effective RNase H substrates, thus having the ability to cause RNAse H-mediated degradation of the mRNA that binds to the oligonucleotides. The anti-sense oligonucleotides provided herein can also act as steric blockers. The present disclosure provides for antisense oligonucleotides that can be effective by target degradation, occupancy-based inhibition (i.e. steric blocker), or a combination of both.

General Techniques

The practice of the invention will employ, unless otherwise indicated, conventional techniques in nucleic acid chemistry, molecular biology, microbiology, cell biology, biochemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994). Nucleic acids can be synthesized in vitro by well-known chemical synthesis techniques, as described in, e.g., Carruthers (1982) Cold Spring Harbor *Symp. Quant. Biol.* 47:411-418; Adams (1983) *J. Am. Chem. Soc.* 105:661; Belousov (1997) *Nucleic Acids Res.* 5 25:3440-3444; Frenkel (1995) *Free Radic. Biol. Med.* 19:373-380; Blommers (1994) *Biochemistry* 33:7886-7896; Narang (1979) *Meth. Enzymol.* 68:90; Brown (1979) *Meth. Enzymol.* 68:109; Beaucage (1981) *Tetra. Lett.* 22:1859; Komberg and Baker, *DNA Replication*, 2nd Ed. (Freeman, San Francisco, 1992); Scheit, *Nucleotide Analogs* (John Wiley, New York, 1980); Uhlmann and Peyman, *Chemical Reviews*, 90:543-584, 1990.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, 4$^{th}$ edition, New York: Oxford University Press, 2002, pp. 360-361, 1084-1085; Smith and March, March's Advanced Organic Chemistry: Reactions, Mechanisms, and Structure, 5$^{th}$ edition, Wiley-Interscience, 2001.

Terms

The following terms have the following meanings unless otherwise indicated. Any undefined terms have their art recognized meanings.

The term "$C_{1-n}$alkyl," as used herein, pertains to a monovalent moiety obtained by removing a hydrogen atom from a $C_{1-n}$hydrocarbon compound having from 1 to n carbon atoms, which may be aliphatic or alicyclic, or a combination thereof, and which may be saturated, partially unsaturated, or fully unsaturated, wherein n is a number greater than one. Likewise, the term "$C_{1-20}$alkyl," as used herein, pertains to a monovalent moiety obtained by removing a hydrogen atom from a $C_{1-20}$hydrocarbon compound having from 1 to 20 carbon atoms, which may be aliphatic or alicyclic, or a combination thereof, and which may be saturated, partially unsaturated, or fully unsaturated.

The term "aryl" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring.

The term "heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties.

Examples of heteroaryls include, but are not limited to, pyrrole, imidazole, pyrazole, pyridine, pyrazine, pyrimidine, pyridazine, indolizine, isoindole, indole, purine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, piperidine, piperazine, phthalimide, 4,5,6,7-tetrahydrobenzo[b]thiophene, thiazole, thiophene, benzo[b]thiophene, and the like.

The term "cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The terms "heterocycle," "heterocyclic," "heterocycloalkyl" or "heterocyclyl" refers to a saturated or partially unsaturated group having a single ring or multiple condensed rings, including fused, bridged, or spiro ring systems, and having from 3 to 20 ring atoms, including 1 to 10 hetero atoms. These ring atoms are selected from the group consisting of carbon, nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for N-oxide, —S(O)—, or —SO$_2$— moieties.

Examples of heterocycles include, but are not limited to, azetidine, dihydroindole, indazole, quinolizine, imidazolidine, imidazoline, piperidine, piperazine, indoline, 1,2,3,4-tetrahydroisoquinoline, thiazolidine, morpholinyl, thiomorpholinyl (also referred to as thiamorpholinyl), 1,1-dioxothiomorpholinyl, piperidinyl, pyrrolidine, tetrahydrofuranyl, and the like.

Where an aryl, cycloalkyl, heteroaryl, or heterocyclyl group is "substituted," unless otherwise constrained by the definition for the aryl, cycloalkyl, heteroaryl, or heterocyclyl substituent, such aryl, cycloalkyl, heteroaryl, or heterocyclyl groups can be substituted with 1 to 5, or from 1 to 3 substituents, selected from alkyl, substituted alkyl, alkenyl, substituted alkenyl, alkynyl, substituted alkynyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, azido, cyano, halogen, hydroxyl, oxo, oxyacylamino, thioketo, carboxyl, carboxyl ester, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, sulfonylamino, —SO-alkyl, —SO-substituted alkyl, —SO-aryl, —SO-heteroaryl, —SO— heterocyclyl, —$SO_2$-alkyl, —$SO_2$-substituted alkyl, —$SO_2$-aryl, —$SO_2$-heteroaryl, —$SO_2$-heterocyclyl, trihalomethyl, spermine, and spermidine.

The term "amino protecting group" refers to a group commonly employed to keep (i.e., to "block" or "protect") an amino group from reacting with a reagent while it reacts with an intended target functional group of a molecule. Representative protecting groups are disclosed in Greene and Wuts, Protective Groups in Organic Synthesis, Chapter 7, $3^{rd}$ ed., John Wiley & Sons, New York, 1999. Examples of amino protecting groups include, but are not limited to isobutyryl, dialkylformamidino (e.g., dimethylformamidino and diethylformamidino), diarylformamidino (e.g., diphenylformamidino), t-butoxycarbonyl, trityl, benzyloxycarbonyl, 9-fluorenylmethoxycarbonyl, formyl, tert-allyloxycarbonyl (Alloc), 9-fluorenylmethyl (Fm), methoxycarbonyl, ethoxycarbonyl, benzyl (Bn), 2,2,4,6,7-pentamethyldihydrobenzofuran-5-sulfonyl (Pbf), acetyl, benzoyl, $C_6H_5$—$SO_2$—, 4-$NO_2C_6H_4$—$SO_2$—, 2-$NO_2C_6H_4$—$SO_2$—, and 2,4-$(NO_2)_2C_6H_3$—$SO_2$—. In some instances, the amino protecting group is an acid labile protecting group. In some instances, the amino protecting group is a base labile protecting group.

The term "hydroxyl protecting group" refers to a group commonly employed to keep (i.e., to "block" or "protect") a hydroxyl group from reacting with a reagent while it reacts with an intended target functional group of a molecule. Representative protecting groups are disclosed in Greene and Wuts, Protective Groups in Organic Synthesis, Chapter 2, $3^{rd}$ ed., John Wiley & Sons, New York, 1999. Examples of hydroxyl protecting groups include, but are not limited to acetyl, t-butyl, t-butoxymethyl, hydroxymethyl, methoxymethyl, tetrahydropyranyl, 1-ethoxyethyl, 1-(2-chloroethoxy) ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, trityl, monomethoxytrityl, dimethoxytrityl, 9-phenylxanthine-9-yl (Pixyl) or 9-(p-methoxyphenyl)xanthine-9-yl (MOX). In some instances, the hydroxyl protecting group is an acid labile protecting group. In some instances, the hydroxyl protecting group is a base labile protecting group.

The term "acid labile protecting group" refers to a group commonly employed to keep (i.e., to "block" or "protect") a functional group from reacting with a reagent while it reacts with an intended target functional group of a molecule and can be removed in the presence of an acid.

The term "base labile protecting group" refers to a group commonly employed to keep (i.e., to "block" or "protect") a functional group from reacting with a reagent while it reacts with an intended target functional group of a molecule and can be removed in the presence of a base.

The term "leaving group" is a group that is subject to nucleophilic displacement. Suitable leaving groups are well known in the art, e.g., see, "Advanced Organic Chemistry," Jerry March, $5^{th}$ Ed., pp. 351-357, John Wiley and Sons, N.Y. Examples of leaving groups include chloro, iodo, bromo, fluoro, methanesulfonyloxy (mesyloxy), tosyloxy, triflyloxy, nitro-phenylsulfonyloxy (nosyloxy), bromo-phenylsulfonyloxy (brosyloxy), triazolyl, benzotriazolyl, hydroxybenzotriazolyl ester, and 1-(mesitylene-2-sulfonyl)-3-nitro-1H-1,2,4-triazole (MSNT). In some instances, a leaving group is a halogen, such as chloro, bromo, or iodo.

The term "nucleoside" refers to a moiety having the general structure represented below, where B represents a nucleobase and the 2' carbon can be substituted as described below. When incorporated into an oligomer or polymer, the 3' carbon is further linked to an oxygen or nitrogen atom.

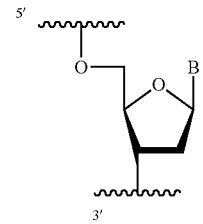

This structure includes 2'-deoxy and 2'-hydroxyl (i.e. deoxyribose and ribose) forms, and analogs. Less commonly, a 5'-NH group can be substituted for the 5'-oxygen. "Analogs", in reference to nucleosides, includes synthetic nucleosides having modified nucleobase moieties (see definition of "nucleobase" below) and/or modified sugar moieties, such as 2'-fluoro sugars, and further analogs. Such analogs are typically designed to affect binding properties, e.g., stability, specificity, or the like.

The term "nucleobase" (or "base") includes (i) native DNA and RNA nucleobases (uracil, thymine, adenine, guanine, and cytosine), (ii) modified nucleobases or nucleobase analogs (for example, but not limited to, 5-methylcytosine, 5-bromouracil, or inosine) and (iii) nucleobase analogs. A "nucleobase analog" is a compound whose molecular structure is similar that of a typical DNA or RNA nucleobase.

The terms "unmodified nucleobase" and "naturally occurring nucleobase" include the purine bases adenine (A) and guanine (G), and the pyrimidine bases thymine (T), cytosine (C) and uracil (U).

Examples of modified nucleobases include other synthetic and natural nucleobases such as BzCyt (4-benzoyl-cytosine), BzAde (6-benzoyl-adenine), AdeDMF 6-dimethylformamidino-adenine), iBuGua (2-isobutyryl-guanine), GuaDMF (2-dimethylformamidino-guanine), thioguanine, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein.

The term "heterocyclic base moiety" refers to the base portion of the nucleoside. The two most common classes of such heterocyclic bases are purines and pyrimidines. The term "heterocyclic base moiety" as used herein, includes unmodified or naturally occurring nucleobases, modified or non-naturally occurring nucleobases as well as synthetic mimetics thereof. In general, a heterocyclic base moiety is heterocyclic system that contains one or more atoms or groups of atoms capable of hydrogen bonding to a base of a nucleic acid. Heterocyclic base moiety includes protected forms and deprotected forms.

A "polynucleoside," "oligonucleoside," "polynucleotide," or "oligonucleotide" can be used interchangeably herein to refer to an oligomer or polymer of the above-referenced nucleoside moieties, having between about 6 and about 100 such moieties, joined by specific intersubunit linkages between their 5' and 3' positions. These terms "oligonucleotide" and "oligonucleoside" also include such polymers or oligomers having modifications, known to one skilled in the art, to the sugar (e.g., 2' substitutions), the base (see the definition of "nucleobase" below), as well as the 3' and 5' termini.

The term "intersubunit linkage" refers to a linkage between the 5' oxygen and 3' carbon in the structure above. Such linkages can be the same or different within a molecule.

The term "internucleotide linkage" refers to a phosphorus-based linkage between the 5' oxygen and 3' carbon in the structure above, with phosphorus linking the 5' oxygen and to a nitrogen or oxygen atom on the 3' carbon. Such linkages can be the same or different within a molecule.

An "NPN linkage" in the compounds of the embodiments is the group 3'-NH—P(=W)(NRR)-5',

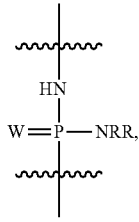

wherein W and R are defined herein. An "NPN linkage" is shown, for example, in formula (I).

The term "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, appended to, or if appropriate, fused to, a parent group.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "RNA target" refers to an RNA transcript to which an antisense oligonucleotide binds in a sequence specific manner.

The term "RNAse H-mediated degradation" refers to the specific cleavage of the 3'-O—P bond of an RNA in a DNA/RNA duplex to produce 3'-hydroxyl and 5'-phosphate terminated products by the nonspecific endogenous cellular ribonuclease RNAse H.

The term "gapmer" refers to an oligonucleotide comprising two flanking regions (the "5' flanking region" and the "3' flanking region") and a central region (a "gap"), wherein the 5' and the 3' flanking regions comprise at least one modification difference compared to the gap region. Such modifications include monomeric linkage and sugar modifications as well as the absence of modification (unmodified RNA or DNA). Thus, in certain embodiments, the nucleotide linkages in each of the 5' and 3' flanking regions are different than the nucleotide linkages in the gap. In certain embodiments, the modifications in the 5' and 3' flanking regions are the same as one another. In certain embodiments, the modifications in the 5' and 3' flanking regions are different from each other. In certain embodiments, nucleotides in the gap are unmodified and nucleotides in the 5' and 3' flanking regions are modified. In certain embodiments, the modification(s) within each 5' and 3' flanking regions are the same. In certain embodiments, the modification(s) in one of the 5' or 3' flanking regions are different from the modification(s) in the other flanking region. In some embodiments, gapmer oligonucleotide hybridization to a target mRNA molecule, results in the RNAse H-mediated degradation of the target mRNA molecule.

As used herein, an antisense oligonucleotide that prevents target mRNA translation by "steric hindrance" is an oligonucleotide that interferes with gene expression or other mRNA-dependent cellular processes (for example, mRNA splicing or initiation of translation at the level of the ribosome) by binding to a target mRNA. Such an oligonucleotide may or may not be RNase-H independent in functionality.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent and preferably stop) cancer cell infiltration into peripheral organs; inhibit (i.e., slow to some extent and preferably stop) tumor metastasis; inhibiting, to some extent, tumor growth; and/or relieving to some extent one or more of the symptoms associated with the disorder. An effective dosage can be administered in one or more administrations. For purposes of the present disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during or after administration of the other treatment modality to the individual.

As used herein, "treatment" or "treating" is an approach for obtaining beneficial or desired results including and preferably clinical results. For purposes of the present disclosure, beneficial or desired clinical results include, but are not limited to, one or more of the following: reducing the proliferation of (or destroying) cancerous cells, decreasing symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, treatment may include having an effect in reducing the number of cancer cells; reducing the tumor size; inhibiting (i.e., slow to some extent and preferably stop) cancer cell infiltration into peripheral organs; inhibit (i.e., slow to some extent and preferably stop) tumor metastasis; inhibiting, to some extent, tumor growth; and/or relieving to some extent one or more of the symptoms associated with the disorder.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

An "individual" or a "subject" or a "patient" is a mammal. Mammals also include, but are not limited to, farm animals, sport animals, pets (such as cats, dogs, horses), primates, mice and rats. In some embodiments, an individual is a human.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

Reference to "about" a value or parameter herein includes (and describes) embodiments that are directed to that value or parameter per se. For example, description referring to "about X" includes description of "X."

It is understood that aspect and variations of the invention described herein include "consisting" and/or "consisting essentially of" aspects and variations.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The nomenclature used herein to name the subject compounds is illustrated in the Examples herein. This nomenclature has generally been derived using the commercially-available AutoNom software.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

Antisense Oligonucleotides

The principle underlying antisense technology lies in the ability of an antisense oligonucleotide to hybridize to a target nucleic acid and modulate gene expression, such as by affecting transcription, translation, or splicing. This modulation of gene expression can specifically be achieved by, for example, target degradation, occupancy-based inhibition (i.e. sterics), or a combination of both. An example of modulation of mRNA target function by degradation is RNase H-based degradation of the target mRNA upon hybridization with a DNA-like antisense compound. Another example is interference with mRNA translation due to steric hindrance. This sequence-specificity makes antisense oligonucleotides attractive as therapeutics to selectively modulate the expression of genes involved in the pathogenesis of any one of a variety of diseases (such as cell proliferative disorders). Antisense technology is an effective means for reducing the expression of one or more specific gene products and can therefore prove to be uniquely useful in a number of therapeutic applications. The present disclosure provides for antisense oligonucleotides that can be effective by target degradation, occupancy-based inhibition (i.e. steric blocker), or a combination of both.

For oligonucleotides that prevent target mRNA translation via a steric-blocking mechanism, oligonucleotide-target mRNA heteroduplex formation does not lead to RNA turnover (as is the case with RNAse-H mediated degradation), but results instead in the hindrance of RNA processing, nucleocytoplasmic transport or translation of the mRNA itself at the level of the ribosome. This is particularly the case when the antisense oligonucleotide is targeted to the translation initiation region of the target mRNA (i.e. the region on and surrounding the START codon).

RNase H-dependent oligonucleotides have advantages over steric blocking oligonucleotides. Advantages include the use of a small amount of oligonucleotide for RNase H-dependent mechanism compared to stoichiometric amount of oligonucleotide for steric blocking mechanism. The amount of RNase H-dependent oligonucleotide is catalytic because the RNase H-dependent oligonucleotide is not cleaved by RNase H when bound to mRNA, but is released and is available for binding a new copy of mRNA and inducing cleavage of the new copy of mRNA by RANase H (i.e. recycled back).

Using N3'→P5' phosphorodiamidate (NPN) backbone homogeneously or heterogeneously can reduce the charge on an oligonucleotide. The entire oligonucleotide can contain the NPN backbone or there can be a mix of NPN backbone with a backbone of natural intersubunit linkages (phosphate) or the modified backbones or non-natural intersubunit linkages. When mixed, the NPN backbone can flank the backbone of natural intersubunit linkages (phosphate) or the modified backbones or non-natural intersubunit linkages. In certain embodiments, there can be a mix of NPN backbone within a phosphorothioate backbone.

In certain embodiments, the compound comprises about 35-100% of the backbone that is NPN linkage. In certain embodiments, the compound comprises NPN linkage that is about 35, 40, 45, 50, 55, 60, 65, 70, 75, 80, 85, 90, 95, or 100% of the backbone.

Antisense to Coding mRNA

The sequence of any of the antisense oligonucleotides disclosed herein can be, but need not necessarily be, 100% complementary to an mRNA from a specific gene to be specifically hybridizable. In one embodiment, the antisense oligonucleotides of the present embodiments comprise at least 70%, or at least 75%, or at least 80%, or at least 85% sequence complementarity to an mRNA from a specific gene. In other embodiments, the antisense oligonucleotides of the present embodiments comprise at least 90% sequence complementarity and even comprise at least 95% or at least 99% sequence complementarity to an mRNA from a specific gene to which they are targeted. For example, an antisense oligonucleotide in which 18 of 20 nucleobases of the antisense oligonucleotide are complementary to an mRNA from a specific gene, would specifically hybridize and would represent 90 percent complementarity. In this example, the remaining noncomplementary nucleobases can be clustered or interspersed with complementary nucleobases and need not be contiguous to each other or to complementary nucleobases. Percent complementarity of an antisense compound with a region of a target nucleic acid can be determined routinely using BLAST programs (basic local alignment search tools) and PowerBLAST programs known in the art (Altschul et al., *J. Mol. Biol,* 1990, 215, 403-410; Zhang & Madden, *Genome Res.,* 1997, 7, 649-656).

In some aspects of any of the antisense oligonucleotides disclosed herein, the oligonucleotide is from about any of 6, 7, 8, 9, 10, 11, 12, 13, 14, 15, 16, 17, 18, 19, 20, 21, 22, 23, 24, or 25 nucleotides in length, up to any of 25, or 30, or 50, or 100 nucleotides in length. In another embodiment, the oligonucleotide comprises 6, 7, 8, 9, 10, 11, 12, 13, 14, 15, 16, 17, 18, 19, 20, 21, 22, 23, 24, or 25 nucleotides in length.

In other embodiments of any of the antisense oligonucleotides disclosed herein, the oligonucleotide is complementary (such as at least 80%, 85%, 90%, 91%, 92%, 93%, 94%, 95%, 96%, 97%, 98%, 99%, or 100%, including any percentages in between these values, complementary) to an mRNA from a specific gene at the site of the mRNA's translation initiation region. In other embodiments of any of the antisense oligonucleotides disclosed herein, the oligonucleotide is complementary (such as at least 80%, 85%, 90%, 91%, 92%, 93%, 94%, 95%, 96%, 97%, 98%, 99%, or 100%, including any percentages in between these values, complementary) to an mRNA from a specific gene at a site on the mRNA where two exons are spliced together.

Provided herein are antisense oligonucleotides having specific intersubunit linkages wherein the oligonucleotides effectively decrease or prevent specific protein expression. In some aspects, the antisense oligonucleotides decrease or prevent translation of an mRNA from a specific gene by steric hindrance. In other aspects, the antisense oligonucleotides decrease or prevent translation of an mRNA from a specific gene by RNase-H-mediated degradation of the mRNA from a specific gene. In yet other aspects, the antisense oligonucleotides decrease or prevent translation of an mRNA from a specific gene by steric hindrance and/or by RNase-H-mediated degradation of the mRNA from a specific gene. In some embodiments, contacting any of the oligonucleotides disclosed herein with a cell decreases relative protein expression of a specific gene in the cell by greater than at least about 35% (such as at least about 40%, 45%, 50%, 55%, 60%, 70%, 75%, 80%, 85%, 90%, 95%, or 100%, inclusive, including any percentages in between these values) in comparison to cells that have not been contacted with the oligonucleotide. In some embodiments, contacting any of the oligonucleotides disclosed herein with a cell decreases relative protein expression of a specific gene in the cell by greater than at least about 35%-45%, 40%-50%, 45%-55%, 50%-60%, 55%-65%, 60%-70%, 65%-75%, 70%-80%, 75%-85%, 80%-90%, 85%-95%, or 90%-100% in comparison to cells that have not been contacted with the oligonucleotide.

Methods known in the art can be used to determine whether an antisense oligonucleotide is effective in preventing or decreasing expression of a specific protein in a cell. These include, without limitation, methods to assess mRNA such as reverse transcription-quantitative PCT (RT-qPCR), Northern Blot, in situ hybridization, microarray, serial analysis of gene expression (SAGE), or RNA-Seq. Also included are common methods known in the art to assess certain protein levels in cells such as, but not limited to, Western Blot, immunohistochemistry, enzyme-linked immunosorbant assay (ELISA), radioimmunoassay (RIA), or 2D gel electrophoresis followed by quantitative mass spectrometry.

Antisense to Non-Coding RNA

The present disclosure provides antisense oligonucleotides that can effectively target non-coding-+RNA, such as microRNA. A microRNA (miRNA) is a small non-coding RNA molecule found in plants and animals, which functions in transcriptional and post-transcriptional regulation of gene expression. As modulators of small non-coding RNA function, the compositions of the embodiments find utility in the control and manipulation of cellular functions or processes such as regulation of splicing, chromosome packaging or methylation, control of developmental timing events, increase or decrease of target RNA expression levels depending on the timing of delivery into the specific biological pathway and translational or transcriptional control. In addition, the compositions of the embodiments can be modified in order to optimize their effects in certain cellular compartments, such as the cytoplasm, nucleus, nucleolus or mitochondria.

Ribozymes

The present disclosure provides antisense oligonucleotides that can effectively act as ribozymes. Ribozymes are RNA molecules that are capable of performing specific biochemical reactions, similar to the action of protein enzymes. In certain embodiments, ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach, Nature, 334:585-591, 1988)) can be used to catalytically cleave mRNA transcripts to thereby inhibit translation of the protein encoded by the mRNA. Methods of designing and producing ribozymes are known in the art (see, e.g., Scanlon, 1999, Therapeutic Applications of Ribozymes, Humana Press). A ribozyme having specificity for a certain gene can be designed based upon the nucleotide sequence.

Compounds

Formula I

The present disclosure provides a compound of formula (I):

wherein
$R^1$ is hydrogen, an amino protecting group, or an oligonucleotide;
$R^2$ is hydrogen, a hydroxyl protecting group, solid support, or an oligonucleotide;
each $R^3$ is independently selected from hydrogen, hydroxyl, and $-O-R^{3a}$;
wherein each $R^{3a}$ is $C_{1-6}$ alkyl optionally substituted with $-NR^{3b}R^{3c}$, imidazolyl, $-(CH_2)_aO(CH_2)_bNR^{3b}R^{3c}$, or $-(CH_2)_aONR^{3d}(CH_2)_bNR^{3b}R^{3c}$;
wherein each $R^{3b}$ is hydrogen or $C_{1-2}$ alkyl;
each $R^{3c}$ is hydrogen or $C_{1-2}$ alkyl;
each $R^{3d}$ is hydrogen or $C_{1-2}$ alkyl;
each a is an integer selected from one to 4;
each b is an integer selected from one to 4;
each $R^4$ is $C_{1-6}$ alkyl optionally substituted with $-NR^{4a}R^{4b}$;
wherein $R^{4a}$ is hydrogen or $C_{1-2}$ alkyl and $R^{4b}$ is hydrogen or $C_{1-2}$ alkyl;
each $R^5$ is $C_{1-6}$ alkyl optionally substituted with $-NR^{5a}R^{5b}$;
wherein $R^{5a}$ is hydrogen or $C_{1-2}$ alkyl and $R^{5b}$ is hydrogen or $C_{1-2}$ alkyl; or
$R^4$ and $R^5$ taken together with the nitrogen to which they are attached form an optionally substituted monocyclic heterocyclyl ring;
each W is independently selected from O, S, and Se;
each $B^1$ is independently selected from an optionally protected heterocyclic base moiety; and
n is an integer selected from one to 50;
or a salt thereof In certain embodiments of formula (I), $R^1$ is hydrogen.

In certain embodiments, $R^1$ is an amino protecting group. Examples of suitable amino protecting group include trityl, dimethoxytrityl, and methoxytrityl. In certain embodiments, $R^1$ is trityl. In certain embodiments, $R^1$ is methoxytrityl.

In certain embodiments, $R^1$ is an oligonucleotide. The oligonucleotide can comprise one to 50 nucleosides. In certain embodiments, the oligonucleotide is about 1 to about 25 nucleotides, or about 1 to about 20 nucleotides in length, or about 1 to about 10 nucleotides in length. In certain embodiments, the oligonucleotide is about 1, 2, 3, 4, 5, 6, 7, 8, 9, 10, 11, 12, 13, 14, 15, 16, 17, 18, 19, 20, 21, 22, 23, 24, 25, 30, 35, 40, 45, or 50 nucleotides.

The intersubunit linkages of the oligonucleotide can be same or different. The intersubunit linkages of the oligonucleotide can be selected from phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thiophosphoramidates, thionoalkylphosphonates, thionoalkylphosphotriesters, thiophosphates, selenophosphates and boranophosphates having normal 3'-5' linkages, 2'-5' linked analogs of these, and those having inverted polarity wherein one or more intersubunit linkages is a 3' to 3', 5' to 5' or 2' to 2' linkage. In certain embodiments, the intersubunit linkage is phosphate or phosphorothioate.

In certain embodiments, each $R^1$ is not wherein W is O, S, or Se; X is OH or SH; and Z is OH, SH, $CH_3$, or $OC_2H_5$.

In certain embodiments of formula (I), $R^2$ is hydrogen.

In certain embodiments, $R^2$ is a solid support. Suitable solid supports can be made out of glass or polymers. For example, suitable solid supports can be made out of polystyrene (such as polystyrene crosslinked with divinylbenzene), controlled pore glass (CPG), or TentaGel® (Sigma-Aldrich, St. Louis, Mo.). Suitable solid supports include, but are not limited to, slides, beads, chips, particles, strands, gels, sheets, tubing, spheres, containers, capillaries, pads, slices, films, plates and the like. In certain embodiments, a solid support may be biological, nonbiological, organic, inorganic, or any combination thereof.

In certain embodiments, $R^2$ is a hydroxyl protecting group. Examples of suitable hydroxyl protecting group include tert-butyl-dimethylsilyl, methoxymethyl, tetrahydropyranyl, tert-butyl, benzyl, and tert-butyldiphenylsilyl. In certain embodiments, $R^2$ is tert-butyl-dimethylsilyl.

In certain embodiments, $R^2$ is an oligonucleotide. The oligonucleotide can comprise one to 50 nucleosides. In certain embodiments, the oligonucleotide is about 1 to about 25 nucleotides, or about 1 to about 20 nucleotides in length, or about 1 to about 10 nucleotides in length. In certain embodiments, the oligonucleotide is about 1, 2, 3, 4, 5, 6, 7, 8, 9, 10, 11, 12, 13, 14, 15, 16, 17, 18, 19, 20, 21, 22, 23, 24, 25, 30, 35, 40, 45, or 50 nucleotides.

The intersubunit linkages of the oligonucleotide can be the same or different. The intersubunit linkages of the oligonucleotide can be selected from phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thiophosphoramidates, thionoalkylphosphonates, thionoalkylphosphotriesters, thiophosphates, selenophosphates and boranophosphates having normal 3'-5' linkages, 2'-5' linked analogs of these, and those having inverted polarity wherein one or more intersubunit linkages is a 3' to 3', 5' to 5' or 2' to 2' linkage. In certain embodiments, the intersubunit linkage is phosphate or phosphorothioate.

In certain instances, $R^1$ and $R^2$ are hydrogen. In certain instances, $R^1$ is hydrogen and $R^2$ is a hydroxyl protecting group. In certain instances, $R^1$ is an amino protecting group and $R^2$ is hydrogen. In certain instances, $R^1$ is an amino protecting group and $R^2$ is a solid support. In certain instances, $R^1$ is an amino protecting group and $R^2$ is a hydroxyl protecting group.

In formula (I), each $R^3$ is independently selected from hydrogen, hydroxyl, and —O—$R^{3a}$; wherein each $R^{3a}$ is $C_{1-6}$ alkyl optionally substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$.

In certain embodiments, each $R^3$ is hydrogen. In certain embodiments, each $R^3$ is hydroxyl. In certain embodiments, each $R^3$ is —O—$R^{3a}$. In certain instances, at least one $R^3$ is —O—$R^{3a}$.

In certain embodiments, at least one $R^{3a}$ is $C_{1-6}$ alkyl, such as methyl, ethyl, or propyl. In certain embodiments, at least one $R^{3a}$ is $C_{1-6}$ alkyl substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$.

In certain embodiments, $R^{3b}$ is hydrogen. In certain embodiments, $R^{3b}$ is methyl or ethyl. In certain embodiments, $R^{3c}$ is hydrogen. In certain embodiments, $R^{3c}$ is methyl or ethyl. In certain embodiments, $R^{3d}$ is hydrogen. In certain embodiments, $R^{3d}$ is methyl or ethyl.

In certain embodiments, a is one. In certain embodiments, a is 2. In certain embodiments, a is 3. In certain embodiments, a is 4.

In certain embodiments, b is one. In certain embodiments, b is 2. In certain embodiments, b is 3. In certain embodiments, b is 4.

In certain embodiments of formula (I), each $R^4$ is $C_{1-6}$ alkyl optionally substituted with —$NR^{4a}R^{4b}$; wherein $R^{4a}$ is hydrogen or $C_{1-2}$ alkyl and $R^{4b}$ is hydrogen or $C_{1-2}$ alkyl. In certain embodiments, each $R^4$ is $C_{1-6}$ alkyl, such as methyl, ethyl, or propyl. In certain embodiments, each $R^4$ is methyl. In certain embodiments, each $R^4$ is ethyl.

In certain embodiments of formula (I), each $R^5$ is $C_{1-6}$ alkyl optionally substituted with —$NR^{5a}R^{5b}$; wherein $R^{5a}$ is hydrogen or $C_{1-2}$ alkyl and $R^{5b}$ is hydrogen or $C_{1-2}$ alkyl. In certain embodiments, each $R^5$ is $C_{1-6}$ alkyl, such as methyl, ethyl, or propyl. In certain embodiments, each $R^5$ is methyl. In certain embodiments, each $R^5$ is ethyl.

In certain embodiments of formula (I), $R^4$ and $R^5$ taken together with the nitrogen to which they are attached form an optionally substituted monocyclic heterocyclyl ring. In certain instances, the optionally substituted monocyclic heterocyclyl ring is a 4-8 membered ring, such as 4, 5, 6, 7, or 8-membered ring. In certain instances, the optionally substituted monocyclic heterocyclyl ring, including the nitrogen to which $R^4$ and $R^5$ are attached, comprises 1, 2, or 3 heteroatoms. In certain instances, the optionally substituted monocyclic heterocyclyl ring, including the nitrogen to which $R^4$ and $R^5$ are attached, comprises 1, 2, or 3 heteroatoms selected from nitrogen, oxygen, and sulfur. In certain instances, the optionally substituted monocyclic heterocyclyl ring, including the nitrogen to which $R^4$ and $R^5$ are attached, is a 6-membered ring comprising one nitrogen. In certain instances, the optionally substituted monocyclic heterocyclyl ring, including the nitrogen to which $R^4$ and $R^5$ are attached, is a 5-membered ring comprising one nitrogen. In certain instances, the monocyclic heterocyclyl ring is substituted with $C_{1-6}$ alkyl (such as methyl, ethyl, or propyl), spermine, or spermidine. In certain instances, the monocyclic heterocyclyl ring, including the nitrogen to which $R^4$ and $R^5$ are attached, is a 6-membered ring comprising two nitrogens and is substituted with $C_{1-6}$ alkyl (such as methyl, ethyl, or propyl), spermine, or spermidine. In certain instances, the monocyclic heterocyclyl ring, including the nitrogen to which $R^4$ and $R^5$ are attached, is a 5-membered ring comprising two nitrogens and substituted with $C_{1-6}$ alkyl (such as methyl, ethyl, or propyl), spermine, or spermidine.

In certain instances, $R^4$ and $R^5$ are methyl. In certain instances, $R^4$ and $R^5$ are ethyl. In certain instances, $R^4$ and $R^5$ are $C_1$alkyl substituted with —$NR^{5a}R^{5b}$.

In certain embodiments of formula (I), each W is O. In certain embodiments, each W is S. In certain embodiments, each W is Se. In certain embodiments, at least one W is O. In certain embodiments, at least one W is S. In certain embodiments, at least one W is Se.

In formula (I), each $B^1$ is independently selected from an optionally protected heterocyclic base moiety. In certain embodiments, each $B^1$ is independently selected from purine and pyrimidine. In certain embodiments, at least one $B^1$ is purine. In certain embodiments, at least one $B^1$ is pyrimidine. In certain embodiments, each $B^1$ is a naturally occurring nucleobase. In certain embodiments, at least one $B^1$ is a modified or non-naturally occurring nucleobase. In certain embodiments, each $B^1$ is a modified or non-naturally occurring nucleobase.

In certain embodiments, each $B^1$ is independently selected from Thy (thymine), BzCyt (4-benzoyl-cytosine), BzAde (6-benzoyl-adenine), AdeDMF (6-dimethylformamidino-adenine), iBuGua (2-isobutyryl-guanine), and GuaDMF (2-dimethylformamidino-guanine). In certain embodiments, each $B^1$ is independently selected from adenine, guanine, cytosine, thymine, and uracil.

In certain embodiments, each $B^1$ is not azapurine. In certain embodiments, each $B^1$ is not fluoro-substituted azapurine.

In certain embodiments of formula (I), n is an integer selected from one to 50, such as one to 10, one to 20, one to 30, one to 40, or one to 50. In certain embodiments, n is 1, 2, 3, 4, 5, 6, 7, 8, 9, 10, 11, 12, 13, 14, 15, 16, 17, 18, 19, 20, 21, 22, 23, 24, 25, 30, 35, 40, 45, or 50.

In certain instances, $R^1$ and $R^2$ are hydrogen and $R^4$ and $R^5$ are methyl. In certain instances, $R^1$ and $R^2$ are hydrogen and $R^4$ and $R^5$ are ethyl.

In certain instances, $R^1$ and $R^2$ are hydrogen; $R^4$ and $R^5$ are methyl; and each $R^3$ is hydrogen. In certain instances, $R^1$ and $R^2$ are hydrogen; $R^4$ and $R^5$ are ethyl; and each $R^3$ is hydrogen.

In certain instances, $R^1$ and $R^2$ are hydrogen; $R^4$ and $R^5$ are methyl; and each $R^3$ is hydroxyl. In certain instances, $R^1$ and $R^2$ are hydrogen; $R^4$ and $R^5$ are ethyl; and each $R^3$ is hydroxyl.

In certain instances, $R^1$ and $R^2$ are hydrogen; $R^4$ and $R^5$ are methyl; and each $B^1$ is independently selected from Thy (thymine), BzCyt (4-benzoyl-cytosine), BzAde (6-benzoyl-adenine), AdeDMF (6-dimethylformamidino-adenine) iBu-Gua (2-isobutyryl-guanine), and GuaDMF (2-dimethylformamidino-guanine). In certain instances, $R^1$ and $R^2$ are hydrogen; $R^4$ and $R^5$ are methyl; and each $B^1$ is independently selected from adenine, guanine, cytosine, thymine, and uracil.

In certain instances, $R^1$ and $R^2$ are hydrogen; $R^4$ and $R^5$ are ethyl; and each $B^1$ is independently selected from Thy (thymine), BzCyt (4-benzoyl-cytosine), BzAde (6-benzoyl-adenine), AdeDMF (6-dimethylformamidino-adenine), iBu-Gua (2-isobutyryl-guanine), and GuaDMF (2-dimethylformamidino-guanine). In certain instances, $R^1$ and $R^2$ are hydrogen; $R^4$ and $R^5$ are ethyl; and each $B^1$ is independently selected from adenine, guanine, cytosine, thymine, and uracil.

In certain embodiments, the compound comprises about 35-100% of the backbone that is NPN linkage. In certain embodiments, the compound comprises NPN linkage that is about 35, 40, 45, 50, 55, 60, 65, 70, 75, 80, 85, 90, 95, or 100% of the backbone.

Formula II

The present disclosure provides a compound of formula (II):

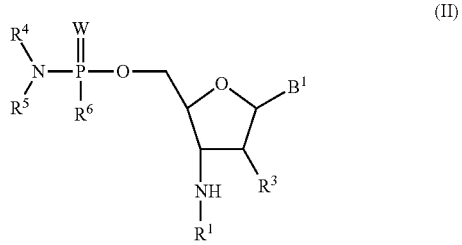

(II)

wherein
$R^1$ is hydrogen or an amino protecting group;
$R^3$ is independently selected from hydrogen, hydroxyl, and —O—$R^{3a}$;
wherein $R^{3a}$ is $C_{1-6}$ alkyl optionally substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$;
wherein $R^{3b}$ is hydrogen or $C_{1-2}$ alkyl;
$R^{3c}$ is hydrogen or $C_{1-2}$ alkyl;
$R^{3d}$ is hydrogen or $C_{1-2}$ alkyl;
a is an integer selected from one to 4;
b is an integer selected from one to 4;
$R^4$ is $C_{1-6}$ alkyl optionally substituted with —$NR^{4a}R^{4b}$;
wherein $R^{4a}$ is hydrogen or $C_{1-2}$ alkyl and $R^{4b}$ is hydrogen or $C_{1-2}$ alkyl;
$R^5$ is $C_{1-6}$ alkyl optionally substituted with —$NR^{5a}R^{5b}$;
wherein $R^{5a}$ is hydrogen or $C_{1-2}$ alkyl and $R^{5b}$ is hydrogen or $C_{1-2}$ alkyl; or
$R^4$ and $R^5$ taken together with the nitrogen to which they are attached form an optionally substituted monocyclic heterocyclyl ring
$R^6$ is a leaving group;
W is independently selected from O, S, and Se; and
$B^1$ is an optionally protected heterocyclic base moiety;
or a salt thereof.

In certain embodiments of formula (II), $R^1$ is hydrogen.

In certain embodiments, $R^1$ is an amino protecting group. Examples of suitable amino protecting group include trityl, dimethoxytrityl, and methoxytrityl. In certain embodiments, $R^1$ is trityl. In certain embodiments, $R^1$ is methoxytrityl.

In certain embodiments, each $R^1$ is not

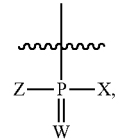

wherein W is O, S, or Se; X is OH or SH; and Z is OH, SH, $CH_3$ or $OC_2H_5$.

In formula (II), $R^3$ is selected from hydrogen, hydroxyl, and —O—$R^{3a}$; wherein $R^{3a}$ is $C_{1-6}$ alkyl optionally substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$.

In certain embodiments, $R^3$ is hydrogen. In certain embodiments, $R^3$ is hydroxyl. In certain embodiments, $R^3$ is —O—$R^{3a}$.

In certain embodiments, $R^{3a}$ is $C_{1-6}$ alkyl, such as methyl, ethyl, or propyl. In certain embodiments, $R^{3a}$ is $C_{1-6}$ alkyl substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$.

In certain embodiments, $R^{3b}$ is hydrogen. In certain embodiments, $R^{3b}$ is methyl or ethyl. In certain embodiments, $R^{3c}$ is hydrogen. In certain embodiments, $R^{3c}$ is methyl or ethyl. In certain embodiments, $R^{3d}$ is hydrogen. In certain embodiments, $R^{3d}$ is methyl or ethyl.

In certain embodiments, a is one. In certain embodiments, a is 2. In certain embodiments, a is 3. In certain embodiments, a is 4.

In certain embodiments, b is one. In certain embodiments, b is 2. In certain embodiments, b is 3. In certain embodiments, b is 4.

In certain embodiments of formula (II), $R^4$ is $C_{1-6}$ alkyl optionally substituted with —$NR^{4a}R^{4b}$; wherein $R^{4a}$ is hydrogen or $C_{1-2}$ alkyl and $R^{4b}$ is hydrogen or $C_{1-2}$ alkyl. In certain embodiments, $R^4$ is $C_{1-6}$ alkyl, such as methyl, ethyl, or propyl. In certain embodiments, $R^4$ is methyl. In certain embodiments, $R^4$ is ethyl.

In certain embodiments of formula (II), $R^5$ is $C_{1-6}$ alkyl optionally substituted with —$NR^{5a}R^{5b}$; wherein $R^{5a}$ is hydrogen or $C_{1-2}$ alkyl and $R^{5b}$ is hydrogen or $C_{1-2}$ alkyl. In certain embodiments, $R^5$ is $C_{1-6}$ alkyl, such as methyl, ethyl, or propyl. In certain embodiments, $R^5$ is methyl. In certain embodiments, $R^5$ is ethyl.

In certain embodiments of formula (II), $R^4$ and $R^5$ taken together with the nitrogen to which they are attached form an optionally substituted monocyclic heterocyclyl ring. In certain instances, the optionally substituted monocyclic heterocyclyl ring is a 4-8 membered ring, such as 4, 5, 6, 7, or 8-membered ring. In certain instances, the optionally substituted monocyclic heterocyclyl ring, including the nitrogen to which $R^4$ and $R^5$ are attached, comprises 1, 2, or 3 heteroatoms. In certain instances, the optionally substituted monocyclic heterocyclyl ring, including the nitrogen to which $R^4$ and $R^5$ are attached, comprises 1, 2, or 3 heteroatoms selected from nitrogen, oxygen, and sulfur. In certain instances, the optionally substituted monocyclic heterocyclyl ring, including the nitrogen to which $R^4$ and $R^5$ are attached, is a 6-membered ring comprising one nitrogen. In certain instances, the optionally substituted monocyclic heterocyclyl ring, including the nitrogen to which $R^4$ and $R^5$ are attached, is a 5-membered ring comprising one nitrogen. In certain instances, the monocyclic heterocyclyl ring is substituted with $C_{1-6}$ alkyl (such as methyl, ethyl, or propyl), spermine, or spermidine. In certain instances, the monocyclic heterocyclyl ring, including the nitrogen to which $R^4$ and $R^5$ are attached, is a 6-membered ring comprising two nitrogens and is substituted with $C_{1-6}$ alkyl (such as methyl, ethyl, or propyl), spermine, or spermidine. In certain instances, the monocyclic heterocyclyl ring, including the nitrogen to which $R^4$ and $R^5$ are attached, is a 5-membered ring comprising two nitrogens and substituted with $C_{1-6}$ alkyl (such as methyl, ethyl, or propyl), spermine, or spermidine.

In certain instances, $R^4$ and $R^5$ are methyl. In certain instances, $R^4$ and $R^5$ are ethyl. In certain instances, $R^4$ and $R^5$ are $C_1$alkyl substituted with —$NR^{5a}R^{5b}$.

In formula (II), $R^6$ is a leaving group. A leaving group is a group that is subject to nucleophilic displacement. Suitable leaving groups are well known in the art, e.g., see, "Advanced Organic Chemistry," Jerry March, 5$^{th}$ Ed., pp. 351-357, John Wiley and Sons, N.Y. Examples of leaving groups include chloro, iodo, bromo, fluoro, methanesulfonyloxy (mesyloxy), tosyloxy, triflyloxy, nitro-phenylsulfonyloxy (nosyloxy), bromo-phenylsulfonyloxy (brosyloxy), triazolyl, benzotriazolyl, hydroxybenzotriazolyl ester, and 1-(mesitylene-2-sulfonyl)-3-nitro-1H-1,2,4-triazole (MSNT). In certain embodiments, $R^6$ is a halogen, such as chloro, bromo, or iodo.

In certain embodiments of formula (II), W is O. In certain embodiments, W is S. In certain embodiments, W is Se.

In formula (II), $B^1$ is independently selected from an optionally protected heterocyclic base moiety. In certain embodiments, $B^1$ is independently selected from purine and pyrimidine. In certain embodiments, $B^1$ is purine. In certain embodiments, $B^1$ is pyrimidine. In certain embodiments, $B^1$ is a naturally occurring nucleobase. In certain embodiments, $B^1$ is a modified or non-naturally occurring nucleobase.

In certain embodiments, each $B^1$ is independently selected from Thy (thymine), BzCyt (4-benzoyl-cytosine), BzAde (6-benzoyl-adenine), AdeDMF (6-dimethylformamidino-adenine), iBuGua (2-isobutyryl-guanine), and GuaDMF (2-dimethylformamidino-guanine). In certain embodiments, each $B^1$ is independently selected from adenine, guanine, cytosine, thymine, and uracil.

In certain embodiments, $B^1$ is not azapurine. In certain embodiments, $B^1$ is not fluoro-substituted azapurine.

In certain instances, $R^1$ is hydrogen; $R^4$ and $R^5$ are methyl; and $R^3$ is hydrogen. In certain instances, $R^1$ is hydrogen; $R^4$ and $R^5$ are ethyl; and $R^3$ is hydrogen.

In certain instances, $R^1$ is hydrogen; $R^4$ and $R^5$ are methyl; and $R^3$ is hydroxyl. In certain instances, $R^1$ is hydrogen; $R^4$ and $R^5$ are ethyl; and $R^3$ is hydroxyl.

In certain instances, $R^1$ is hydrogen; $R^4$ and $R^5$ are methyl; and each $B^1$ is independently selected from Thy (thymine), BzCyt (4-benzoyl-cytosine), BzAde (6-benzoyl-adenine), AdeDMF (6-dimethylformamidino-adenine), iBuGua (2-isobutyryl-guanine), and GuaDMF (2-dimethylformamidino-guanine). In certain instances, $R^1$ is hydrogen; $R^4$ and $R^5$ are methyl; and each $B^1$ is independently selected from adenine, guanine, cytosine, thymine, and uracil.

In certain instances, $R^1$ is hydrogen; $R^4$ and $R^5$ are ethyl; and each $B^1$ is independently selected from Thy (thymine), BzCyt (4-benzoyl-cytosine), BzAde (6-benzoyl-adenine), AdeDMF (6-dimethylformamidino-adenine), iBuGua (2-isobutyryl-guanine), and GuaDMF (2-dimethylformamidino-guanine). In certain instances, $R^1$ is hydrogen; $R^4$ and $R^5$ are ethyl; and each $B^1$ is independently selected from adenine, guanine, cytosine, thymine, and uracil.

Formula III

The present disclosure provides a compound of formula (III):

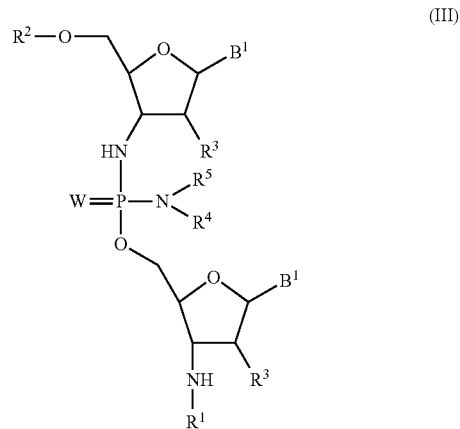

wherein
$R^1$ is hydrogen or an amino protecting group;
$R^2$ is hydrogen, a hydroxyl protecting group or solid support;
each $R^3$ is independently selected from hydrogen, hydroxyl, and —O—$R^{3a}$;
wherein each $R^{3a}$ is $C_{1-6}$ alkyl optionally substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$;
wherein each $R^{3b}$ is hydrogen or $C_{1-2}$ alkyl;
each $R^{3c}$ is hydrogen or $C_{1-2}$ alkyl;
each $R^{3d}$ is hydrogen or $C_{1-2}$ alkyl;
each a is an integer selected from one to 4;
each b is an integer selected from one to 4;
each $R^4$ is $C_{1-6}$ alkyl optionally substituted with —$NR^{4a}R^{4b}$;
wherein $R^{4a}$ is hydrogen or $C_{1-2}$ alkyl and $R^{4b}$ is hydrogen or $C_{1-2}$ alkyl;
each $R^5$ is $C_{1-6}$ alkyl optionally substituted with —$NR^{5a}R^{5b}$;
wherein $R^{5a}$ is hydrogen or $C_{1-2}$ alkyl and $R^{5b}$ is hydrogen or $C_{1-2}$ alkyl; or
$R^4$ and $R^5$ taken together with the nitrogen to which they are attached form an optionally substituted monocyclic heterocyclyl ring;
each W is independently selected from O, S, and Se; and
each $B^1$ is independently selected from an optionally protected heterocyclic base moiety;
or a salt thereof.

In certain embodiments of formula (III), $R^1$ is hydrogen.
In certain embodiments, $R^1$ is an amino protecting group. Examples of suitable amino protecting group include trityl, dimethoxytrityl, and methoxytrityl. In certain embodiments, $R^1$ is trityl. In certain embodiments, $R^1$ is methoxytrityl.

In certain embodiments, each R is not

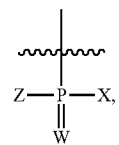

wherein W is O, S, or Se; X is OH or SH; and Z is O—H, SH, $CH_3$, or $OC_2H_5$.

In certain embodiments of formula (III), $R^2$ is hydrogen.

In certain embodiments, $R^2$ is a solid support. Suitable solid supports can be made out of glass or polymers. For example, suitable solid supports can be made out of polystyrene (such as polystyrene crosslinked with divinylbenzene), controlled pore glass (CPG), or TentaGel® (Sigma-Aldrich, St. Louis, Mo.). Suitable solid supports include, but are not limited to, slides, beads, chips, particles, strands, gels, sheets, tubing, spheres, containers, capillaries, pads, slices, films, plates and the like. In certain embodiments, a solid support may be biological, nonbiological, organic, inorganic, or any combination thereof.

In certain embodiments, $R^2$ is a hydroxyl protecting group. Examples of suitable hydroxyl protecting group include tert-butyl-dimethylsilyl, methoxymethyl, tetrahydropyranyl, tert-butyl, benzyl, and tert-butyldiphenylsilyl. In certain embodiments, $R^2$ is tert-butyl-dimethylsilyl.

In certain instances, $R^1$ and $R^2$ are hydrogen. In certain instances, $R^1$ is hydrogen and $R^2$ is a hydroxyl protecting group. In certain instances, $R^1$ is an amino protecting group and $R^2$ is hydrogen. In certain instances, $R^1$ is an amino protecting group and $R^2$ is a solid support. In certain instances, $R^1$ is an amino protecting group and $R^2$ is a hydroxyl protecting group.

In formula (III), each $R^3$ is independently selected from hydrogen, hydroxyl, and —O—$R^{3a}$; wherein each $R^{3a}$ is $C_{1-6}$ alkyl optionally substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$.

In certain embodiments, each $R^3$ is hydrogen. In certain embodiments, each $R^3$ is hydroxyl. In certain embodiments, each $R^3$ is —O—$R^{3a}$. In certain instances, at least one $R^3$ is —O—$R^{3a}$.

In certain embodiments, at least one $R^{3a}$ is $C_{1-6}$ alkyl, such as methyl, ethyl, or propyl. In certain embodiments, at least one $R^{3a}$ is $C_{1-6}$ alkyl substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$.

In certain embodiments, $R^{3b}$ is hydrogen. In certain embodiments, $R^{3b}$ is methyl or ethyl. In certain embodiments, $R^{3c}$ is hydrogen. In certain embodiments, $R^{3c}$ is methyl or ethyl. In certain embodiments, $R^{3d}$ is hydrogen. In certain embodiments, $R^{3d}$ is methyl or ethyl.

In certain embodiments, a is one. In certain embodiments, a is 2. In certain embodiments, a is 3. In certain embodiments, a is 4.

In certain embodiments, b is one. In certain embodiments, b is 2. In certain embodiments, b is 3. In certain embodiments, b is 4.

In certain embodiments of formula (III), $R^4$ is $C_{1-6}$ alkyl optionally substituted with —$NR^{4a}R^{4b}$; wherein $R^{4a}$ is hydrogen or $C_{1-2}$ alkyl and $R^{4b}$ is hydrogen or $C_{1-2}$ alkyl. In certain embodiments, $R^4$ is $C_{1-6}$ alkyl, such as methyl, ethyl, or propyl. In certain embodiments, $R^4$ is methyl. In certain embodiments, $R^4$ is ethyl.

In certain embodiments of formula (III), $R^5$ is $C_{1-6}$ alkyl optionally substituted with —$NR^{5a}R^{5b}$; wherein $R^{5a}$ is hydrogen or $C_{1-2}$ alkyl and $R^{5b}$ is hydrogen or $C_{1-2}$ alkyl. In certain embodiments, $R^5$ is $C_{1-6}$ alkyl, such as methyl, ethyl, or propyl. In certain embodiments, $R^5$ is methyl. In certain embodiments, each $R^5$ is ethyl.

In certain embodiments of formula (III), $R^4$ and $R^5$ taken together with the nitrogen to which they are attached form an optionally substituted monocyclic heterocyclyl ring. In certain instances, the optionally substituted monocyclic heterocyclyl ring is a 4-8 membered ring, such as 4, 5, 6, 7, or 8-membered ring. In certain instances, the optionally substituted monocyclic heterocyclyl ring, including the nitrogen to which $R^4$ and $R^5$ are attached, comprises 1, 2, or 3 heteroatoms. In certain instances, the optionally substituted monocyclic heterocyclyl ring, including the nitrogen to which $R^4$ and $R^5$ are attached, comprises 1, 2, or 3 heteroatoms selected from nitrogen, oxygen, and sulfur. In certain instances, the optionally substituted monocyclic heterocyclyl ring, including the nitrogen to which $R^4$ and $R^5$ are attached, is a 6-membered ring comprising one nitrogen. In certain instances, the optionally substituted monocyclic heterocyclyl ring, including the nitrogen to which $R^4$ and $R^5$ are attached, is a 5-membered ring comprising one nitrogen. In certain instances, the monocyclic heterocyclyl ring is substituted with $C_{1-6}$ alkyl (such as methyl, ethyl, or propyl), spermine, or spermidine. In certain instances, the monocyclic heterocyclyl ring, including the nitrogen to which $R^4$ and $R^5$ are attached, is a 6-membered ring comprising two nitrogens and is substituted with $C_{1-6}$ alkyl (such as methyl, ethyl, or propyl), spermine, or spermidine. In certain instances, the monocyclic heterocyclyl ring, including the nitrogen to which $R^4$ and $R^5$ are attached, is a 5-membered ring comprising two nitrogens and substituted with $C_{1-6}$ alkyl (such as methyl, ethyl, or propyl), spermine, or spermidine.

In certain instances, $R^4$ and $R^5$ are methyl. In certain instances, $R^4$ and $R^5$ are ethyl. In certain instances, $R^4$ and $R^5$ are $C_1$alkyl substituted with —$NR^{5a}R^{5b}$.

In certain embodiments of formula (III), W is O. In certain embodiments, W is S. In certain embodiments, W is Se.

In formula (III), each $B^1$ is independently selected from an optionally protected heterocyclic base moiety. In certain embodiments, each $B^1$ is independently selected from purine and pyrimidine. In certain embodiments, at least one $B^1$ is purine. In certain embodiments, at least one $B^1$ is pyrimidine. In certain embodiments, each $B^1$ is a naturally occurring nucleobase. In certain embodiments, at least one $B^1$ is a modified or non-naturally occurring nucleobase. In certain embodiments, each $B^1$ is a modified or non-naturally occurring nucleobase.

In certain embodiments, each $B^1$ is independently selected from Thy (thymine), BzCyt (4-benzoyl-cytosine), BzAde (6-benzoyl-adenine), AdeDMF (6-dimethylformamidino-adenine), iBuGua (2-isobutyryl-guanine), and GuaDMF (2-dimethylformamidino-guanine). In certain embodiments, each $B^1$ is independently selected from adenine, guanine, cytosine, thymine, and uracil.

In certain embodiments, each $B^1$ is not azapurine. In certain embodiments, each $B^1$ is not fluoro-substituted azapurine.

In certain instances, $R^1$ and $R^2$ are hydrogen and $R^4$ and $R^5$ are methyl. In certain instances, $R^1$ and $R^2$ are hydrogen and $R^4$ and $R^5$ are ethyl.

In certain instances, $R^1$ and $R^2$ are hydrogen; $R^4$ and $R^5$ are methyl; and each $R^3$ is hydrogen. In certain instances, $R^1$ and $R^2$ are hydrogen; $R^4$ and $R^5$ are ethyl; and each $R^3$ is hydrogen.

In certain instances, $R^1$ and $R^2$ are hydrogen; $R^4$ and $R^5$ are methyl; and each $R^3$ is hydroxyl. In certain instances, $R^1$ and $R^2$ are hydrogen; $R^4$ and $R^5$ are ethyl; and each $R^3$ is hydroxyl.

In certain instances, $R^1$ and $R^2$ are hydrogen; $R^4$ and $R^5$ are methyl; and each $B^1$ is independently selected from Thy (thymine), BzCyt (4-benzoyl-cytosine), BzAde (6-benzoyl-adenine), AdeDMF (6-dimethylformamidino-adenine), iBuGua (2-isobutyryl-guanine), and GuaDMF (2-dimethylformamidino-guanine). In certain instances, $R^1$ and $R^2$ are hydrogen; $R^4$ and $R^5$ are methyl; and each $B^1$ is independently selected from adenine, guanine, cytosine, thymine, and uracil.

In certain instances, $R^1$ and $R^2$ are hydrogen; $R^4$ and $R^5$ are ethyl; and each $B^1$ is independently selected from Thy (thymine), BzCyt (4-benzoyl-cytosine), BzAde (6-benzoyl-adenine), AdeDMF (6-dimethylformamidino-adenine), iBuGua (2-isobutyryl-guanine), and GuaDMF (2-dimethylformamidino-guanine). In certain instances, $R^1$ and $R^2$ are hydrogen; $R^4$ and $R^5$ are ethyl; and each $B^1$ is independently selected from adenine, guanine, cytosine, thymine, and uracil.

The present disclosure provides compounds of following formulae or salts thereof and their use in the methods of the embodiments.

1

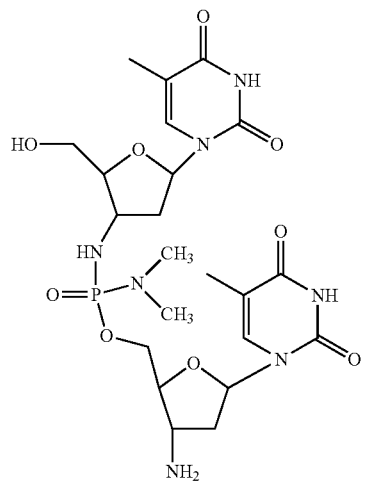

2

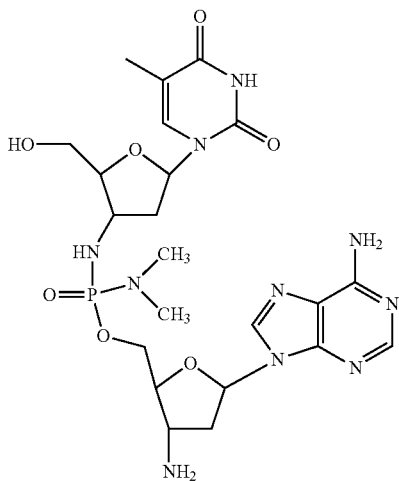

The present disclosure provides compounds of following formulae or salts thereof and their use in the methods of the embodiments.

3

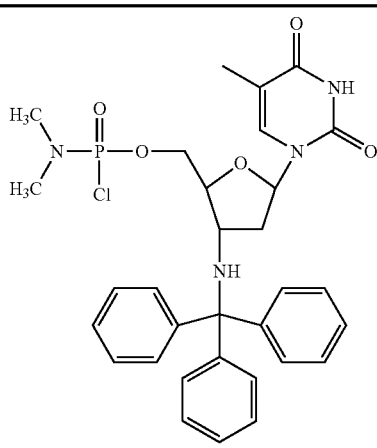

3'-Aminotrityl-3'-deoxythymidine-5'-(chloro,N-N-dimethyl) phosphoramidate

4

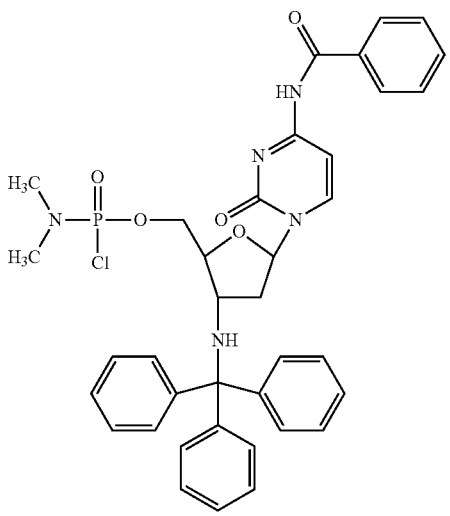 [SMILES: CN(C)P(=O)(Cl)OCC1OC(n2ccc(NC(=O)c3ccccc3)nc2=O)CC1NC(c1ccccc1)(c1ccccc1)c1ccccc1]

$N^4$-benzoyl-3'-aminotrityl-2',3'-dideoxycytidine-5'-(chloro, N-N,dimethyl) phosphoramidate

| 5 | 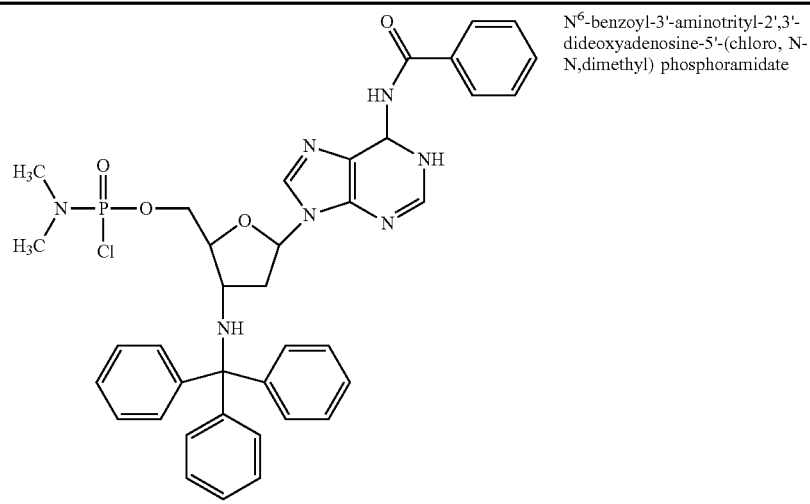 | N[6]-benzoyl-3'-aminotrityl-2',3'-dideoxyadenosine-5'-(chloro, N-N,dimethyl) phosphoramidate |
| 6 | 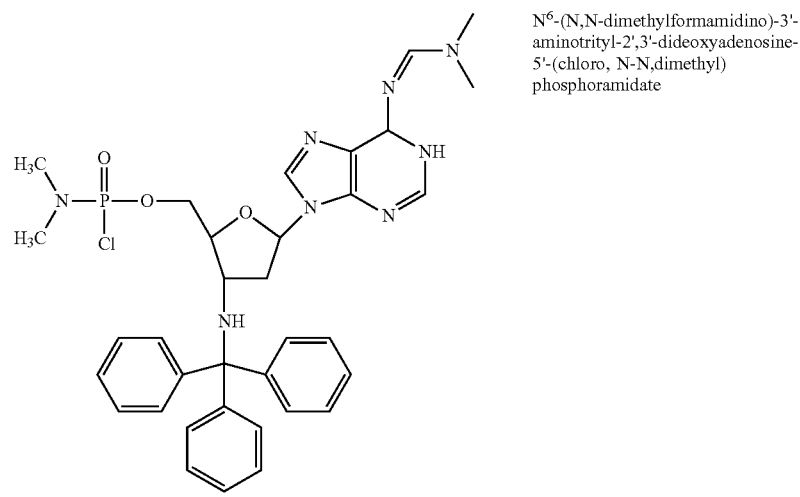 | N[6]-(N,N-dimethylformamidino)-3'-aminotrityl-2',3'-dideoxyadenosine-5'-(chloro, N-N,dimethyl) phosphoramidate |
| 7 | 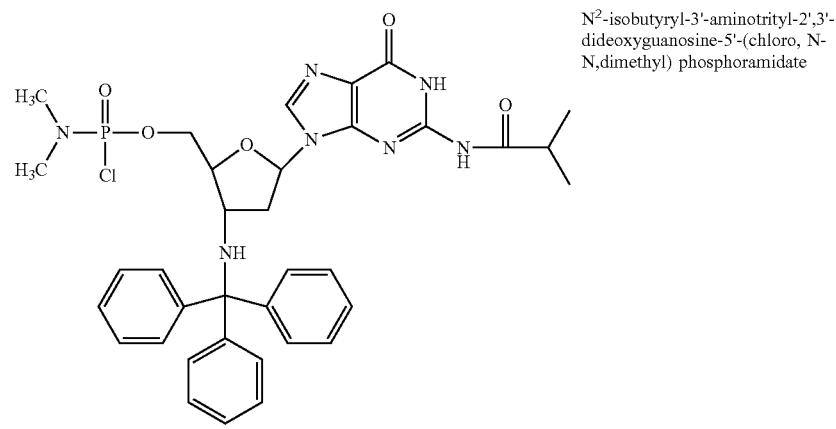 | N[2]-isobutyryl-3'-aminotrityl-2',3'-dideoxyguanosine-5'-(chloro, N-N,dimethyl) phosphoramidate |

-continued

| | | |
|---|---|---|
| 8 | 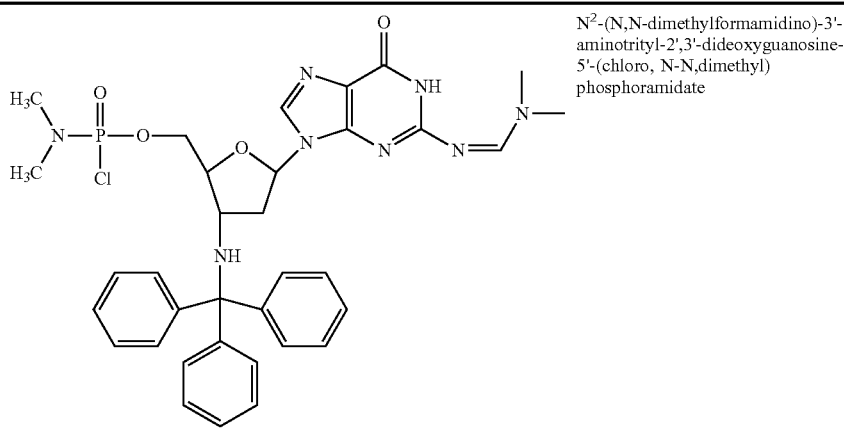 | $N^2$-(N,N-dimethylformamidino)-3'-aminotrityl-2',3'-dideoxyguanosine-5'-(chloro, N-N,dimethyl) phosphoramidate |
| 9 | 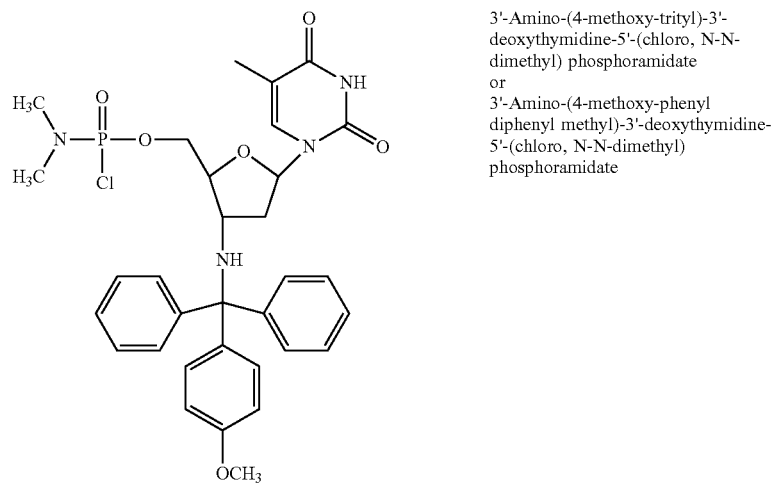 | 3'-Amino-(4-methoxy-trityl)-3'-deoxythymidine-5'-(chloro, N-N-dimethyl) phosphoramidate or 3'-Amino-(4-methoxy-phenyl diphenyl methyl)-3'-deoxythymidine-5'-(chloro, N-N-dimethyl) phosphoramidate |
| 10 | 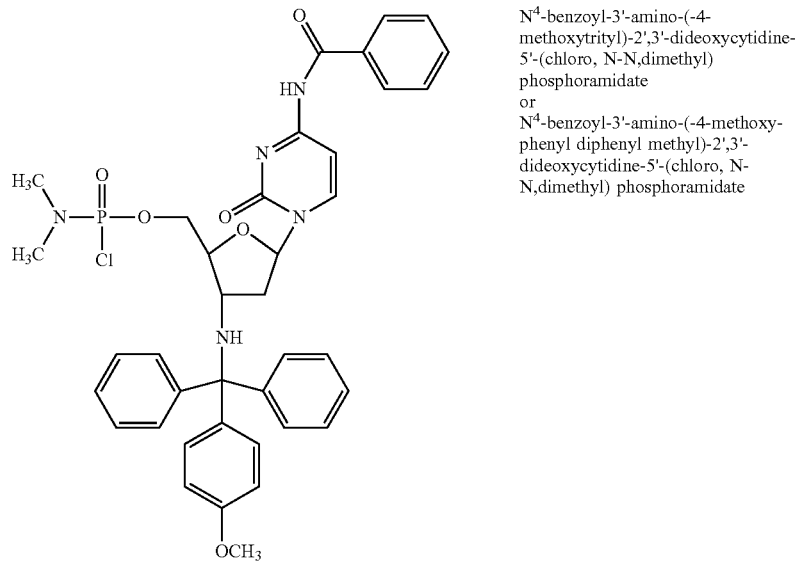 | $N^4$-benzoyl-3'-amino-(-4-methoxytrityl)-2',3'-dideoxycytidine-5'-(chloro, N-N,dimethyl) phosphoramidate or $N^4$-benzoyl-3'-amino-(-4-methoxy-phenyl diphenyl methyl)-2',3'-dideoxycytidine-5'-(chloro, N-N,dimethyl) phosphoramidate |

| | | |
|---|---|---|
| 11 | 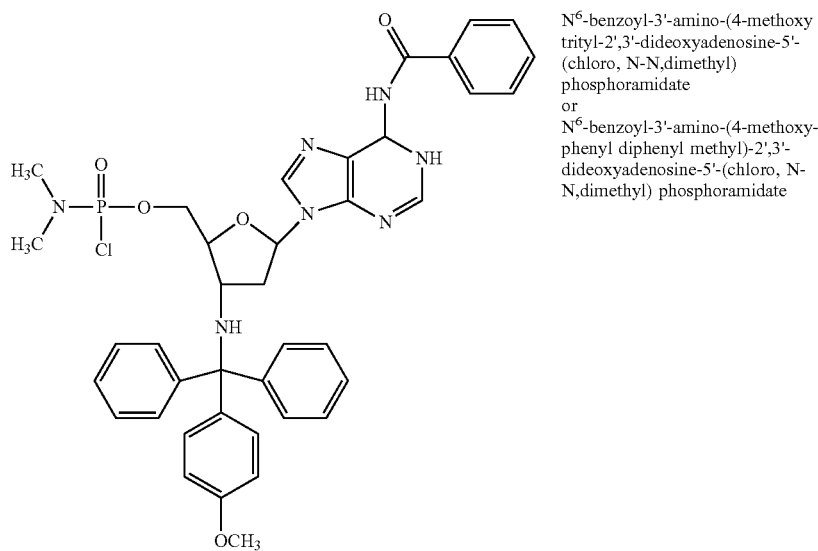 | N6-benzoyl-3'-amino-(4-methoxy trityl-2',3'-dideoxyadenosine-5'-(chloro, N-N,dimethyl) phosphoramidate or N6-benzoyl-3'-amino-(4-methoxy-phenyl diphenyl methyl)-2',3'-dideoxyadenosine-5'-(chloro, N-N,dimethyl) phosphoramidate |
| 12 | 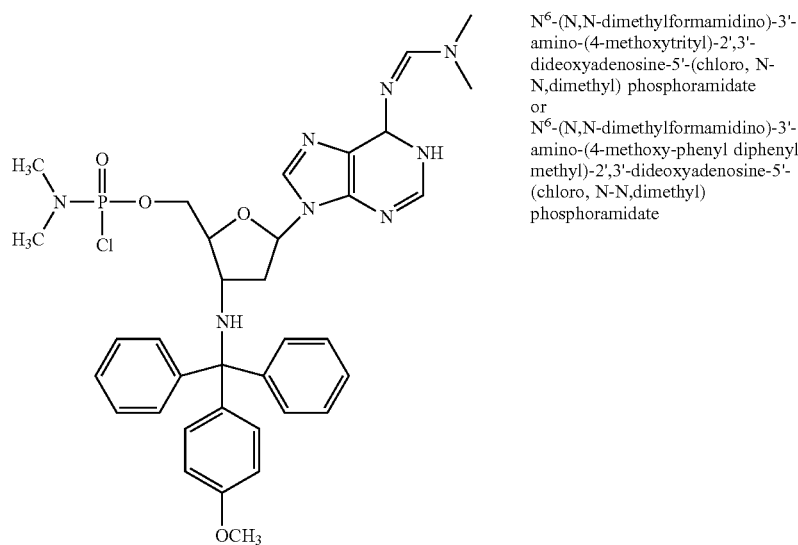 | N6-(N,N-dimethylformamidino)-3'-amino-(4-methoxytrityl)-2',3'-dideoxyadenosine-5'-(chloro, N-N,dimethyl) phosphoramidate or N6-(N,N-dimethylformamidino)-3'-amino-(4-methoxy-phenyl diphenyl methyl)-2',3'-dideoxyadenosine-5'-(chloro, N-N,dimethyl) phosphoramidate |
| 13 | 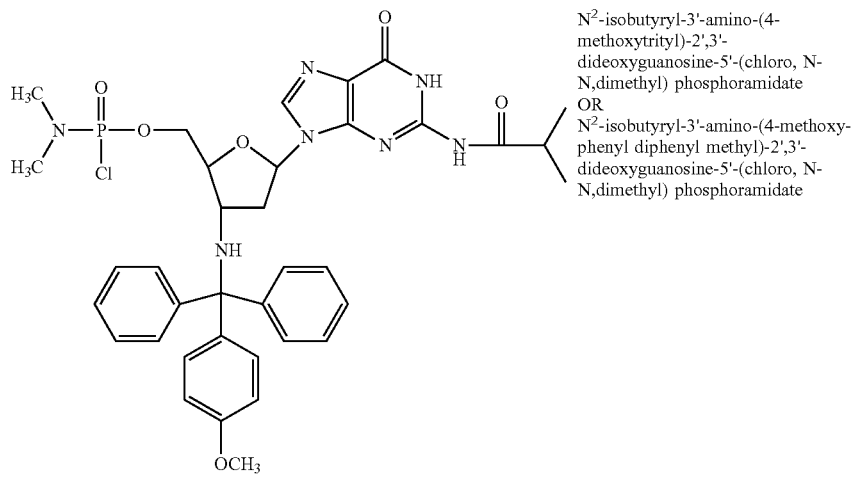 | N2-isobutyryl-3'-amino-(4-methoxytrityl)-2',3'-dideoxyguanosine-5'-(chloro, N-N,dimethyl) phosphoramidate OR N2-isobutyryl-3'-amino-(4-methoxy-phenyl diphenyl methyl)-2',3'-dideoxyguanosine-5'-(chloro, N-N,dimethyl) phosphoramidate |

14 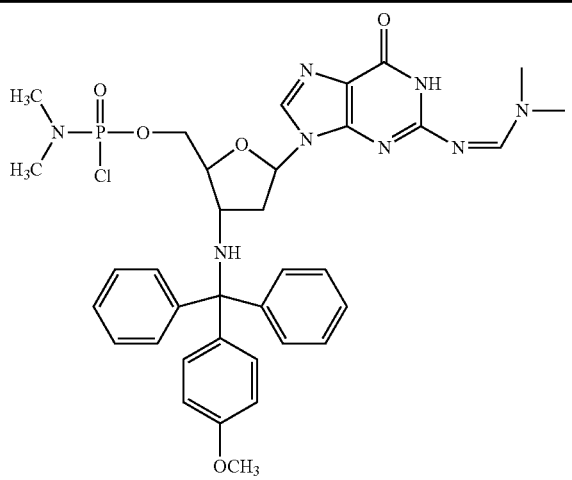

N²-(N,N-dimethylformamidino)-3'-amino-(4-methoxytrityl)-2',3'-dideoxyguanosine-5'-(chloro, N-N,dimethyl) phosphoramidate
OR
N²-(N,N-dimethylformamidino)-3'-amino-(4-methoxy-phenyl diphenyl methyl)-2',3'-dideoxyguanosine-5'-(chloro, N-N,dimethyl) phosphoramidate Gapmer Comprising Moiety of Formula IV The present disclosure provides an oligonucleotide, wherein the nucleoside subunits of the oligonucleotide are joined by intersubunit linkages, wherein at least one of the intersubunit linkages is a phosphorothioate or phosphate linkage, and wherein the oligonucleotide comprises a moiety of formula (IV)

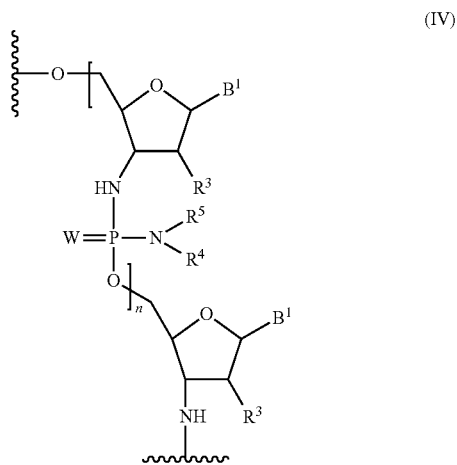

(IV)

wherein
each $R^3$ is independently selected from hydrogen, hydroxyl, and —O—$R^{3a}$;
wherein each $R^{3a}$ is $C_{1-6}$ alkyl optionally substituted with —NR$^{3b}$R$^{3c}$, imidazolyl, —(CH$_2$)$_a$O(CH$_2$)$_b$NR$^{3b}$R$^{3c}$, or —(CH$_2$)$_a$ONR$^{3d}$(CH$_2$)$_b$NR$^{3b}$R$^{3c}$;
wherein each $R^{3b}$ is hydrogen or $C_{1-2}$ alkyl;
each $R^{3c}$ is hydrogen or $C_{1-2}$ alkyl;
each $R^{3d}$ is hydrogen or $C_{1-2}$ alkyl;
each a is an integer selected from one to 4;
each b is an integer selected from one to 4;
each $R^4$ is $C_{1-6}$ alkyl optionally substituted with —NR$^{4a}$R$^{4b}$;
wherein $R^{4a}$ is hydrogen or $C_{1-2}$ alkyl and $R^{4b}$ is hydrogen or $C_{1-2}$ alkyl;
each $R^5$ is $C_{1-6}$ alkyl optionally substituted with —NR$^{5a}$R$^{5b}$;
wherein $R^{5a}$ is hydrogen or $C_{1-2}$ alkyl and $R^{5b}$ is hydrogen or $C_{1-2}$ alkyl; or $R^4$ and $R^5$ taken together with the nitrogen to which they are attached form an optionally substituted monocyclic heterocyclyl ring;
each W is independently selected from O, S, and Se;
each $B^1$ is independently selected from an optionally protected heterocyclic base moiety; and
n is an integer selected from one to 50;
or a salt thereof;
provided that if the oligonucleotide terminates at the 3' end or 5' end with the moiety of formula IV, the terminal group —O— or —NH— comprises a hydrogen to provide proper valence to the moiety of formula IV.

In certain embodiments, the oligonucleotide comprises a sequence complementary to an mRNA from a specific gene.

In certain embodiments, the oligonucleotide can comprise non-natural intersubunit linkages, such as, but not limited to, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thiophosphoramidates, thionoalkylphosphonates, thionoalkylphosphotriesters, thiophosphates, selenophosphates and boranophosphates having normal 3'-5' linkages, 2'-5' linked analogs of these, and those having inverted polarity wherein one or more intersubunit linkages is a 3' to 3', 5' to 5' or 2' to 2' linkage. Methods for synthesizing these modified intersubunit linkages can be found in U.S. Pat. Nos. 5,177,196; 5,188,897; 5,264,423; 5,276,019; 5,278,302; 5,286,717; 5,321,131; 5,399,676; 40 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein in their entirety.

Techniques for synthesizing oligonucleotides with varying types of intersubunit linkages can be found, inter alia, in U.S. Pat. No. 7,494,982, the disclosure of which is incorporated herein in its entirety.

In certain embodiments, the oligonucleotide is about 6 to about 100 nucleotides in length, or about 6 to about 50 nucleotides in length, or about 6 to about 30 nucleotides in length, or about 6 to about 20 nucleotides in length. In certain embodiments, the oligonucleotide is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 nucleotides.

In the moiety of formula (IV), each $R^3$ is independently selected from hydrogen, hydroxyl, and —O—$R^{3a}$; wherein each $R^{3a}$ is $C_{1-6}$ alkyl optionally substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$.

In certain embodiments, each $R^3$ is hydrogen. In certain embodiments, each $R^3$ is hydroxyl. In certain embodiments, each $R^3$ is —O—$R^{3a}$. In certain instances, at least one $R^3$ is —O—$R^{3a}$.

In certain embodiments, at least one $R^{3a}$ is $C_{1-6}$ alkyl, such as methyl, ethyl, or propyl. In certain embodiments, at least one $R^{3a}$ is $C_{1-6}$ alkyl substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$.

In certain embodiments, $R^{3b}$ is hydrogen. In certain embodiments, $R^{3b}$ is methyl or ethyl.

In certain embodiments, $R^{3c}$ is hydrogen. In certain embodiments, $R^{3c}$ is methyl or ethyl. In certain embodiments, $R^{3d}$ is hydrogen. In certain embodiments, $R^{3d}$ is methyl or ethyl.

In certain embodiments, a is one. In certain embodiments, a is 2. In certain embodiments, a is 3. In certain embodiments, a is 4.

In certain embodiments, b is one. In certain embodiments, b is 2. In certain embodiments, b is 3. In certain embodiments, b is 4.

In certain embodiments of the moiety of formula (IV), each $R^4$ is $C_{1-6}$ alkyl optionally substituted with —$NR^{4a}R^{4b}$; wherein $R^{4a}$ is hydrogen or $C_{1-2}$ alkyl and $R^{4b}$ is hydrogen or $C_{1-2}$ alkyl. In certain embodiments, each $R^4$ is $C_{1-6}$ alkyl, such as methyl, ethyl, or propyl. In certain embodiments, each $R^4$ is methyl. In certain embodiments, each $R^4$ is ethyl.

In certain embodiments of the moiety of formula (IV), each $R^5$ is $C_{1-6}$ alkyl optionally substituted with —$NR^{5a}R^{5b}$; wherein $R^{5a}$ is hydrogen or $C_{1-2}$ alkyl and $R^{5b}$ is hydrogen or $C_{1-2}$ alkyl. In certain embodiments, each $R^5$ is $C_{1-6}$ alkyl, such as methyl, ethyl, or propyl. In certain embodiments, each $R^5$ is methyl. In certain embodiments, each $R^5$ is ethyl.

In certain embodiments of the moiety of formula (IV), $R^4$ and $R^5$ taken together with the nitrogen to which they are attached form an optionally substituted monocyclic heterocyclyl ring. In certain instances, the optionally substituted monocyclic heterocyclyl ring is a 4-8 membered ring, such as 4, 5, 6, 7, or 8-membered ring. In certain instances, the optionally substituted monocyclic heterocyclyl ring, including the nitrogen to which $R^4$ and $R^5$ are attached, comprises 1, 2, or 3 heteroatoms. In certain instances, the optionally substituted monocyclic heterocyclyl ring, including the nitrogen to which $R^4$ and $R^5$ are attached, comprises 1, 2, or 3 heteroatoms selected from nitrogen, oxygen, and sulfur. In certain instances, the optionally substituted monocyclic heterocyclyl ring, including the nitrogen to which $R^4$ and $R^5$ are attached, is a 6-membered ring comprising one nitrogen. In certain instances, the optionally substituted monocyclic heterocyclyl ring, including the nitrogen to which $R^4$ and $R^5$ are attached, is a 5-membered ring comprising one nitrogen. In certain instances, the monocyclic heterocyclyl ring is substituted with $C_{1-6}$ alkyl (such as methyl, ethyl, or propyl), spermine, or spermidine. In certain instances, the monocyclic heterocyclyl ring, including the nitrogen to which $R^4$ and $R^5$ are attached, is a 6-membered ring comprising two nitrogens and is substituted with $C_{1-6}$ alkyl (such as methyl, ethyl, or propyl), spermine, or spermidine. In certain instances, the monocyclic heterocyclyl ring, including the nitrogen to which $R^4$ and $R^5$ are attached, is a 5-membered ring comprising two nitrogens and substituted with $C_{1-6}$ alkyl (such as methyl, ethyl, or propyl), spermine, or spermidine.

In certain instances, $R^4$ and $R^5$ are methyl. In certain instances, $R^4$ and $R^5$ are ethyl. In certain instances, $R^4$ and $R^5$ are $C_1$ alkyl substituted with —$NR^{5a}R^{5b}$.

In certain embodiments in the moiety of formula (IV), each W is O. In certain embodiments, each W is S. In certain embodiments, each W is Se. In certain embodiments, at least one W is O. In certain embodiments, at least one W is S. In certain embodiments, at least one W is Se.

In the moiety of formula (IV), each $B^1$ is independently selected from an optionally protected heterocyclic base moiety. In certain embodiments, each $B^1$ is independently selected from purine and pyrimidine. In certain embodiments, at least one $B^1$ is purine. In certain embodiments, at least one $B^1$ is pyrimidine. In certain embodiments, each $B^1$ is a naturally occurring nucleobase. In certain embodiments, at least one $B^1$ is a modified or non-naturally occurring nucleobase. In certain embodiments, each $B^1$ is a modified or non-naturally occurring nucleobase.

In certain embodiments, each $B^1$ is independently selected from Thy (thymine), BzCyt (4-benzoyl-cytosine), BzAde (6-benzoyl-adenine), AdeDMF (6-dimethylformamidino-adenine), iBuGua (2-isobutyryl-guanine), and GuaDMF (2-dimethylformamidino-guanine). In certain embodiments, each $B^1$ is independently selected from adenine, guanine, cytosine, thymine, and uracil.

In certain embodiments, each $B^1$ is not azapurine. In certain embodiments, each $B^1$ is not fluoro-substituted azapurine.

In certain embodiments of the moiety of formula (IV), n is an integer selected from one to 50, such as one to 10, one to 20, one to 30, one to 40, or one to 50. In certain embodiments, n is 1, 2, 3, 4, 5, 6, 7, 8, 9, 10, 11, 12, 13, 14, 15, 16, 17, 18, 19, 20, 21, 22, 23, 24, 25, 30, 35, 40, 45, or 50.

In certain instances, $R^4$ and $R^5$ are methyl; and each $R^3$ is hydrogen. In certain instances, $R^4$ and $R^5$ are ethyl; and each $R^3$ is hydrogen.

In certain instances, $R^4$ and $R^5$ are methyl; and each $R^3$ is hydroxyl. In certain instances, $R^4$ and $R^5$ are ethyl; and each $R^3$ is hydroxyl.

In certain instances, $R^4$ and $R^5$ are methyl; and each $B^1$ is independently selected from Thy (thymine), BzCyt (4-benzoyl-cytosine), BzAde (6-benzoyl-adenine), AdeDMF (6-dimethylformamidino-adenine), iBuGua (2-isobutyryl-guanine), and GuaDMF (2-dimethylformamidino-guanine). In certain instances, $R^4$ and $R^5$ are methyl; and each $B^1$ is independently selected from adenine, guanine, cytosine, thymine, and uracil.

In certain instances, $R^4$ and $R^5$ are ethyl; and each $B^1$ is independently selected from Thy (thymine), BzCyt (4-benzoyl-cytosine), BzAde (6-benzoyl-adenine), AdeDMF (6-dimethylformamidino-adenine), iBuGua (2-isobutyryl-guanine), and GuaDMF (2-dimethylformamidino-guanine). In certain instances, $R^4$ and $R^5$ are ethyl; and each $B^1$ is independently selected from adenine, guanine, cytosine, thymine, and uracil.

In certain embodiments, at least one intersubunit phosphorothioate or phosphate linkage is placed between two flanking regions of the moiety of formula (IV). In certain embodiments, the intersubunit linkage between two flanking regions of the moiety of formula (IV) is phosphorothioate. In certain embodiments, the intersubunit linkage between two flanking regions of the moiety of formula (IV) is phosphate. In certain embodiments, there is a region comprising nucleotides linked by a mixture of intersubunit phosphorothioate and phosphate linkages that is placed between two flanking regions of the moiety of formula (IV).

In certain embodiments, the oligonucleotide comprises the moiety of formula (IV) located on the 5' end of the oligonucleotide; the moiety of formula (IV) located on the 3' end of the oligonucleotide; and 3 to 30 contiguous nucleotides linked by phosphorothioate or phosphate linkages located in between said moiety of formula (IV) located on the 5' end and said moiety of formula (IV) located on the 3' end of the oligonucleotide.

In certain embodiments, for the moiety of formula (IV) located on the 5' end of the oligonucleotide, n is an integer selected from one to 50, such as one to 10, one to 20, or one to 25. In certain embodiments, n is 1, 2, 3, 4, 5, 6, 7, 8, 9, 10, 11, 12, 13, 14, 15, 16, 17, 18, 19, 20, 21, 22, 23, 24, or 25. In certain embodiments, n is 2, 3, 4, 5, or 6.

In certain embodiments, for the moiety of formula (IV) located on the 3' end of the oligonucleotide, n is an integer selected from one to 50, such as one to 10, one to 20, or one to 25. In certain embodiments, n is 1, 2, 3, 4, 5, 6, 7, 8, 9, 10, 11, 12, 13, 14, 15, 16, 17, 18, 19, 20, 21, 22, 23, 24, or 25. In certain embodiments, n is 2, 3, 4, 5, or 6.

In certain embodiments, the oligonucleotide comprises 3 to 30 (e.g., 3, 4, 5, 6, 7, 8, 9, 10, 11, 12, 13, 14, 15, 16, 17, 18, 19, 20, 21, 22, 23, 24, 25, 26, 27, 28, 29, or 30) contiguous nucleotides linked by phosphorothioate or phosphate intersubunit linkages located in between said moiety of formula (IV) located on the 5' end and said moiety of formula (IV) located on the 3' end of the oligonucleotide. In certain embodiments, the oligonucleotide comprises 3, 4, 5, or 6 contiguous nucleotides linked by phosphorothioate or phosphate intersubunit linkages.

In certain embodiments, the oligonucleotide comprises contiguous nucleotides linked by phosphorothioate intersubunit linkages located in between said moiety of formula (IV) located on the 5' end and said moiety of formula (IV) located on the 3' end of the oligonucleotide. In certain embodiments, the oligonucleotide comprises contiguous nucleotides linked by phosphate intersubunit linkages located in between said moiety of formula (IV) located on the 5' end and said moiety of formula (IV) located on the 3' end of the oligonucleotide. In certain embodiments, the oligonucleotide comprises contiguous nucleotides linked by intersubunit linkages comprising a mixture of phosphorothioate and phosphate linkages located in between said moiety of formula (IV) located on the 5' end and said moiety of formula (IV) located on the 3' end of the oligonucleotide.

In certain embodiments, a region of the moiety of formula (IV) is placed between two flanking regions of nucleotides linked by at least one intersubunit phosphorothioate or phosphate linkage. In certain embodiments, a region of the moiety of formula (IV) is placed between two flanking regions of nucleotides linked by intersubunit phosphorothioate linkages. In certain embodiments, a region of the moiety of formula (IV) is placed between two flanking regions of nucleotides linked by intersubunit phosphate linkages. In certain embodiments, a region of the moiety of formula (IV) is placed between two flanking regions of nucleotides linked by intersubunit linkages comprising a mixture of phosphorothioate and phosphate linkages.

In certain embodiments, the oligonucleotide comprises at least two contiguous nucleotides linked by a phosphorothioate or phosphate linkage located on the 5' end of the oligonucleotide; at least two contiguous nucleotides linked by a phosphorothioate or phosphate linkage located on the 3' end of the oligonucleotide; and the moiety of formula (IV) where n is 2 to 30 located in between said at least two contiguous nucleotides linked by phosphorothioate or phosphate linkages located on the 5' end and said at least two contiguous nucleotides linked by phosphorothioate or phosphate linkages located on the 3' end of the oligonucleotide.

In certain embodiments, the oligonucleotide comprises at least two contiguous nucleotides linked by phosphorothioate or phosphate linkages located on the 5' end of the oligonucleotide, wherein the contiguous nucleotides linked by phosphorothioate or phosphate linkage comprises one to 50 nucleotides. In certain embodiments, there are one to 10, one to 20, or one to 25 in the contiguous nucleotides linked by phosphorothioate or phosphate linkage. In certain embodiments, there are 1, 2, 3, 4, 5, 6, 7, 8, 9, 10, 11, 12, 13, 14, 15, 16, 17, 18, 19, 20, 21, 22, 23, 24, or 25 nucleotides linked by phosphorothioate or phosphate linkage. In certain embodiments, there are 2, 3, 4, 5, or 6 nucleotides linked by phosphorothioate or phosphate linkage.

In certain embodiments, the oligonucleotide comprises at least two contiguous nucleotides linked by phosphorothioate or phosphate linkages located on the 3' end of the oligonucleotide, wherein the contiguous nucleotides linked by phosphorothioate or phosphate linkage comprises one to 50 nucleotides. In certain embodiments, there are one to 10, one to 20, or one to 25 in the contiguous nucleotides linked by phosphorothioate or phosphate linkage. In certain embodiments, there are 1, 2, 3, 4, 5, 6, 7, 8, 9, 10, 11, 12, 13, 14, 15, 16, 17, 18, 19, 20, 21, 22, 23, 24, or 25 nucleotides linked by phosphorothioate or phosphate linkage. In certain embodiments, there are 2, 3, 4, 5, or 6 nucleotides linked by phosphorothioate or phosphate linkage.

In certain embodiments, the oligonucleotide comprises contiguous nucleotides linked by phosphorothioate intersubunit linkages located at the 5' end and the 3' end of the oligonucleotide. In certain embodiments, the oligonucleotide comprises contiguous nucleotides linked by phosphate intersubunit linkages located at the 5' end and the 3' end of the oligonucleotide. In certain embodiments, the oligonucleotide comprises contiguous nucleotides linked by phosphorothioate intersubunit linkages located at either the 5' end or the 3' end of the oligonucleotide and contiguous nucleotides linked by phosphate intersubunit linkages located at other end of the 5' end or the 3' end of the oligonucleotide. In certain embodiments, the oligonucleotide comprises contiguous nucleotides linked by intersubunit linkages comprising a mixture of phosphorothioate and phosphate linkages located at the 5' end and the 3' end of the oligonucleotide.

In certain embodiments, for the moiety of formula (IV), n is an integer selected from 2 to 30, such as 2, 3, 4, 5, 6, 7, 8, 9, 10, 11, 12, 13, 14, 15, 16, 17, 18, 19, 20, 21, 22, 23, 24, 25, 26, 27, 28, 29, or 30. In certain embodiments, n is 2, 3, 4, 5, or 6.

In certain embodiments, the oligonucleotide prevents translation of the mRNA by steric hindrance. In certain embodiments, the oligonucleotide is a substrate for RNase-H-mediated degradation of the mRNA from a gene.

Synthesis of Compounds

The embodiments are also directed to processes and intermediates useful for preparing subject compounds or a salt or solvate or stereoisomer thereof.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to formula (I).

Representative syntheses of compounds of the present disclosure are described in schemes below, and the particular examples that follow.

Scheme 1 shows a representative synthesis of the monomers used in the embodiments.

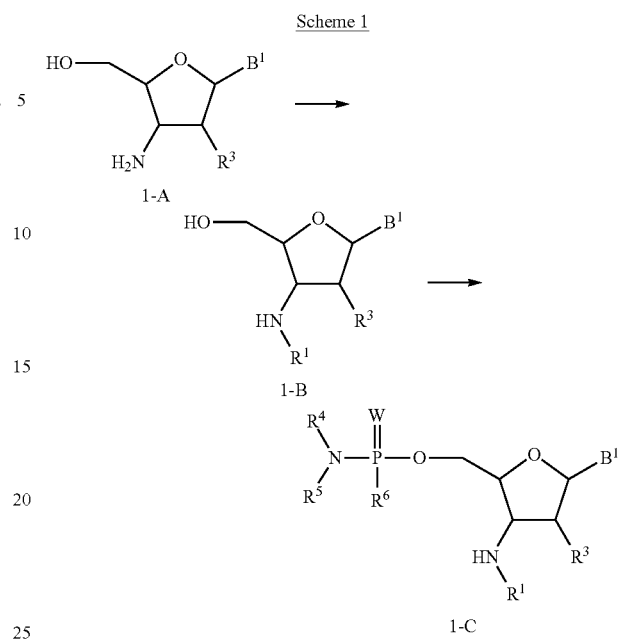

Scheme 1

In Scheme 1, $R^1$, $R^3$, $R^4$, $R^5$, $R^6$, W and $B^1$ are defined herein. Compounds 1-A and I-B are commercially available or can be synthesized by one of skill in the art.

In certain instances, Compound 1-A (a nucleoside with an amino group at the 3' position) is obtained. For example, 3'-amino-2',3'-dideoxy nucleosides, useful as starting materials in the syntheses herein, can be obtained commercially from Metkinen Oy, located in Littoinen, Finland. Various synthetic preparations of the 3'-amino-2',3'-dideoxy nucleosides have been reported in the literature (e.g. Zaitseva, G. V. et al., Nucleosides & Nucleotides 13(1-3):819-838 (1994); Cech, D. et al., Coll. Czech. Chem. Comm. 61:S297-S300 (1996); Zaitseva, V. E. et al., Sov. J. Bioorg. Chem. 10(5)5:369-378 (transl. from Bioorg. Khim. 10(5):670-680) (1984)). The moiety $R^1$ is a protecting group for 3' amino group and can be added to Compound 1-A with standard techniques to obtain Compound 1-B. Examples of preparation of a compound with an amino protecting group can be found in T. W. Greene and P. G. M. Wuts, "Protective Groups in Organic Synthesis," 4$^{th}$ ed., Wiley, New York 2006.

With further reference to Scheme 1, Compound 1-B is reacted with a phosphorylating reagent to obtain Compound 1-C. In certain embodiments, the phosphorylating reagent is dimethylamino-phosphoryl compound, such as dimethylamino-phosphorodichloridate. In certain embodiments, the phosphorylating reagent is thiophosphorodichloridate or selenophosphorodichloridate. The reaction can be run in presence of a base, such as 2,6-lutidine and N-methylimidazole.

Scheme 2 shows a representative synthesis of compounds of the embodiments.

Scheme 2

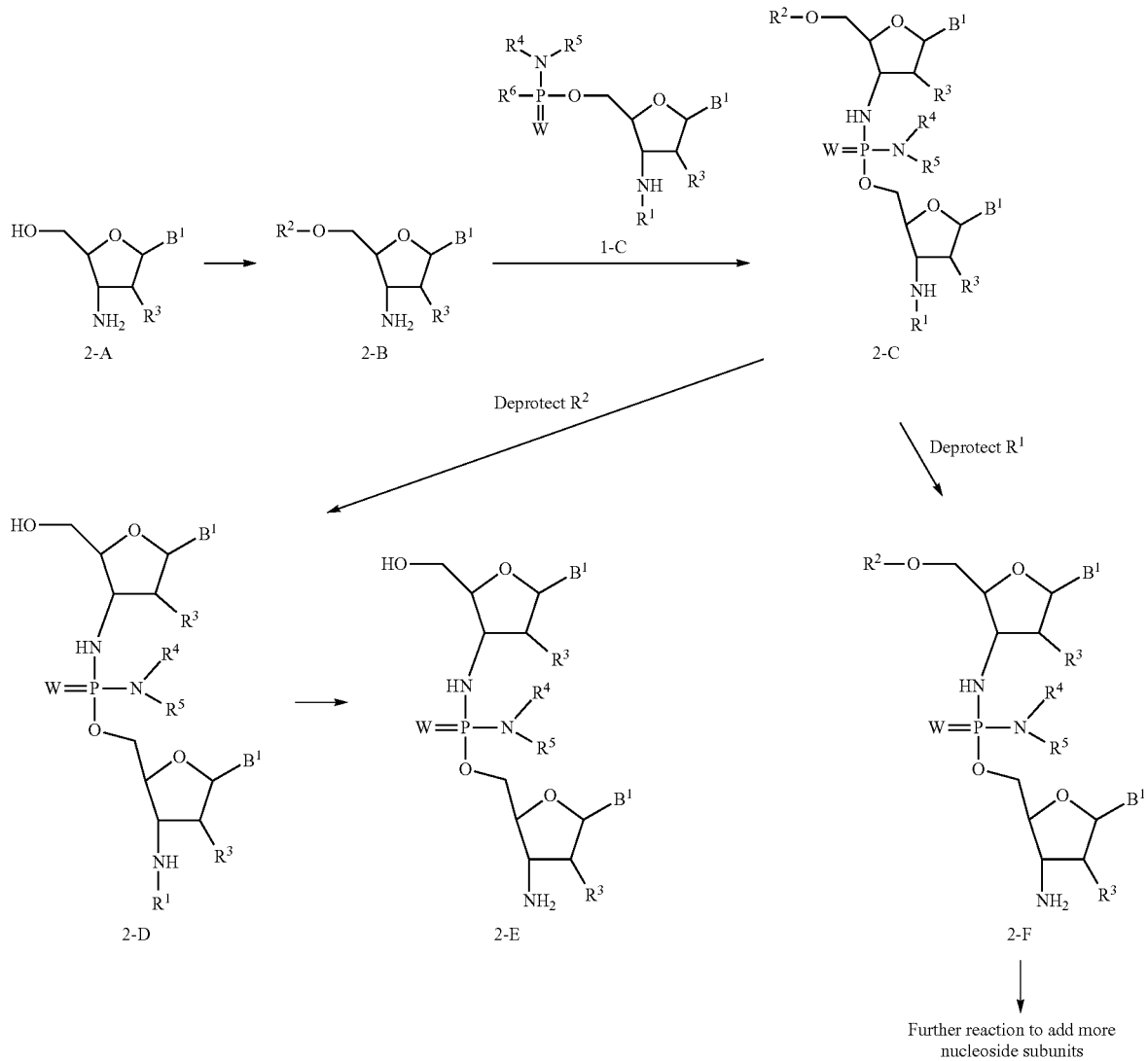

In Scheme 2, $R^1$, $R^2$, $R^3$, $R^4$, $R^5$, $R^6$, W, and $B^1$ are defined herein. Compounds 2-A and 2-B are commercially available or can be synthesized by one of skill in the art.

In certain instances, Compound 2-A (a nucleoside with an amino group at the 3' position) is obtained. The moiety $R^2$ is a protecting group for 5' hydroxyl group or a solid support and can be added to Compound 2-A with standard techniques to obtain Compound 2-B. Examples of preparation of a compound with a hydroxyl protecting group can be found in T. W. Greene and P. G. M. Wuts, "Protective Groups in Organic Synthesis," 4$^{th}$ ed., Wiley, New York 2006. In certain instances, $R^2$ is a base-labile protecting group. In certain instances, $R^2$ is a solid support. In certain instances, $R^2$ is a solid support that is base-labile (e.g., can be deblocked with base). Examples of suitable solid supports include, but are not limited to, slides, beads, chips, particles, strands, gels, sheets, tubing, spheres, containers, capillaries, pads, slices, films, plates and the like. In certain embodiments, a solid support may be biological, nonbiological, organic, inorganic, or any combination thereof. Suitable solid supports can be made out of glass or polymers. For example, suitable solid supports can be made out of polystyrene (such as polystyrene crosslinked with divinylbenzene), controlled pore glass (CPG), or TentaGel® (Sigma-Aldrich, St. Louis, Mo.).

With further reference to Scheme 2, Compound 2-B is reacted with Compound 1-C to obtain Compound 2-C. The amino group of Compound 2-B reacts with the phosphorus of Compound 1-C to displace the moiety $R^6$. In certain embodiments, the coupling reaction of Compound 2-B and Compound 1-C can be facilitated with the use of a halogen exchange agent, such as LiBr.

In one synthetic route, Compound 2-C can serve as a starting material for further addition of nucleoside subunits. In Compound 2-C, the moiety $R^1$ is an amino protecting group and can be acid labile (e.g., can be removed in the presence of acid, such as a weak acid). The moiety $R^1$ can be removed from Compound 2-C to provide Compound 2-F. In Compound 2-F, there is an amino group that can readily react with Compound 1-C to add another nucleoside subunit.

The reaction to add further nucleoside subunits can be repeated. Standard procedures for preparation of oligonucleotides can be used.

When an oligonucleotide is prepared via deprotection of moiety $R^1$ and addition of nucleoside subunits, the oligonucleotide of a specified length can be deprotected at the $R^1$, $R^2$ and $B^1$ moieties. As discussed above, the moiety $R^1$ is an amino protecting group and can be acid labile (e.g., can be removed in the presence of acid, such as a weak acid). The moiety $R^2$ is a hydroxyl protecting group or a solid support and can be base labile (e.g., can be removed in the presence of base). An example of a suitable base that can remove the moiety $R^2$ when $R^2$ is a hydroxyl protecting group includes tetra-n-butylammonium fluoride (TBAF). An example of a suitable base that can remove the moiety $R^2$ when $R^2$ is a solid support includes ammonium hydroxide ($NH_4OH$). If moiety $B^1$ comprises a protecting group during the synthesis, the protecting group can be removed. In certain instances, moiety $B^1$ comprises an amino protecting group that is base labile (e.g., can be removed in the presence of base).

In another synthetic route, Compounds 2-D and 2-E are obtained through an initial deprotection of the moiety $R^2$. The moiety $R^2$ is removed from Compound 2-C to provide Compound 2-D. Then, the moiety $R^1$ is removed from Compound 2-D to provide Compound 2-E. The moiety $R^2$ is a hydroxyl protecting group or a solid support and can be base labile (e.g., can be removed in the presence of base). An example of a suitable base that can remove the moiety $R^2$ when $R^2$ is a hydroxyl protecting group includes tetra-n-butylammonium fluoride (TBAF). An example of a suitable base that can remove the moiety $R^2$ when $R^2$ is a solid support includes ammonium hydroxide ($NH_4OH$). The moiety $R^1$ is an amino protecting group and can be acid labile (e.g., can be removed in the presence of acid, such as a weak acid).

Compound 2-D can serve as a starting material for further addition of nucleoside subunits. The 5'-hydroxyl group of Compound 2-D can be phosphitylated. Alternatively, the 5'-hydroxyl group of Compound 2-D can react with succinic acid and further react to be added to a solid support. After the 5'hydroxyl group is blocked, the $R^1$ moiety can be removed and expose an amino group for further reaction. The 3'-amine can react with Compound 1-C to add another nucleoside subunit. The reaction to add further nucleoside subunits can be repeated.

These methods can be performed by a variety of commercially-available automated oligonucleotide synthesizers.

The present disclosure provides for a method of preparing a compound of formula (II):

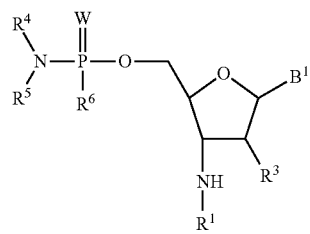

(II)

wherein
$R^1$ is hydrogen or an amino protecting group;
$R^3$ is independently selected from hydrogen, hydroxyl, and $-O-R^{3a}$;

wherein $R^{3a}$ is $C_{1-6}$ alkyl optionally substituted with $-NR^{3b}R^{3c}$, imidazolyl, $-(CH_2)_aO(CH_2)_bNR^{3b}R^{3c}$; or $-(CH_2)_aONR^{3d}(CH_2)_bNR^{3b}R^{3c}$;
wherein $R^{3b}$ is hydrogen or $C_{1-2}$ alkyl;
$R^{3c}$ is hydrogen or $C_{1-2}$ alkyl;
$R^{3d}$ is hydrogen or $C_{1-2}$ alkyl;
a is an integer selected from one to 4;
b is an integer selected from one to 4;
$R^4$ is $C_{1-6}$ alkyl optionally substituted with $-NR^{4a}R^{4b}$;
wherein $R^{4a}$ is hydrogen or $C_{1-2}$ alkyl and $R^{4b}$ is hydrogen or $C_{1-2}$ alkyl;
$R^5$ is $C_{1-6}$ alkyl optionally substituted with $-NR^{5a}R^{5b}$;
wherein $R^{5a}$ is hydrogen or $C_{1-2}$ alkyl and $R^{5b}$ is hydrogen or $C_{1-2}$ alkyl; or
$R^4$ and $R^5$ taken together with the nitrogen to which they are attached form an optionally substituted monocyclic heterocyclyl ring;
$R^6$ is a leaving group;
W is independently selected from O, S, and Se; and
$B^1$ is an optionally protected heterocyclic base moiety;
or a salt thereof;
wherein the method comprises:
contacting a compound of formula (A)

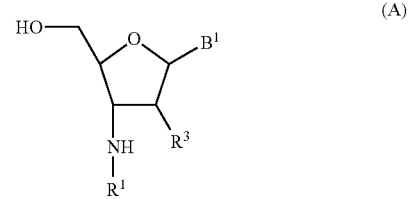

(A)

with a phosphorylating reagent.

In certain embodiments, the phosphorylating reagent is dimethylamino-phosphoryl compound. In certain embodiments, the phosphorylating reagent is dimethylamino-phosphorodichloridate. In certain embodiments, $R^1$ is an amino protecting group in formulae (A) and (II).

The present disclosure provides for a method of preparing a compound of formula (I):

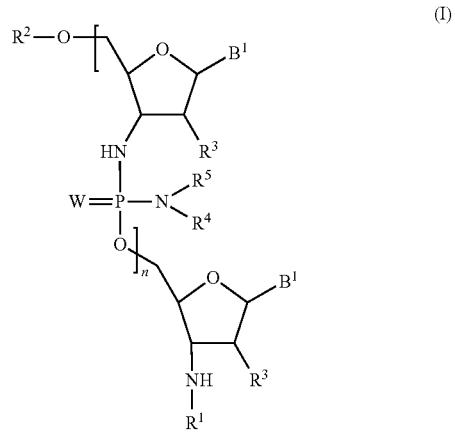

(I)

wherein
$R^1$ is hydrogen or an amino protecting group;
$R^2$ is hydrogen or a hydroxyl protecting group;
each $R^3$ is independently selected from hydrogen, hydroxyl, and $-O-R^{3a}$;

wherein each $R^{3a}$ is $C_{1-6}$ alkyl optionally substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$;
wherein each $R^{3b}$ is hydrogen or $C_{1-2}$ alkyl;
each $R^{3c}$ is hydrogen or $C_{1-2}$ alkyl;
each $R^{3d}$ is hydrogen or $C_{1-2}$ alkyl;
each a is an integer selected from one to 4;
each b is an integer selected from one to 4;
each W is independently selected from O, S, and Se;
each $B^1$ is independently selected from an optionally protected heterocyclic base moiety;
each $R^4$ is $C_{1-6}$ alkyl optionally substituted with —$NR^{4a}R^{4b}$;
wherein $R^{4a}$ is hydrogen or $C_{1-2}$ alkyl and $R^{4b}$ is hydrogen or $C_{1-2}$ alkyl;
each $R^5$ is $C_{1-6}$ alkyl optionally substituted with —$NR^{5a}R^{5b}$;
wherein $R^{5a}$ is hydrogen or $C_{1-2}$ alkyl and $R^{5b}$ is hydrogen or $C_{1-2}$ alkyl; or
$R^4$ and $R^5$ taken together with the nitrogen to which they are attached form an optionally substituted monocyclic heterocyclyl ring; and
n is an integer selected from one to 50;
or a salt thereof;
wherein the method comprises:
b) contacting a compound of formula (II)

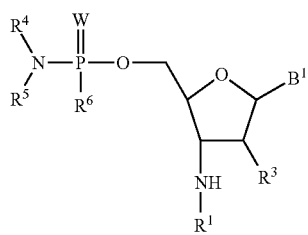

(II)

with a compound of formula (B):

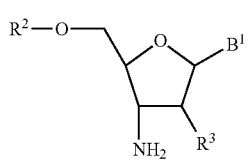

(B)

In certain embodiments, the mixing is performed in presence of a halogen exchange agent, such as LiBr. In certain embodiments, $R^1$ is an amino protecting group, and the method further comprises removing the amino protecting group. In certain embodiments, $R^2$ is a hydroxyl protecting group or a solid support, and the method further comprises removing the hydroxyl protecting group or solid support.

In certain embodiments, if moiety $B^1$ comprises a protecting group during the synthesis, the protecting group can be removed. In certain instances, moiety $B^1$ comprises an amino protecting group that is base labile (e.g., can be removed in the presence of base).

Isomers, Salts, Solvates, Protected Forms, and Prodrugs

In a compound of any of formulae (I)-(III) or the oligonucleotide comprising a moiety of formula (IV), there are linkages or moieties that comprise a chiral atom (e.g. phosphorus atom). Compositions comprising a compound of any of formulae (I)-(III) or the oligonucleotide comprising a moiety of formula (IV) can be prepared as a racemic mixture or enantiomerically enriched compositions of either enantiomer based on the chiral phosphorus atom. The term "enantiomerically enriched" refers to the racemic mixture (i.e., 50/50 mixture of the enantiomers) has been purified such that one enantiomer comprises greater than 50% of the total amount of the compound present.

In certain embodiments, a composition comprising a compound of any of formulae (I)-(III) or the oligonucleotide comprising a moiety of formula (IV) is a racemic mixture. In certain embodiments, a composition comprising a compound of any of formulae (I)-(III) or the oligonucleotide comprising a moiety of formula (IV) is an enantiomerically enriched composition.

A certain compound may exist in one or more particular geometric, optical, enantiomeric, diastereomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hydroxyazo, and nitro/aci-nitro.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein in a known manner.

Unless otherwise specified, a reference to a particular compound also includes ionic, salt, solvate (e.g., hydrate), protected forms, and prodrugs thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: formic, acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate: is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The terms "chemically protected form" or "protected form," as used herein, pertains to a compound in which one or more reactive functional groups are protected from undesirable chemical reactions, that is, are in the form of a protected or protecting group (also known as a masked or masking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)$CH_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—$CH_3$); an isobutyryl amide (—NHCO—CH($CH_3$)$_2$; a benzyloxy amide (—NHCO—O$CH_2C_6H_5$, —NH-Cbz); as a t-butoxy amide (—NHCO—OC($CH_3$)$_3$, —NH-Boc); a 2-biphenyl-2-propoxy amide (—NHCO—OC($CH_3$)$_2C_6H_4C_6H_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); as an amidino, for example, dimethylformamidino (—=CHN($CH_3$)$_2$) or diarylformamidino (—=CHN($C_6H_5$)$_2$), or in suitable cases (e.g., cyclic amines), as a nitroxide radical (>N—O.).

For example, a carboxylic acid group may be protected as an ester for example, as: an $C_{1-7}$alkyl ester (e.g., a methyl ester; a t-butyl ester); a $C_{1-7}$haloalkyl ester (e.g., a $C_{1-7}$trihaloalkyl ester); a tri$C_{1-7}$alkylsilyl-$C_{1-7}$alkyl ester; or a $C_{5-20}$aryl-$C_{1-7}$alkyl ester (e.g., a benzyl ester; a nitrobenzyl ester); or as an amide, for example, as a methyl amide.

Pharmaceutical Compositions

For therapeutic application, a compound of the embodiments is formulated in a therapeutically effective amount with a pharmaceutically acceptable carrier. One or more compounds may be included in any given formulation. The pharmaceutical carrier may be solid or liquid. Liquid carriers can be used in the preparation of solutions, emulsions, suspensions and pressurized compositions. The compounds are dissolved or suspended or diluted in a pharmaceutically acceptable solid, semi-solid, or liquid excipient, which acts as a vehicle, carrier or medium for the active ingredient. Suitable examples of liquid carriers for parenteral administration of the compounds include water (which may contain additives, e.g., cellulose derivatives, sodium carboxymethyl cellulose solution), phosphate buffered saline solution (PBS), alcohols (including monohydric alcohols and polyhydric alcohols, e.g., glycols) and their derivatives, and oils (e.g., fractionated coconut oil and arachis oil). The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators.

For parenteral administration of the compounds, the carrier can also be an oily ester such as ethyl oleate and isopropyl myristate. Sterile carriers are useful in sterile liquid form compositions for parenteral administration.

Sterile liquid pharmaceutical compositions, solutions or suspensions can be utilized by, for example, intraperitoneal injection, subcutaneous injection, intravenously, or topically. The compounds can also be administered intravascularly or via a vascular stent.

The liquid carrier for pressurized compositions can be a halogenated hydrocarbon or other pharmaceutically acceptable propellant. Such pressurized compositions may also be lipid encapsulated for delivery via inhalation. For administration by intranasal or intrabronchial inhalation or insufflation, the compounds may be formulated into an aqueous or partially aqueous solution, which can then be utilized in the form of an aerosol.

The compositions of the embodiments can also be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. The compounds may be administered topically as a solution, cream, or lotion, by formulation with pharmaceutically acceptable vehicles containing the active compound. Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the embodiments can be formulated so as to provide quick, sustained or delayed release of the active ingredient after administration to the patient by employing procedures known in the art.

In preparing a formulation, it may be necessary to mill the active lyophilized compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

These pharmaceutical compositions of the embodiments can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound. In some embodiments, the pharmaceutical compositions may be orally administered in any acceptable dosage including, but not limited to, formulations in capsules, tablets, powders or granules, and as suspensions or solutions in water or non-aqueous media. Pharmaceutical compositions and/or formulations comprising the compounds may include carriers, lubricants, diluents, thickeners, flavoring agents, emulsifiers, dispersing aids or binders. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

When employed as oral compositions, the compounds of the present embodiments can be protected from acid digestion in the stomach by a pharmaceutically acceptable protectant. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described supra. The compositions can be administered by the oral or nasal respiratory route for local or systemic effect. Compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder compositions can also be administered, orally or nasally, from devices which deliver the formulation in an appropriate manner.

While the compounds of the embodiments have superior characteristics for cellular and tissue penetration, they may be formulated to provide even greater benefit, for example in liposome carriers. The use of liposomes to facilitate cellular uptake is described, for example, in U.S. Pat. No. 4,897,355 and U.S. Pat. No. 4,394,448. Numerous publications describe the formulation and preparation of liposomes. The compounds can also be formulated by mixing with additional penetration enhancers, such as unconjugated forms of the lipid moieties described above, including fatty acids and their derivatives. Examples include oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.).

Complex formulations comprising one or more penetration enhancing agents may be used. For example, bile salts may be used in combination with fatty acids to make complex formulations. Exemplary combinations include chenodeoxycholic acid (CDCA), generally used at concentrations of about 0.5 to 2%, combined with sodium caprate or sodium laurate, generally used at concentrations of about 0.5 to 5%.

Pharmaceutical compositions and/or formulations comprising the compounds of the present embodiments may also include chelating agents, surfactants and non-surfactants. Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines). Surfactants include, for example, sodium lauryl sulfate, polyoxyethylene-9-lauryl ether and polyoxyethylene-20-cetyl ether; and perfluorochemical emulsions, such as FC-43. Non-surfactants include, for example, unsaturated cyclic ureas, 1-alkyl- and 1-alkenylazacyclo-alkanone derivatives, and non-steroidal anti-inflammatory agents such as diclofenac sodium, indomethacin and phenylbutazone.

Thus, in another aspect, there is provided a method of formulating a pharmaceutical composition, the method comprising providing a compound as described herein, and combining the compound with a pharmaceutically acceptable excipient. In certain embodiments, the compound is provided at pharmaceutical purity, as defined below. The method may further comprise adding to the compound, either before or after the addition of the excipient, a penetration enhancing agent.

The pharmaceutical composition will typically comply with pharmaceutical purity standards. For use as an active ingredient in a pharmaceutical preparation, a compound of the embodiments is generally purified away from other reactive or potentially immunogenic components present in the mixture in which they are prepared. Typically, to achieve pharmaceutical purity where a nucleic acid-based compound is the active ingredient, the active ingredient is provided in at least about 50% homogeneity, such as 60%, 70%, 80% or 90% homogeneity, as determined by functional assay, chromatography, or gel electrophoresis. The active ingredient is then compounded into a medicament in accordance with generally accepted procedures for the preparation of pharmaceutical preparations. Thus, in the present embodiments, providing the compounds at pharmaceutical purity requires that the compound be provided at least about 50% homogeneity, such at least 80% or 90% homogeneity.

The pharmaceutical composition will also typically be aliquoted and packaged in either single dose or multi-dose units. The dosage requirements for treatment with the compound vary with the particular compositions employed, the route of administration, the severity of the symptoms presented, the form of the compound and the particular subject being treated.

The compositions can be formulated in a unit dosage form, each dosage containing from about 5 mg to about 100 mg or more, such as any of about 1 mg to about 5 mg, 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, or about 1 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier.

The amount of compound per dose and the number of doses required to achieve such effects will vary depending on many factors including the disease indication, characteristics of the patient being treated and the mode of administration. Typically, the formulation and route of administration will provide a local concentration at the disease site of between 1 µM and 1 nM of the compound. In general, the compounds are administered at a concentration that affords effective results without causing any harmful or deleterious side effects. Such a concentration can be achieved by administration of either a single unit dose, or by the administration of the dose divided into convenient subunits at suitable intervals throughout the day. The compounds of the present embodiments are effective over a wide dosage range and are generally administered in a therapeutically effective amount. It will be understood, however, that the amount of the compounds actually administered will be determined by a physician, in the light of the relevant circumstances, including the condition to be treated, the chosen route of administration, the actual compound administered, the age, weight, and response of the individual patient, the severity of the patient's symptoms, and the like.

Methods

Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. The specific inhibitory effect has, therefore, been used by those skilled in the art for research uses. Antisense oligonucleotides have also been used as diagnostic aids based on their specific binding or hybridization to DNA or mRNA that are present in certain disease states and due to the high degree of sensitivity that hybridization based assays and amplified assays that utilize some of polymerase chain reaction afford.

The specificity and sensitivity of oligonucleotides is also used by those of skill in the art for therapeutic uses. They further can be used for treating organisms having a disease characterized by the undesired production of a protein. The organism can be contacted with a compound of the embodiments having a sequence that is capable of specifically hybridizing with a strand of nucleic acid that codes for the undesirable protein.

For example, the following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of Human Immunodeficiency Virus (HIV). U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to oligonucleotide analogs used to prevent replication of foreign nucleic acids in cells. U.S. Pat. No. 4,689,320 is directed to antisense oligonucleotides as antiviral agents specific to cytomegalovirus (CMV). U.S. Pat. No. 5,098,890 provides oligonucleotides complementary to at least a portion of the mRNA transcript of the human c-myb gene. U.S. Pat. No. 5,242,906 provides antisense oligonucleotides useful in the treatment of latent Epstein-Barr virus (EBV) infections.

In certain embodiments, the compounds disclosed herein can be used for the treatment and/or prevention of a cell proliferative disorder. In some embodiments, the individual is diagnosed with or is suspected of having a cell proliferative disorder. A "proliferative disorder" is any cellular disorder in which the cells proliferate more rapidly than normal tissue growth. Thus a "proliferating cell: is a cell that is proliferating more rapidly than normal cells. The proliferative disorder includes, but is not limited to, neoplasms. A "neoplasm" is an abnormal tissue growth, generally forming a distinct mass that grows by cellular proliferation more rapidly than normal tissue growth. Neoplasms show partial or total lack of structural organization and functional coordination with normal tissue. These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoetic structures (structures pertaining to the formation of blood cells) including components of the immune system, are called leukemias and lymphomas. A tumor is the neoplastic growth of the disease cancer. As used herein, a neoplasm, also referred to as a "tumor", is intended to encompass hematopoietic neoplasms as well as solid neoplasms.

In some embodiments, the disease is a cancer of any one of the following: basal cell carcinoma, medulloblastoma, glioblastoma, multiple myeloma, chronic myelogenous leukemia (CML), acute myelogenous leukemia, pancreatic cancer, lung cancer (small cell lung cancer and non-small cell lung cancer), esophageal cancer, stomach cancer, billary cancer, prostate cancer, liver cancer, hepatocellular cancer, gastrointestinal cancer, gastric cancer, and ovarian and bladder cancer. In some embodiments, the cancer is selected from the group consisting of pancreas ductal adenocarcinoma, colon adenocarcinoma, and ovary cystadenocarcinoma. In some embodiments, the cancer is pancreas ductal adenocarcinoma. In some embodiments, the cancer is a tumor that is poorly perfused and/or poorly vascularized.

In some embodiments, the cancer is pancreatic cancer, including for example pancreatic adenocarcinoma, pancreatic adenosquamous carcinoma, pancreatic squamous cell carcinoma, and pancreatic giant cell carcinoma. In some embodiments, the pancreatic cancer is exocrine pancreatic cancer. In some embodiments, the pancreatic cancer is endocrine pancreatic cancer (such as islet cell carcinoma). In some embodiments, the pancreatic cancer is advanced metastatic pancreatic cancer.

Other examples of cancers that can be treated by the methods of the invention include, but are not limited to, adenocortical carcinoma, agnogenic myeloid metaplasia, AIDS-related cancers (e.g., AIDS-related lymphoma), anal cancer, appendix cancer, astrocytoma (e.g., cerebellar and cerebral), basal cell carcinoma, bile duct cancer (e.g., extrahepatic), bladder cancer, bone cancer, (osteosarcoma and malignant fibrous histiocytoma), brain tumor (e.g., glioma, brain stem glioma, cerebellar or cerebral astrocytoma (e.g., pilocytic astrocytoma, diffuse astrocytoma, anaplastic (malignant) astrocytoma), malignant glioma, ependymoma, oligodenglioma, meningioma, craniopharyngioma, haemangioblastomas, medulloblastoma, supratentorial primitive neuroectodermal tumors, visual pathway and hypothalamic glioma, and glioblastoma), breast cancer, bronchial adenomas/carcinoids, carcinoid tumor (e.g., gastrointestinal carcinoid tumor), carcinoma of unknown primary, central nervous system lymphoma, cervical cancer, colon cancer, colorectal cancer, chronic myeloproliferative disorders, endometrial cancer (e.g., uterine cancer), ependymoma, esophageal cancer, Ewing's family of tumors, eye cancer (e.g., intraocular melanoma and retinoblastoma), gallbladder cancer, gastric (stomach) cancer, gastrointestinal carcinoid tumor, gastrointestinal stromal tumor (GIST), germ cell tumor, (e.g., extracranial, extragonadal, ovarian), gestational trophoblastic tumor, head and neck cancer, hepatocellular (liver) cancer (e.g., hepatic carcinoma and hepatoma), hypopharyngeal cancer, islet cell carcinoma (endocrine pancreas), laryngeal cancer, laryngeal cancer, leukemia, lip and oral cavity cancer, oral cancer, liver cancer, lung cancer (e.g., small cell lung cancer, non-small cell lung cancer, adenocarcinoma of the lung, and squamous carcinoma of the lung), lymphoid neoplasm (e.g., lymphoma), medulloblastoma, ovarian cancer, mesothelioma, metastatic squamous neck cancer, mouth cancer, multiple endocrine neoplasia syndrome, myelodysplastic syndromes, myelodysplastic/myeloproliferative diseases, nasal cavity and paranasal sinus cancer, nasopharyngeal cancer, neuroblastoma, neuroendocrine cancer, oropharyngeal cancer, ovarian cancer (e.g., ovarian epithelial cancer, ovarian germ cell tumor, ovarian low malignant potential tumor), pancreatic cancer, parathyroid cancer, penile cancer, cancer of the peritoneal, pharyngeal cancer, pheochromocytoma, pineoblastoma and supratentorial primitive neuroectodermal tumors, pituitary tumor, pleuropulmonary blastoma, lymphoma, primary central nervous system lymphoma (microglioma), pulmonary lymphangiomyomatosis, rectal cancer, renal cancer, renal pelvis and ureter cancer (transitional cell cancer), rhabdomyosarcoma, salivary gland cancer, skin cancer (e.g., non-melanoma (e.g., squamous cell carcinoma), melanoma, and Merkel cell carcinoma), small intestine cancer, squamous cell cancer, testicular cancer, throat cancer, thymoma and thymic carcinoma, thyroid cancer, tuberous sclerosis, urethral cancer, vaginal cancer, vulvar cancer, Wilms' tumor, and post-transplant lymphoproliferative disorder (PTLD), abnormal vascular proliferation associated with phakomatoses, edema (such as that associated with brain tumors), and Meigs' syndrome.

In some embodiments, the cancer is a solid tumor (such as advanced solid tumor). Solid tumor includes, but is not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Kaposi's sarcoma, soft tissue sarcoma, uterine sacronomasynovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma (including for example adenocarcinoma, clear cell renal cell carcinoma, papillary renal cell carcinoma, chromophobe renal cell carcinoma, collecting duct renal cell carcinoma, granular renal cell carcinoma, mixed granular renal cell carcinoma, renal angiomyolipomas, or spindle renal cell carcinoma.), hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In some embodiments the lymphoid neoplasm (e.g., lymphoma) is a B-cell neoplasm. Examples of B-cell neoplasms include, but are not limited to, precursor B-cell neoplasms (e.g., precursor B-lymphoblastic leukemia/lymphoma) and peripheral B-cell neoplasms (e.g., B-cell chronic lymphocytic leukemia/prolymphocytic leukemia/small lymphocytic lymphoma (small lymphocytic (SL) NHL), lymphoplasmacytoid lymphoma/immunocytoma, mantel cell lymphoma, follicle center lymphoma, follicular lymphoma (e.g., cytologic grades: I (small cell), II (mixed small and large cell), III (large cell) and/or subtype: diffuse and predominantly small cell type), low grade/follicular non-Hodgkin's lymphoma (NHL), intermediate grade/follicular NHL, marginal zone B-cell lymphoma (e.g., extranodal (e.g., MALT-type +/− monocytoid B cells) and/or Nodal (e.g., +/− monocytoid B cells)), splenic marginal zone lymphoma (e.g., +/− villous lymphocytes), Hairy cell leukemia, plasmacytoma/plasma cell myeloma (e.g., myeloma and multiple myeloma), diffuse large B-cell lymphoma (e.g., primary mediastinal (thymic) B-cell lymphoma), intermediate grade diffuse NHL, Burkitt's lymphoma, High-grade B-cell lymphoma, Burkitt-like, high grade immunoblastic NHL, high grade lymphoblastic NHL, high grade small non-cleaved cell NHL, bulky disease NHL, AIDS-related lymphoma, and Waldenstrom's macroglobulinemia).

In some embodiments the lymphoid neoplasm (e.g., lymphoma) is a T-cell and/or putative NK-cell neoplasm. Examples of T-cell and/or putative NK-cell neoplasms include, but are not limited to, precursor T-cell neoplasm (precursor T-lymphoblastic lymphoma/leukemia) and peripheral T-cell and NK-cell neoplasms (e.g., T-cell chronic lymphocytic leukemia/prolymphocytic leukemia, and large granular lymphocyte leukemia (LGL) (e.g., T-cell type and/or NK-cell type), cutaneous T-cell lymphoma (e.g., mycosis fungoides/Sezary syndrome), primary T-cell lymphomas unspecified (e.g., cytological categories (e.g., medium-sized cell, mixed medium and large cell), large cell, lymphoepitheloid cell, subtype hepatosplenic γδ T-cell lymphoma, and subcutaneous panniculitic T-cell lymphoma), angioimmunoblastic T-cell lymphoma (AILD), angiocentric lymphoma, intestinal T-cell lymphoma (e.g., +/− enteropathy associated), adult T-cell lymphoma/leukemia (ATL), anaplastic large cell lymphoma (ALCL) (e.g., CD30+, T- and null-cell types), anaplastic large-cell lymphoma, and Hodgkin's lymphoma).

In some embodiments the lymphoid neoplasm (e.g., lymphoma) is Hodgkin's disease. For example, the Hodgkin's disease can be lymphocyte predominance, nodular sclerosis, mixed cellularity, lymphocyte depletion, and/or lymphocyte-rich.

In some embodiments, the cancer is leukemia. In some embodiments, the leukemia is chronic leukemia. Examples of chronic leukemia include, but are not limited to, chronic myelocytic I (granulocytic) leukemia, chronic myelogenous, chronic myelomonocytic (CMML), and chronic lymphocytic leukemia (CLL). In some embodiments, the leukemia is acute leukemia. Examples of acute leukemia include, but are not limited to, acute lymphoblastic leukemia (ALL), acute myeloid leukemia, acute lymphocytic leukemia, and acute myelocytic leukemia (e.g., myeloblastic, promyelocytic, myelomonocytic, monocytic, and erythroleukemia).

In some embodiments, the cancer is myeloproliferative neoplasm or myelodysplastic syndrome. Examples of myeloproliferative neoplasm and myelodysplastic syndrome include, but are not limited to, essential thrombocythemia (ET), polycythemia vera (PV), and myelofibrosis (MF). In some embodiments, the compounds disclosed herein can be used to treat refractory anemia, refractory anemia with excess blasts, or refractory cytopenia.

In some embodiments, the cancer is liquid tumor or plasmacytoma. Plasmacytoma includes, but is not limited to, myeloma. Myeloma includes, but is not limited to, an extramedullary plasmacytoma, a solitary myeloma, and multiple myeloma. In some embodiments, the plasmacytoma is multiple myeloma.

In some embodiments, the cancer is multiple myeloma. Examples of multiple myeloma include, but are not limited to, IgG multiple myeloma, IgA multiple myeloma, IgD multiple myeloma, IgE multiple myeloma, and nonsecretory multiple myeloma. In some embodiments, the multiple myeloma is IgG multiple myeloma. In some embodiments, the multiple myeloma is IgA multiple myeloma. In some embodiments, the multiple myeloma is a smoldering or indolent multiple myeloma. In some embodiments, the multiple myeloma is progressive multiple myeloma. In some embodiments, multiple myeloma may be resistant to a drug, such as, but not limited to, bortezomib, dexamethasone (Dex-), doxorubicin (Dox-), and melphalan (LR).

A compound of the embodiments may be used to inhibit or reduce telomere elongation and/or proliferation of cells having telomerase activity by inhibition of telomerase, which is a ribonucleoprotein that catalyzes the addition of telomeric repeat sequences to chromosome ends.

The sequence for the oligonucleotide is selected such that it includes a region that is complementary to the sequence of the telomerase RNA, which is shown in Table 1 (SEQ ID NO:1). The region that is complementary to the telomerase RNA component may be targeted to any portion of the telomerase RNA, but particular regions of the telomerase RNA are certain targets for inhibitory oligonucleotides. One certain target region is the region spanning nucleotides 30-67 of SEQ ID NO:1, which includes the "template region," an 11 nucleotide region of sequence 5'-CUAAC-CCUAAC-3' that spans nucleotide 46-56 of SEQ ID NO:1. The template region functions to specify the sequence of the telomeric repeats that telomerase adds to the chromosome ends and is a factor for the activity of the telomerase enzyme (see Chen et al., Cell 100:503-514, 2000; Kim et al., Proc. Natl. Acad. Sci., USA 98(14):7982-7987, 2001). Compounds of the embodiments that contain an oligonucleotide moiety comprising a sequence complementary to all or part of the template region can be used. Another target region is the region spanning nucleotides 137-179 of hTR (see Pruzan et al., Nucl. Acids Research, 30:559-568, 2002). Within this region, the sequence spanning 141-153 is a target. PCT publication WO 98/28442 describes the use of oligonucleotides of at least 7 nucleotides in length to inhibit telomerase, where the oligonucleotides are designed to be complementary to accessible portions of the hTR sequence outside of the template region, including nucleotides 137-196, 290-319, and 350-380 of hTR.

TABLE 1

| Sequence of SEQ ID NO: 1 |
|---|
| ggguugcgga ggguggaccu gggaggggug guggccauuu uuugucuaac ccuaacugag 60 |
| aagggcguag gcgccgugcu uuugcucccc gcgcgcuguu uuucucgcug acuuucagcg 120 |
| ggcggaaaag ccucggccug ccgccuucca ccguucauuc uagagcaaac aaaaaauguc 180 |
| agcugcuggc ccguucgccc cucccgggga ccugcggcgg gucgccugcc cagcccccga 240 |
| accccgccug gaggccgcgg ucgcccggg gcuuccucgg aggcaccac ugccaccgcg 300 |
| aagaguuggg cucugucagc cgcgggucuc ucgggggcga gggcgagguu caggccuuuc 360 |
| aggccgcagg aagaggaacg gagcgagucc ccgcgcgcgg cgcgauuccc ugagcugugg 420 |
| gacgugcacc caggacucgg cucacacaug c |

In certain embodiments, oligonucleotide comprises a sequence selected from the group consisting of: GTTAGGGTTAG (SEQ ID NO. 2); TAGGGTTAGACAA (SEQ ID NO. 3); and CAGTTAGGGTTAG (SEQ ID NO. 4).

In these contexts, inhibition or reduction of telomere extension or cell proliferation refer to a lower level of the measured length or activity relative to a control experiment in which the enzyme or cells are not treated with a compound of the embodiments. In particular embodiments, the inhibition or reduction in the measured length or activity is at least a 10% reduction or inhibition. One of skill in the art will appreciate that reduction or inhibition of the measured length or activity of at least 20%, 50%, 75%, 90% or 100% may be used for particular applications. The ability of a compound of the embodiments to inhibit telomere elongation can be determined in a cell-free assay (referred to as a biochemical assay) and in cells.

Accordingly, provided herein are methods for inhibiting telomere elongation in a cell. In one embodiment, the method comprises contacting the cell with any of the compounds useful for inhibiting telomere elongation (including any of the pharmaceutical compositions) described herein. In some embodiments, the cell is a cancer cell.

Also provided herein are methods for shortening telomere length in a cell. In one embodiment, the method comprises contacting the cell with any of the compounds useful for inhibiting telomere elongation (including any of the pharmaceutical compositions) described herein. In some embodiments, the cell is a cancer cell.

Methods for measuring inhibition of telomere elongation and the use of such methods to determine the inhibitory activity of compounds are described herein. For example, the TRAP assay is a standard assay method for measuring telomerase activity in a cell extract system and has been widely used in the search for telomerase inhibiting compounds (Kim et al., *Science* 266:2011, 1997; Weinrich et al., *Nature Genetics* 17:498, 1997). The TRAP assay measures the amount of radioactive nucleotides incorporated into elongation products (polynucleotides) formed by nucleotide addition to a telomerase substrate or primer. The radioactivity incorporated can be measured as the intensity of a band on a detection screen (e.g., a Phosphorimager screen) exposed to a gel on which the radioactive products are separated. The TRAP assay is also described in detail in U.S. Pat. Nos. 5,629,154, 5,837,453 and 5,863,726, and its use in testing the activity of telomerase inhibitory compounds is described in various publications including WO 01/18015. In addition, the following kits are available commercially for research purposes for measuring telomerase activity: TRAPeze® XK Telomerase Detection Kit (Cat. s7707; Intergen Co., Purchase N.Y.); and TeloTAGGG Telomerase PCR ELISA plus (Cat. 2,013,89; Roche Diagnostics, Indianapolis Ind.). The TRAP assay can be used to measure the inhibition of telomere elongation rather than the inhibition of telomerase activity. If the present compounds are incorporated in the elongation products formed by nucleotide addition to a telomerase substrate or primer, they will stop or "cap" the elongation product so that additional nucleotides cannot be added to the elongation product. In this way the elongation product is not extended beyond the compound and the elongation products are only very short bands on a gel, rather than a ladder of different lengths of elongation products.

Another protocol for measuring the ability of compounds to inhibit telomere elongation in a biochemical assay is the direct (non-PCR based) cell-free telomerase assay, referred to as the "Flashplate assay", and described in Asai et al., *Cancer Research*, 63:3931-3939 (2003).

The ability of a compound of the embodiments to inhibit telomere elongation in cells may be determined by incubating the compound with telomerase-expressing cells for a defined period of time, and then determining the telomere length in the cells. Telomerase-expressing tumor cell lines that are suitable for such assays include HME50-5E human breast epithelial cells (provided by Dr. Jerry Shay, University of Texas Southwestern Medical Center), the ovarian tumor cell lines OVCAR-5 (MIISB, Milan) and SK-OV-3 (American Type Culture Collection, ATCC), human kidney carcinoma Caki-1 cells (Japanese Collection of Research Bioresources, JCRB), human lung carcinoma 1549 cells (ATCC), human epidermoid carcinoma A431 cells (JCRB), and human prostate cancer DU145 cells (ATCC).

The present disclosure also provides antisense oligonucleotides that effectively target and/or inhibit non-coding RNA, such as, for example, microRNA (miRNA) and short interfering RNA (siRNA).

Functional analyses of miRNAs have revealed that these small non-coding RNAs contribute to different physiological processes in animals, including developmental timing, organogenesis, differentiation, patterning, embryogenesis, growth control and programmed cell death. Examples of particular processes in which miRNAs participate include stem cell differentiation, neurogenesis, angiogenesis, hematopoiesis, and exocytosis (reviewed by Alvarez-Garcia and Miska, Development, 2005, 132, 4653-4662).

Links between miRNAs, including miRNA families and clusters, and human disease have been also been identified. Many miRNAs are de-regulated in primary human tumors. Moreover, many human miRNAs are located at genomic regions linked to cancer. Also, miRNAs can be used for modulation of immunoregulatory proteins, including cytokines, such as colony stimulatory factors (CSF).

The present disclosure also provides antisense oligonucleotides that can be effective in antisense therapy associated with certain conditions. Thus, compounds of the embodiments are highly useful in the prevention or treatment of chronic or acute inflammatory or autoimmune diseases, especially those associated with aberrant lymphocyte or monocyte accumulation such as chronic and acute inflammatory or autoimmune diseases, aberrant lymphocyte or monocyte accumulation, arthritis, juvenile idiopathic arthritis, rheumatoid arthritis, acute and chronic arthritis, asthma, atherosclerosis, diabetic nephropathy, inflammatory bowel disease, Crohn's disease, multiple sclerosis, nephritis, glomerulonephritis, pancreatitis, pulmonary fibrosis, psoriasis, restenosis, transplant rejection, early stages of allergic responses, inhibition of LTC4, to prevent AHR (airway hyper-responsiveness), tuberculosis infection and malignancy, stroke, castleman's disease, neoplasm, high-grade multiple myeloma, malignant mesotheliomas, paraneoplastic syndrome of mesotheliomas, immunosuppression, cachexia, thrombocytosis, amyloidosis, osteogenesis imperfect, homocystinuria, osteoporosis, osteopetrosis, inflammation of bone mass w arthritis and r. arthritis, periodontal disease, fibrous dysplasia, Paget's disease, chronic renal failure, endocrinopathies, hypercalcemia, deficiency states, malabsorption syndromes, chronic liver disease, cancer metastasis, mammary tumor progression to metastasis, muscular dystrophy (such as Duchenne muscular dystrophy), cardiovascular disease, hypercholesterolemia, hypertriglyceridemia, coronary artery disease, clotting disorders, hyperlipidemia, metabolic disorders, diabetes, obesity, nonalcoholic steatohepatitis (NASH), inflammatory disorders, local fibrosis, ocular disease, anemia of chronic disease (ACD), pouchitis, TTR amyloidosis, spinal muscular dystrophy, severe hyperglyceridemia (HTG), acromegaly, Cushing's Syndrome, hereditary angioedema, and myelofibrosis.

The present disclosure also provides antisense oligonucleotides that effectively act as catalytic RNA, such as ribozyme. As such, the oligonucleotides of the embodiments can be capable of performing specific biochemical reactions, similar to the action of protein enzymes.

Combination Therapy

In some aspects, any of the methods disclosed herein can further comprise administering to the individual a therapeutically effective amount (such as any of the therapeutically effective amounts described above) of one or more additional anticancer therapeutic agents in addition to any of the c-myc antisense oligonucleotides disclosed herein (such as in a pharmaceutical composition). Various classes of anticancer agents can be used. Non-limiting examples include: alkylating agents, antimetabolites, anthracyclines, plant alkaloids, topoisomerase inhibitors, podophyllotoxin, antibodies (e.g., monoclonal or polyclonal), tyrosine kinase inhibitors (e.g., imatinib mesylate (Gleevec® or Glivec®)), hormone treatments, soluble receptors and other antineoplastics.

Topoisomerase inhibitors are also another class of anticancer agents that can be used. Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecins: irinotecan and topotecan. Examples of type II inhibitors include amsacrine, etoposide, etoposide phosphate, and teniposide. These are semisynthetic derivatives of epipodophyllotoxins, alkaloids naturally occurring in the root of American Mayapple (*Podophyllum peltatum*).

Antineoplastics include the immunosuppressant dactinomycin, doxorubicin, epirubicin, bleomycin, mechlorethamine, cyclophosphamide, chlorambucil, ifosfamide. The antineoplastic compounds generally work by chemically modifying a cell's DNA.

Alkylating agents can alkylate many nucleophilic functional groups under conditions present in cells. Cisplatin and carboplatin, and oxaliplatin are alkylating agents. They impair cell function by forming covalent bonds with the amino, carboxyl, sulfhydryl, and phosphate groups in biologically important molecules.

*Vinca* alkaloids bind to specific sites on tubulin, inhibiting the assembly of tubulin into microtubules (M phase of the cell cycle). The *vinca* alkaloids include: vincristine, vinblastine, vinorelbine, and vindesine.

Anti-metabolites resemble purines (azathioprine, mercaptopurine) or pyrimidine and prevent these substances from becoming incorporated in to DNA during the "S" phase of the cell cycle, stopping normal development and division. Anti-metabolites also affect RNA synthesis.

Plant alkaloids and terpenoids are derived from plants and block cell division by preventing microtubule function. Since microtubules are vital for cell division, without them, cell division cannot occur. The main examples are *vinca* alkaloids and taxanes. Podophyllotoxin is a plant-derived compound which has been reported to help with digestion as well as used to produce two other cytostatic drugs, etoposide and teniposide. They prevent the cell from entering the G1 phase (the start of DNA replication) and the replication of DNA (the S phase). Taxanes as a group includes paclitaxel and docetaxel. Paclitaxel is a natural product, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

Kits

The present disclosure provides a pharmaceutical pack or kit comprising one or more containers comprising a compound of any of formula (I)-(III) or oligonucleotide comprising moiety of formula (IV).

The present disclosure also provides a pharmaceutical pack or kit comprising one or more containers comprising one or more of the ingredients of the pharmaceutical compositions of the present embodiments. Optionally associated with such container(s) can be a notice in the form prescribed by a governmental agency regulating the manufacture, use or sale of pharmaceuticals or biological products, which notice reflects approval by the agency of manufacture, use or sale for human administration.

EXAMPLES

The following Examples illustrate the synthesis and activities of compounds of the embodiments.

Example 1

General Procedure for the Synthesis of Dimethylamino-Phosphorochloridate Monomers The scheme for synthesizing dimethylamino-phosphorochloridate monomers is shown in the scheme below.

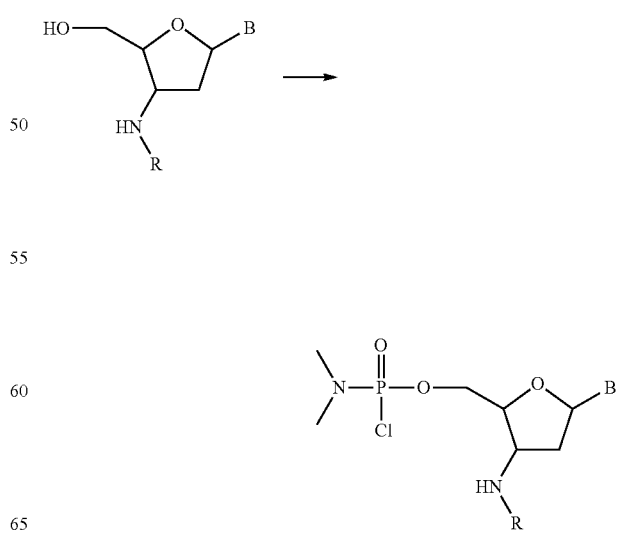

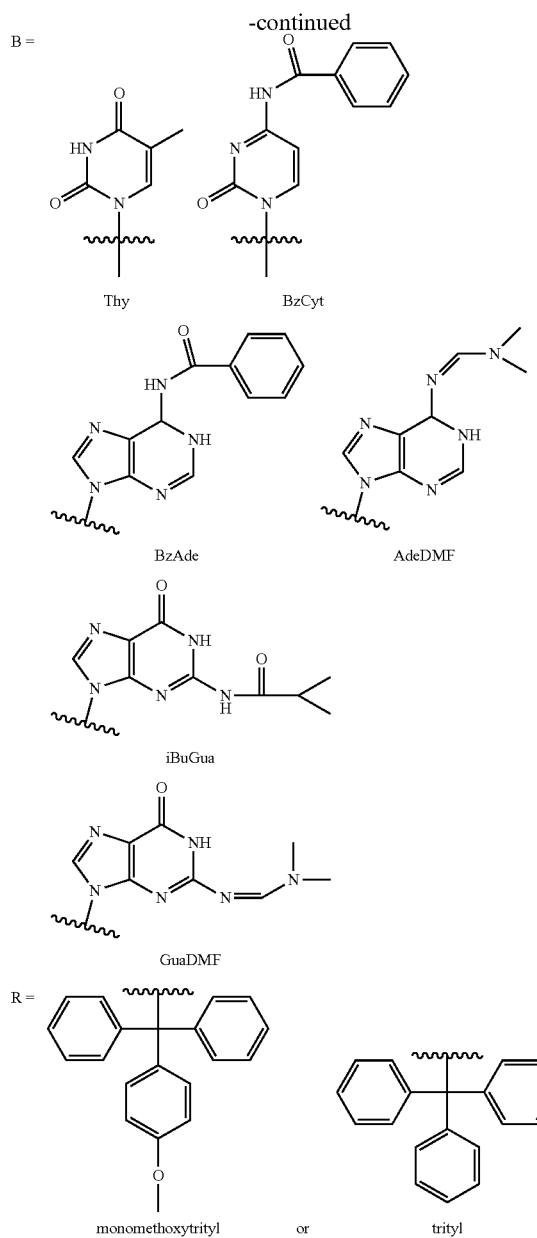

Seven mmol of the 5'-hydroxyl protected 3'-aminonucleoside was dissolved in 30-100 ml dry dichloromethane. Fourteen mmol of 2,6-Lutidine and 7 mmol of N-methylimidazole was added and the solution or suspension was cooled to 0° C. Fourteen mmol of dimethylamino-phosphorodichloridate was added dropwise over 5 minutes. The reaction mixture was allowed to warm up to room temperature and stirred for 1-2 hours. The reaction was followed by TLC using dichloromethane/methanol 9:1 solvent system. After the disappearance of the starting material, the reaction mixture was loaded on a silica gel column prepared with chloroform/acetone 95:5. The acetone content was gradually increased to 25%. The two isomers of the product was collected and evaporated in vacuo. The yield of the reaction after chromatography was 40-70%.

MMTr-Thymidine monomer: $^{31}$P NMR (CD$^3$CN): 18.130, 17.775 ppm

N$^6$-Bz-3'-NH-Tr-2'-deoxy-Adenosine monomer: $^{31}$P NMR (CD$^3$CN): 17.937, 17.480 ppm N$^2$-iBu-3'-NH-Tr-2'-deoxy-Guanosine monomer: $^{31}$P NMR (CD$^3$CN): 18.514, 17.998 ppm N$^4$-Bz-3'-NH-Tr-2'-deoxy-Cytidine monomer: $^{31}$P NMR (CD$^3$CN): 18.194, 17.685 ppm N$^6$-DMF-3'-NH-Tr, 2'-deoxy-Adenosine monomer: $^{31}$P NMR (CD$^3$CN): 18.335, 17.924 ppm $^1$H NMR (CD$^3$CN): The resonances of the methyl groups in the dimethyl-amino moiety of the mixture of the two isomers are detected between 2.5-2.8 ppm.

Mass spectrometry: the molecular weights of the compounds were confirmed by ES MS in the positive ion mode.

Example 2

Synthesis of Dimer on Solid Phase

The procedure for synthesizing a thymidine-adenosine dimer protected with trityl group is described below.

The default 1 µmol synthesis cycle on an Applied BioSystems (Foster City, Calif.) DNA synthesizer was modified as follows: the wait for the coupling was set to 60 minutes, the oxidation step was deleted, and after the deblocking step, 5% DIEA solution in dichloromethane from the vessel usually containing the oxidizer was delivered to the column for 5 seconds. The monomer was a 0.2 M solution in dichloromethane. The activator vessel contained 0.6 M solution of diisopropylamino-ethanol. The deblock solution was 5% cyanoacetic acid in dichloromethane containing 10% trifluoroethanol.

The synthesis column contained approximately 1 µmol 3'-aminotrityl-CPG. The synthesis column was heated with a heating tape to 40° C.

At the end of the cycle, the dimer was deblocked using ethanol-cc. ammonia 1:2 for 1 hour at 55° C.

The two isomers of the product eluted at 17.0 and 17.3 minutes respectively using a linear gradient of acetonitrile in 50 mM of triethylammonium acetate to 90% in 30 min; flow rate: 1 ml/min.

$^{31}$P NMR (D$_2$O): 18.613, 18.478 ppm

Example 3

Synthesis of Compound C

The procedure for synthesizing a thymidine-thymidine dimer protected with trityl group and t-butyl-dimethylsilyl group (Compound C) is described below.

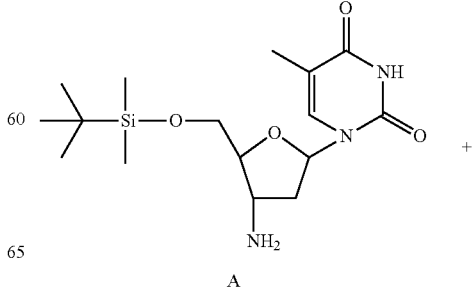

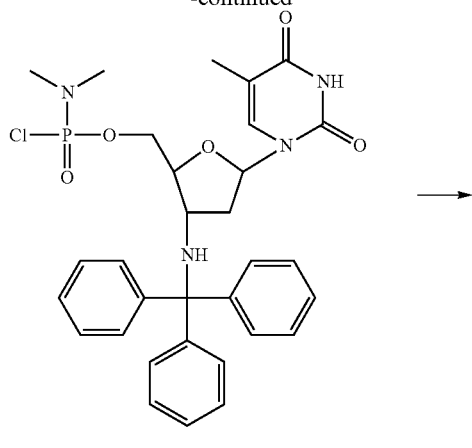

B

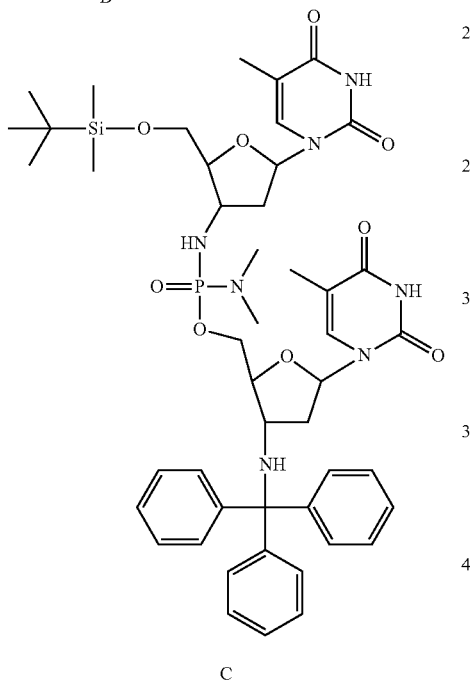

C 1.2 g (3.38 mmols, 1.2 eqs) of Compound B was dissolved in a mixture of $CH_3CN/DCM$ (15 ml/10 ml) and 1.2 mL (6.76 mmol, 2.2 eqs) of DIPEA was added to it followed by 1.7 g (2.81 mmol, 1 eq) of Compound A. To this mixture was added 500 mg (6.76 mmol, 2.2 eq.) of LiBr and the reaction mixture stirred for 30 minutes. The TLC showed complete consumption of 1 at which time the solvents were evaporated and the residue was dissolved in dichloromethane and washed with $2\times H_2O$, $1\times$ brine, dried over $Na_2SO_4$, filtered and evaporated. Crude yield was 2.7 grams (quant.). The HPLC and the LC-MS trace corresponded to Compound C.

The HPLC trace for Compound A: Compound A eluted at 13.8 minutes.

The HPLC trace for crude product eluted at 15.2 and 17.9 minutes

The HPLC trace for Compound C: Isomers of compound C eluted at 17.4 and 17.6 minutes.

The LC-MS spectrum for Compound C showed the mass was 926 (M-1).

Example 4

Synthesis of Compound D

The procedure for 5' TBDMS deprotection of a thymidine-thymidine dimer protected with trityl group and t-butyl-dimethylsilyl group to form Compound D is described below.

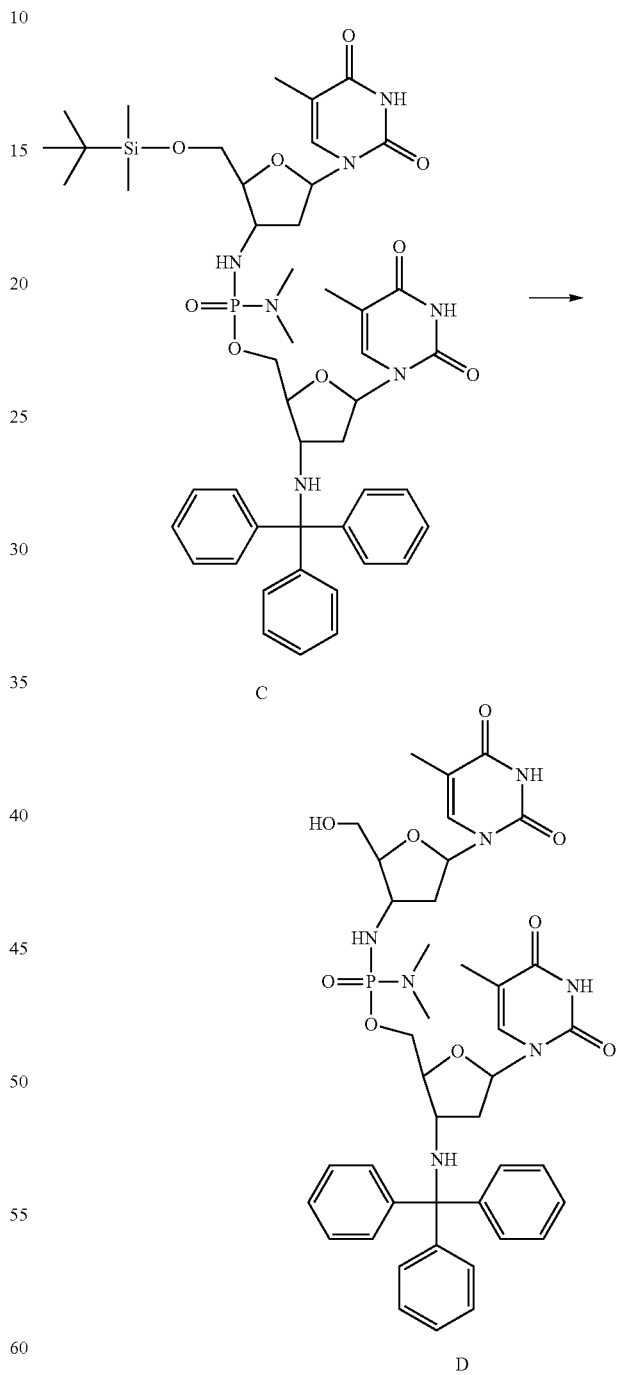

C

D

To 2.7 g (3.0 mmol) of Compound C was added 20 ml of 1M solution of TBAF/THF and the reaction mixture was stirred for 2 hours at which point the TLC showed the reaction to be complete. The solvents were evaporated and the residue was dissolved in dichloromethane and purified by flash chromatography. The purified yield of Compound D was 2.3 g (85%). The HPLC and the LC-MS trace corresponded to Compound D.

The HPLC trace for Compound D: showed that the two isomers eluted at 12.82 and 13.01 minutes.

The LC-MS spectrum for Compound D showed that the two isomers possessed identical mass values of 812 (M-1).

Example 5

Synthesis of Compound E

The procedure for 3'-NH detritylation of a thymidine-thymidine dimer protected with trityl group to form Compound E is described below.

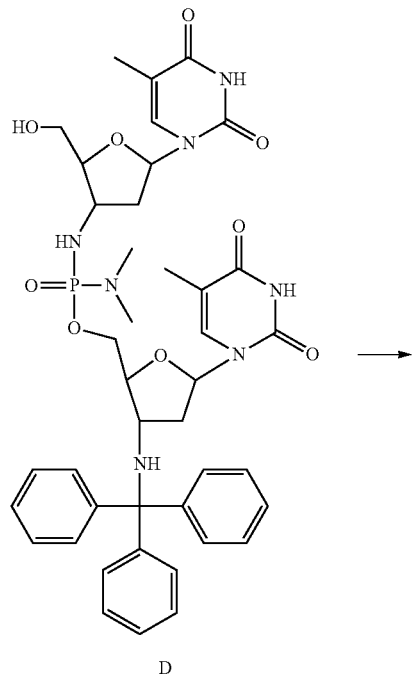

D

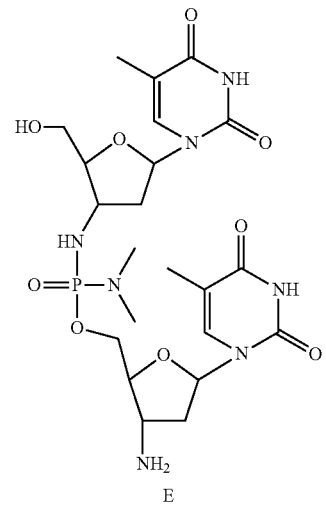

E

To 300 mg (0.33 mmols) of Compound D was added 0.5 ml of 4% cyanoacetic acid and the reaction mixture was stirred for 5 minutes and cooled in an ice bath and neutralized with triethylamine. The solvent was evaporated and the crude mixture was purified by RP-HPLC. Yield 150 mg (80% yield). The HPLC, LC-MS trace and $P^{31}$ NMR corresponded to Compound E.

The HPLC trace for Compound E showed that the two isomers eluted at 8.66 and 8.92 minutes.

The LC-MS spectrum for Compound E showed that the two isomers had an identical mass value of 570 (M-1).

The $^{31}$P NMR spectrum for Compound E in $D_2O$ (δ, ppm): 18.733, 18.822.

HPLC column and method: Hyperclone 5 μM, ODS C18, 4.6×250 mm. Linear gradient of acetonitrile in 50 mM of triethylammonium acetate to 90% in 30 min; flow rate: 1 ml/min.

What is claimed as new and desired to be protected by Letters Patent of the United States is:

1. A compound of formula (I):

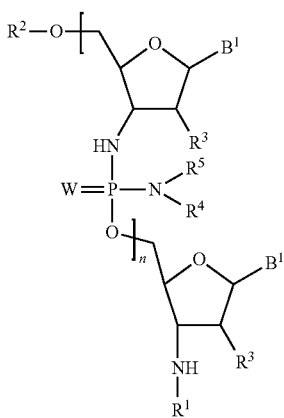

(I)

wherein $R^1$ is hydrogen, an amino protecting group, or an oligonucleotide;

$R^2$ is hydrogen, a hydroxyl protecting group, solid support, or an oligonucleotide;

each $R^3$ is independently selected from hydrogen, hydroxyl, and —O—$R^{3a}$;

wherein each $R^{3a}$ is $C_{1-6}$ alkyl or $C_{1-6}$ alkyl substituted with —$NR^{3b}R^{3c}$, imidazolyl, —$(CH_2)_aO(CH_2)_bNR^{3b}R^{3c}$, or —$(CH_2)_aONR^{3d}(CH_2)_bNR^{3b}R^{3c}$;

wherein each $R^{3b}$ is hydrogen or $C_{1-2}$ alkyl;

each $R^{3c}$ is hydrogen or $C_{1-2}$ alkyl;

each $R^{3d}$ is hydrogen or $C_{1-2}$ alkyl;

each a is an integer selected from one to 4;

each b is an integer selected from one to 4;

each $R^4$ is independently $C_{1-6}$ alkyl or $C_{1-6}$ alkyl substituted with —$NR^{4a}R^{4b}$;

wherein $R^{4a}$ is hydrogen or $C_{1-2}$ alkyl and $R^{4b}$ is hydrogen or $C_{1-2}$ alkyl;

each $R^5$ is independently $C_{1-6}$ alkyl or $C_{1-6}$ alkyl substituted with —$NR^{5a}R^{5b}$;

wherein $R^{5a}$ is hydrogen or $C_{1-2}$ alkyl and $R^{5b}$ is hydrogen or $C_{1-2}$ alkyl; or $R^4$ and $R^5$ taken together with the nitrogen to which they are attached form a monocyclic heterocyclyl or a monocyclic heterocyclyl substituted with $C_{1-6}$ alkyl, sperminyl, or spermidinyl;

each W is independently selected from O, S, and Se;

each $B^1$ is independently selected from a heterocyclic base moiety or a protected heterocyclic base moiety; and n is an integer selected from one to 50;

or a salt thereof.

2. The compound of claim 1, or a salt thereof, wherein each W is O.

3. The compound of claim 1, or a salt thereof, wherein each $B^1$ is independently selected from purinyl and pyrimidinyl.

4. The compound of claim 1, or a salt thereof, wherein each $B^1$ is independently selected from 4-benzoyl-1-cytosinyl, 6-benzoyl-9-adeninyl, 6-dimethylformamidino-9-adeninyl, 2-isobutyryl-9-guaninyl, 2-dimethylformamidino-9-guaninyl, 9-adeninyl, 9-guaninyl, 1-cytosinyl, 1-thyminyl and 1-uracilyl.

5. The compound of claim 1, or a salt thereof, wherein n is an integer from 2 to 30.

6. A compound of claim 1, wherein the compound comprises a sequence which includes a region that is complementary to any portion of a sequence of a telomerase RNA (SEQ ID NO:1).

7. The compound of claim 1, or a salt thereof, wherein n is an integer from 6 to 30.

8. A pharmaceutical composition comprising a compound of claim 1, or a pharmaceutically acceptable salt thereof, and a pharmaceutically acceptable carrier.

9. A kit comprising a compound of claim 1, or a salt thereof.

10. A compound of formula (III)

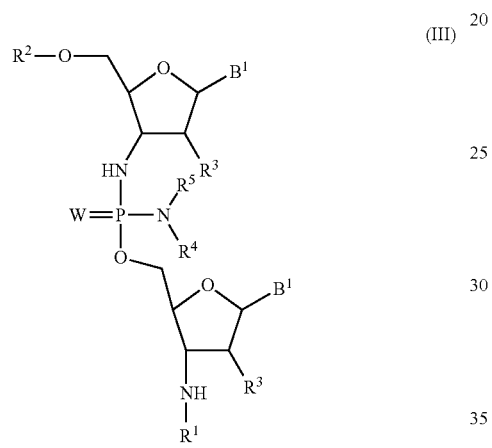

wherein
R$^1$ is hydrogen or an amino protecting group;
R$^2$ is hydrogen, a hydroxyl protecting group, or solid support;
each R$^3$ is independently selected from hydrogen, hydroxyl, and —O—R$^{3a}$;
  wherein each R$^{3a}$ is C$_{1-6}$ alkyl or C$_{1-6}$ alkyl substituted with —NR$^{3b}$R$^{3c}$, imidazolyl, —(CH$_2$)$_a$O(CH$_2$)$_b$NR$^{3b}$R$^{3c}$, or —(CH$_2$)$_a$ONR$^{3d}$(CH$_2$)$_b$NR$^{3b}$R$^{3c}$;
  wherein each R$^{3b}$ is hydrogen or C$_{1-2}$ alkyl;
  each R$^{3c}$ is hydrogen or C$_{1-2}$ alkyl;
  each R$^{3d}$ is hydrogen or C$_{1-2}$ alkyl;
  each a is an integer selected from one to 4;
  each b is an integer selected from one to 4;
each R$^4$ is C$_{1-6}$ alkyl or C$_{1-6}$ alkyl substituted with —NR$^{4a}$R$^{4b}$;
  wherein R$^{4a}$ is hydrogen or C$_{1-2}$ alkyl and R$^{4b}$ is hydrogen or C$_{1-2}$ alkyl;
each R$^5$ is C$_{1-6}$ alkyl or C$_{1-6}$ alkyl substituted with —NR$^{5a}$R$^{5b}$;
  wherein R$^{5a}$ is hydrogen or C$_{1-2}$ alkyl and R$^{5b}$ is hydrogen or C$_{1-2}$ alkyl; or
R$^4$ and R$^5$ taken together with the nitrogen to which they are attached form a monocyclic heterocyclyl or a monocyclic heterocyclyl substituted with C$_{1-6}$ alkyl, sperminyl or spermidinyl;
each W is independently selected from O, S, and Se; and
each B$^1$ is independently selected from a heterocyclic base moiety and a protected heterocyclic base moiety; or a salt thereof.

11. The compound of claim 10, or a salt thereof, wherein W is O.

12. The compound of claim 10, or a salt thereof, wherein each B$^1$ is independently selected from purinyl and pyrimidinyl.

13. The compound of claim 10, or a salt thereof, wherein each B$^1$ is independently selected from 4-benzoyl-1-cytosinyl, 6-benzoyl-9-adeninyl, 6-dimethylformamidino-9-adeninyl, 2-isobutyryl-9-guaninyl, 2-dimethylformamidino-9-guaninyl, 9-adeninyl, 9-guaninyl, 1-cytosinyl, 1-thyminyl and 1-uracilyl.

14. The compound of claim 10, or a salt thereof, wherein R$^2$ is a hydroxyl protecting group or a solid support.

15. The compound of claim 10, or a salt thereof, wherein the compound is selected from:

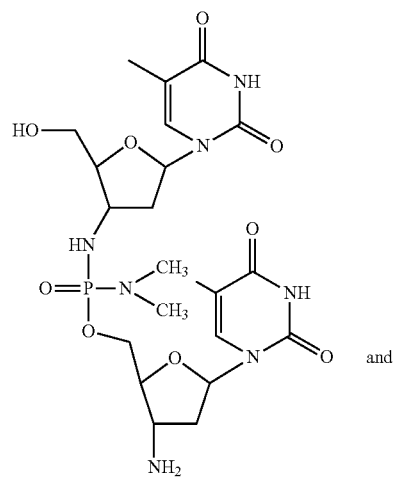 and

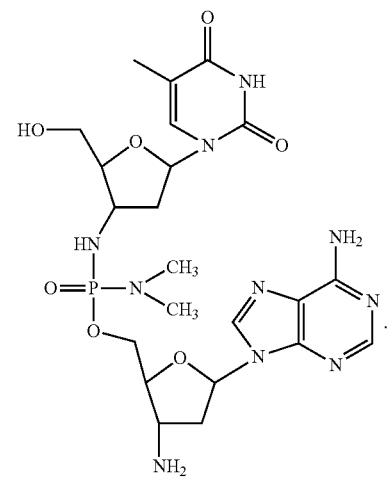

16. An oligonucleotide, wherein the nucleoside subunits of the oligonucleotide are joined by intersubunit linkages, wherein at least one of the intersubunit linkages is a phosphorothioate or phosphate diester linkage, and wherein the oligonucleotide has formula (I)

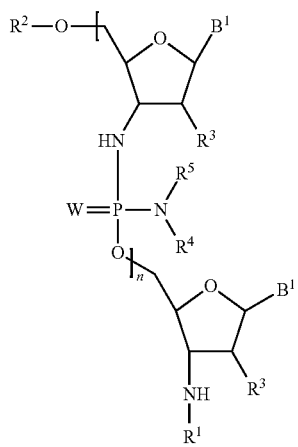

wherein
R$^1$ is selected from hydrogen and an oligonucleotide;
R$^2$ is selected from hydrogen and an oligonucleotide;
each R$^3$ is independently selected from hydrogen, hydroxyl, and —O—R$^{3a}$;
  wherein each R$^{3a}$ is C$_{1-6}$ alkyl or C$_{1-6}$ alkyl substituted with —NR$^{3b}$R$^{3c}$, imidazolyl, —(CH$_2$)$_a$O(CH$_2$)$_b$NR$^{3b}$R$^{3c}$, or —(CH$_2$)$_a$ONR$^{3d}$ (CH$_2$)$_b$NR$^{3b}$R$^{3c}$;
  wherein each R$^{3b}$ is hydrogen or C$_{1-2}$ alkyl;
  each R$^{3c}$ is hydrogen or C$_{1-2}$ alkyl;
  each R$^{3d}$ is hydrogen or C$_{1-2}$ alkyl;
  each a is an integer selected from one to 4;
  each b is an integer selected from one to 4;
each R$^4$ is independently C$_{1-6}$ alkyl or C$_{1-6}$ alkyl substituted with —NR$^{4a}$R$^{4b}$;
  wherein R$^{4a}$ is hydrogen or C$_{1-2}$ alkyl and R$^{4b}$ is hydrogen or C$_{1-2}$ alkyl;
each R$^5$ is independently C$_{1-6}$ alkyl or C$_{1-6}$ alkyl substituted with —NR$^{5a}$R$^{5b}$;
  wherein R$^{5a}$ is hydrogen or C$_{1-2}$ alkyl and R$^{5b}$ is hydrogen or C$_{1-2}$ alkyl; or
R$^4$ and R$^5$ taken together with the nitrogen to which they are attached form a monocyclic heterocyclyl or a monocyclic heterocyclyl substituted with C$_{1-6}$ alkyl, sperminyl or spermidinyl;
each W is independently selected from O, S, and Se;
each B$^1$ is independently selected from a heterocyclic base moiety or a protected heterocyclic base moiety; and
n is an integer selected from one to 25;
or a salt thereof.

17. The oligonucleotide of claim 16, or a salt thereof, wherein:
R$^1$ is H; and
R$^2$ is an oligonucleotide which comprises a central region comprising intersubunit linkages independently selected from phosphorothioate and phosphate diester linkages joined to a terminal 5'-flanking region having the formula:

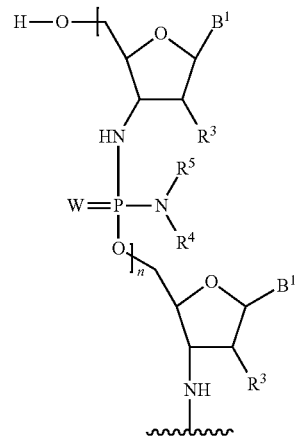

wherein each n is independently an integer selected from one to 25.

18. The oligonucleotide of claim 16, or a salt thereof, wherein:
R$^1$ is an oligonucleotide comprising intersubunit linkages independently selected from phosphorothioate and phosphate esters; and
R$^2$ is an oligonucleotide comprising intersubunit linkages independently selected from phosphorothioate and phosphate esters.

19. The oligonucleotide of claim 16, or a salt thereof, wherein the oligonucleotide prevents translation of the mRNA by steric hindrance.

20. The oligonucleotide of claim 16, or a salt thereof, wherein the oligonucleotide is a substrate for RNase-H-mediated degradation of the mRNA from a gene.

21. An oligonucleotide of claim 16, wherein the oligonucleotide comprises a sequence which includes a region that is complementary to any portion of a sequence of a telomerase RNA (SEQ ID NO:1).

22. A pharmaceutical composition comprising an oligonucleotide of claim 16, or a pharmaceutically acceptable salt thereof and a pharmaceutically acceptable carrier.

23. A kit comprising an oligonucleotide of claim 16, or a salt thereof.

24. A method of preparing a compound of formula (I):

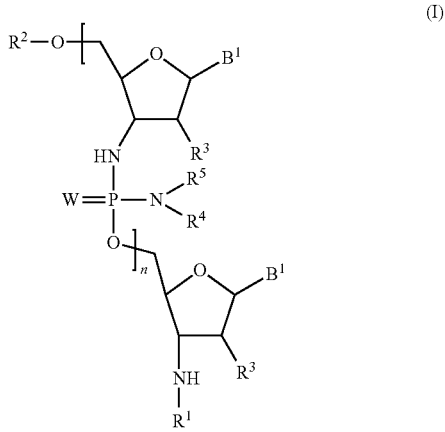

wherein
R$^1$ is hydrogen or an amino protecting group;
R$^2$ is hydrogen or a hydroxyl protecting group;
each R$^3$ is independently selected from hydrogen, hydroxyl, and —O—R$^{3a}$;
  wherein each R$^{3a}$ is C$_{1-6}$ alkyl or a C$_{1-6}$ alkyl substituted with —NR$^{3b}$R$^{3c}$, imidazolyl, —(CH$_2$)$_a$O(CH$_2$)$_b$NR$^{3b}$R$^{3c}$, or —(CH$_2$)$_a$ONR$^{3d}$(CH$_2$)$_b$NR$^{3b}$R$^{3c}$;
    wherein each R$^{3b}$ is hydrogen or C$_{1-2}$ alkyl;
    each R$^{3c}$ is hydrogen or C$_{1-2}$ alkyl;
    each R$^{3d}$ is hydrogen or C$_{1-2}$ alkyl;
    each a is an integer selected from one to 4;
    each b is an integer selected from one to 4;
each W is independently selected from O, S, and Se;
each B$^1$ is independently selected from a heterocyclic base moiety and a protected heterocyclic base moiety;
each R$^4$ is independently C$_{1-6}$ alkyl or a C$_{1-6}$ alkyl substituted with —NR$^{4a}$R$^{4b}$;
  wherein R$^{4a}$ is hydrogen or C$_{1-2}$ alkyl and R$^{4b}$ is hydrogen or C$_{1-2}$ alkyl;
each R$^5$ is independently C$_{1-6}$ alkyl or a C$_{1-6}$ alkyl substituted with —NR$^{5a}$R$^{5b}$;
  wherein R$^{5a}$ is hydrogen or C$_{1-2}$ alkyl and R$^{5b}$ is hydrogen or C$_{1-2}$ alkyl; or
R$^4$ and R$^5$ taken together with the nitrogen to which they are attached form a monocyclic heterocyclyl or a monocyclic heterocyclyl substituted with C$_{1-6}$ alkyl, sperminyl, or spermidinyl; and n is an integer selected from one to 50;
or a salt thereof;
wherein the method comprises:
a) contacting a compound of formula (II)

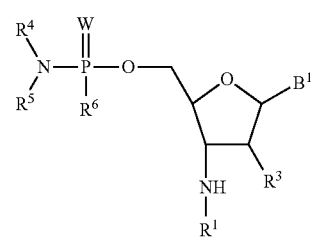

(II)

with a compound of formula (B):

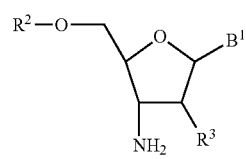

(B)

* * * * *

SEQUENCE LISTING

```
<160> NUMBER OF SEQ ID NOS: 4

<210> SEQ ID NO 1
<211> LENGTH: 451
<212> TYPE: RNA
<213> ORGANISM: Artificial Sequence
<220> FEATURE:
<223> OTHER INFORMATION: Synthetic Construct

<400> SEQUENCE: 1
ggguugcgga ggguggggccu gggaggggug guggccauuu uuugucuaac ccuaacugag     60
aagggcguag gcgccgugcu uuugcucccc gcgcgcuguu uuucucgcug acuuucagcg    120
ggcggaaaag ccucggccug ccgccuucca ccguucauuc uagagcaaac aaaaaauguc    180
agcugcuggc ccguucgccc cucccgggga ccugcggcg  gucgccugcc cagccccga    240 accccgccug gaggccgcgg ucggcccggg gcuucuccgg aggcacccac ugccaccgcg    300
aagaguuggg cucugucagc cgcgggucuc ucggggggcga gggcgagguu caggccuuuc    360
aggccgcagg aagaggaacg gagcgagucc ccgcgcgcgg cgcgauuccc ugagcugugg    420
```

```
gacgugcacc caggacucgg cucacacaug c                                    451

<210> SEQ ID NO 2
<211> LENGTH: 11
<212> TYPE: DNA
<213> ORGANISM: Artificial Sequence
<220> FEATURE:
<223> OTHER INFORMATION: Synthetic Construct

<400> SEQUENCE: 2
gttagggtta g                                                           11

<210> SEQ ID NO 3
<211> LENGTH: 13
<212> TYPE: DNA
<213> ORGANISM: Artificial Sequence
<220> FEATURE:
<223> OTHER INFORMATION: Synthetic Construct

<400> SEQUENCE: 3
tagggttaga caa                                                         13

<210> SEQ ID NO 4
<211> LENGTH: 13
<212> TYPE: DNA
<213> ORGANISM: Artificial Sequence
<220> FEATURE:
<223> OTHER INFORMATION: Synthetic Construct

<400> SEQUENCE: 4
cagttagggt tag                                                         13
```